US012085529B2

(12) United States Patent
Ito et al.

(10) Patent No.: US 12,085,529 B2
(45) Date of Patent: Sep. 10, 2024

(54) GLYCATED PROTEIN SENSOR, MEASUREMENT METHOD, PROGRAM, AND SENSOR MANUFACTURE METHOD

(71) Applicant: PROVIGATE INC., Tokyo (JP)

(72) Inventors: Narushi Ito, Tokyo (JP); Mitsumi Nishi, Tokyo (JP); Norikazu Katayama, Tokyo (JP); Yuuya Miyazawa, Tokyo (JP)

(73) Assignee: PROVIGATE INC., Tokyo (JP)

( * ) Notice: Subject to any disclaimer, the term of this patent is extended or adjusted under 35 U.S.C. 154(b) by 967 days.

(21) Appl. No.: 17/056,684

(22) PCT Filed: May 17, 2019

(86) PCT No.: PCT/JP2019/019640
§ 371 (c)(1),
(2) Date: Apr. 9, 2021

(87) PCT Pub. No.: WO2019/221264
PCT Pub. Date: Nov. 21, 2019

(65) Prior Publication Data
US 2021/0223200 A1    Jul. 22, 2021

(30) Foreign Application Priority Data
May 18, 2018    (JP) ................. 2018-095919

(51) Int. Cl.
*G01N 27/327*    (2006.01)
*C12Q 1/26*    (2006.01)
(Continued)

(52) U.S. Cl.
CPC ............. *G01N 27/327* (2013.01); *C12Q 1/26* (2013.01); *G01N 33/483* (2013.01); *G01N 33/72* (2013.01)

(58) Field of Classification Search
CPC ... C12Q 1/26; C12Q 1/28; C12Q 1/37; C12Q 1/005; G01N 27/3272; G01N 27/3276;
(Continued)

(56) References Cited

U.S. PATENT DOCUMENTS

| 5,789,221 A | 8/1998 | Kato et al. |
| 5,795,774 A | 8/1998 | Matsumoto et al. |

(Continued)

FOREIGN PATENT DOCUMENTS

| CN | 102076867 A | 5/2011 |
| CN | 102998265 A | 3/2013 |

(Continued)

OTHER PUBLICATIONS

Notice of Reasons for Refusal (Office Action) issued in Japanese Patent Application No. 2020-519938, with English translation (Apr. 7, 2023).

(Continued)

*Primary Examiner* — Gurpreet Kaur
(74) *Attorney, Agent, or Firm* — McBee Moore & Vanik, IP, LLC

(57) ABSTRACT

Provided is a glycated protein sensor provided with: immobilized protease; immobilized ketoamine oxidase; and a hydrogen peroxide detection section.

19 Claims, 37 Drawing Sheets

(51) Int. Cl.
*G01N 33/483* (2006.01)
*G01N 33/72* (2006.01)

(58) Field of Classification Search
CPC .. G01N 27/3271; G01N 33/483; G01N 33/72; C12N 11/02; F25B 2400/23; F25B 2600/2509
See application file for complete search history.

(56) References Cited

U.S. PATENT DOCUMENTS

| | | | |
|---|---|---|---|
| 6,951,728 | B2 | 10/2005 | Suyue et al. |
| 2004/0018272 | A1 | 1/2004 | Chen |
| 2010/0002526 | A1 | 1/2010 | Dillon et al. |

FOREIGN PATENT DOCUMENTS

| | | | |
|---|---|---|---|
| EP | 678576 | A2 | 10/1995 |
| EP | 0921198 | A1 * | 4/1998 ............... C12Q 1/26 |
| EP | 1361436 | A1 | 11/2003 |
| EP | 2283149 | A1 | 2/2011 |
| JP | H1026601 | A | 1/1998 |
| JP | H11243950 | A | 9/1999 |
| JP | 2004004071 | A | 1/2004 |
| JP | 2004-251900 | A | 9/2004 |
| JP | 2004-333455 | A | 11/2004 |
| JP | 2005283192 | A | 10/2005 |
| JP | 2009171874 | A | 8/2009 |
| JP | 2013-74876 | A | 4/2013 |
| WO | 2007/094354 | A1 | 8/2007 |
| WO | 2009/140343 | A1 | 11/2009 |
| WO | 2013/038735 | A1 | 3/2013 |

OTHER PUBLICATIONS

PCT International Search Report for PCT/JP2019/019640, mailed Jul. 16, 2019.

* cited by examiner

GLYCATED PROTEIN SENSOR, MEASUREMENT METHOD, PROGRAM, AND SENSOR MANUFACTURE METHOD

CROSS-REFERENCE TO RELATED APPLICATIONS

This application is the National Stage entry of International Application No. PCT/JP2019/019640, filed 17 May 2019, which claims priority to Japan No. 2018-095919, filed 18 May 2018.

BACKGROUND

Field

The present disclosure relates to a glycated protein sensor, a measurement method, a program and a method of manufacturing a sensor.

Glycoprotein is measured for diabetes diagnostic and as a management index of glycemic control. As an example, glycated hemoglobin and glycated albumin are frequently measured in clinical practice. As methods for measuring glycated proteins, electrophoresis, ion exchange chromatography, affinity chromatography, immunization, and enzymatic methods have been known, but enzyme methods have become the mainstream in recent years because accurate but simple and rapid measurements are desired.

In general methods to measure glycated protein by the general enzyme method, first, the protein is degraded into amino acids by protease in the first step, only the glycated amino acid of these amino acids is reacted with ketoamine oxidase in the second step to generate hydrogen peroxide, and the hydrogen peroxide is converted into a color development reaction in the third step to measure the absorbance.

Description of Related Art

In the conventional glycated protein measurement methods, the coexistence of protease and ketoamine oxidase leads to a degradation reaction between enzymes occurs, and therefore, measurements with high accuracy have been difficult. In addition, in the conventional glycated protein measurement methods, multiple steps are involved for a measurement, thus it has been difficult to perform a rapid measurement, and there has been a problem that measurement errors are likely to occur depending on the technique of the person in charge of the test.

SUMMARY

According to one embodiment of the present disclosure, a glycated protein or fructosamine sensor comprises an immobilized protease, an immobilized ketoamine oxidase, and a hydrogen peroxide detection portion.

The test sample may be a solution. The solution may be a body fluid, a solution derived from a body fluid, and may be a dilute fluid of a body fluid. The solution may be a solution that is not a body fluid (derived from a non-body fluid), and may be a mixture of a solution derived from a body fluid or a body fluid and a solution derived from a non-body fluid. The solution may be a solution used for sample measurements and may be a solution used for measurements for calibration. For example, the solution may be a standard solution or a calibration solution.

The "body fluid" may be blood, serum, plasma, lymph fluid, tissue fluids such as interstitial fluid, intercellular fluid, interstitial fluid, and the like, and may be body cavity fluid, serosal fluid, pleural fluid, ascites fluid, pericardial fluid, cerebrospinal fluid, joint fluid (synovial fluid), and aqueous humor of the eye (aqueous humor). The body fluid may be digestive fluid such as saliva, gastric juice, bile, pancreatic juice, intestinal fluid, etc., and may be sweat, tears, nasal mucus, urine, semen, vaginal fluid, amniotic fluid, milk, etc. The body fluid may be a body fluid of an animal and may be a body fluid of a human. The "body fluid" may be a liquid (milk, dairy, etc.) in a food product containing a protein from an animal. The body fluid may be a body fluid of a plant, a plant biological fluid, or a liquid derived from a plant. For example, the body fluid may be fruit juice, dense, sap of a plant. The "body fluid" may be a solution.

In some embodiments, the solution may comprise a physiological buffer. The solution may include an subject to be measured. The buffer may be a buffer called Good buffer. The buffer may include phosphate buffered saline (PBS) or N-tris(hydroxymethyl)methyl-2-aminoethanesulfonic acid buffer (TES). The buffer may comprise at least one of or a mixture of 2-morpholinoethanesulfonic acid (MES), 3-morpholinopropanesulfonate (MOPS), 2-hydroxy-3-morpholinopropanesulfonate (MOPSO), piperazine-1,4-bis(2-hydroxy-3-propanesulfonate) dihydrate (POPSO), N-(2-acetamide)iminodiacetic acid (ADA), piperazine-1,4-bis(2-ethanesulfonate)monosodium (PIPES), N-(2-acetamide)-2-aminoethansulfonate (ACES), colaminate, N,N-bis(2-hydroxyethyl)-2-aminoethanesulfonic acid (BES), N-tris (hydroxymethylmethyl-2-aminoethanesulfonic acid (TES), 2-[4-(2-hydroxyethyl)-1-piperazinyl]ethanesulfonic acid (HEPES), 2-[4-(2-hydroxyethyl)-1-piperazinyl]ethanesulfonate (HEPES-Na), acetamidoglycine, tricine, glycinamide, bicine, bis(2-hydroxyethyl)aminotris(hydroxymethylmethane) (Bis-Tris), N-cyclohexyl-3-aminopropanesulfonic acid (CAPS), N-cyclohexyl-2-hydroxy-3-aminopropanesulfonate (CAPSO), N-cyclohexyl-2-aminoethanesulfonate (CHES), 3-[N,N-bis(2-hydroxyethyl)amino]-2-hydroxypropanesulfonate (DIPSO), 3-[4-(2-hydroxyethyl)-1-piperadinyl]propanesulfonate (HEPPS), 2-hydroxy-3-[4-(2-hydroxyethyl)-1-piperadinyl]propanesulfonic acid monohydrate (HEPPSO), N-tris(hydroxymethyl)methyl-3-aminopropanesulfonic acid (TAPS), and 2-hydroxy-N-tris(hydroxymethyl)methyl-3-aminopropanesulfonic acid (TAPSO).

The solution may contain a substance to be measured. For example, the solution may be tears and the substance to be measured may be glycoalbumin contained in tears. Alternatively, the subject to be measured may be albumin, glycoalbumin, hemoglobin, glycated hemoglobin in blood or serum, albumin and glycoalbumin in interstitial fluid, albumin and glycoalbumin in tears, albumin and glycoalbumin in urine, or albumin and glycoalbumin in saliva.

In some embodiments, the object to be sensed may be fructosamine. In some embodiments, the sensor may be a fructosamine sensor. Fructosamine may be a glycated protein, may be a glycated peptide, and may be a glycated amino acid. The glycated protein may be glycated albumin and may be glycated hemoglobin. The glycated protein may be AGEs (Advanced Glycation End Products, terminal glycation products, late glycation products). In some embodiments, the subject to be sensed may be a glycated lipid.

"Immobilization" refers to immobilizing an enzyme (protease, ketoamine oxidase), or the like on a substrate or a base material. These enzymes may be immobilized to a base material immobilized on a substrate. In some embodiments, the enzyme may be immobilized directly or indirectly to walls of a device main body, an inner wall of a flow path, a chamber, or a container. The enzyme may be immobilized with respect to a subject to be immobilized via a member for the purpose of immobilization. The enzyme may be immobilized on the subject to be immobilized via one or more members which do not have an original purpose of immobilization. In some embodiments, an immobilized subject to which an enzyme is immobilized may be substantially movable relative to a device main body or the like. For example, the enzyme may be immobilized on a bead and the bead may be movable with respect to a flow path along with movement of the solution.

Immobilization methods include, for example, covalent bonding, physisorption, ionic bonding, cross-linking, inclusion, biochemical specific bonding, and the like. Depending on the enzyme used, an immobilization method which would not deactivate enzyme may be selected, or a plurality of immobilization methods may be used in combination. In some embodiments, a protein may be used as a base material to which the enzyme is mixed and then solidified with a crosslinking agent such as glutaraldehyde. Thus, even when a relatively expensive enzyme is used, the cost can be reduced. In some embodiments the enzymes may be immobilized using a fluorine-based resin, a hydraulic resin, a photocurable resin, a solid polyelectrolyte, a polyion complex may be confined using a water-insoluble semipermeable membranes such as nylon, ethyl cellulose, acetyl cellulose, polystyrene, or may be confined using phospholipids in liposomes or reverse micelles.

In order to immobilize the base material to the substrate, an adhesive such as a silane coupling agent may be used. The adhesive may be formed as a layer (silane coupling layer) between the substrate and the base material. The hydrogen peroxide detection portion and the layer thereon may be bonded, for example, via a bonding agent. Various bonding agents may be used so long as they do not substantially inhibit the measurement principles of the present disclosure. The bonding agent may include, for example, a material for bonding an inorganic material and an organic material. The bonding agent may be, for example, a silane coupling agent. Silane coupling agents exemplarily include:

Vinyl based: vinyltrimethoxysilane, vinyltriethoxysilane, 7-octenyltrimethoxysilane, vinyldimethylethoxysilane, vinylmethyldimethoxysilane, vinylmethyldiethoxysilane, vinyltris(2-methoxyethoxy)silane, vinyltris(trimethylsiloxy)silane, 4-vinylphenyltrimethoxysilane, allyltrimethoxysilane, allyltriethoxysilane, 5-(triethoxysilyl)-2-norbornene;

Styryl based: p-styryl trimethoxysilane;

Methacryl based: 3-methacryloxypropyltrimethoxysilane, 3-methacryloxypropylmethyldimethoxysilane, 3-methacryloxypropyltriethoxysilane, 3-methacryloxypropylmethyldiethoxysilane, 3-methacryloxypropyltris(trimethylsiloxy)silane, 3-methacryloxypropyltriarylsilane, 8-methacryloxyoctyltrimethoxysilane;

Acryl based: 3-acryloxypropyltrimethoxysilane, 3-acryloxypropyldimethylmethoxysilane, 3-acryloxypropyltriallylsilane;

Epoxy based: 3-glycidoxypropyltrimethoxysilane, 3-glycidoxypropylmethyldimethoxysilane, 3-glycidoxypropylmethyldiethoxysilane, 8-glycidoxyoctyltrimethoxysilane, 2-(3,4-epoxycyclohexyl)ethyltrimethoxysilane;

Amino based: N-2-(aminoethyl)-3-aminopropyltrimethoxysilane, N-2-(aminoethyl)-3-aminopropylmethyldimethoxysilane, N-2-(aminoethyl)-3-aminopropyltriethoxysilane, N-2-(aminoethyl)-8-aminooctyltrimethoxysilane, N-6-(aminohexyl)-3-aminopropyltrimethoxysilane, 3-aminopropyltrimethoxysilane, 3-aminopropylmethyldimethoxysilane, 3-aminopropyltriethoxysilane (APTES), 3-aminopropylmethyldiethoxysilane, 3-triethoxysilyl-N-(1,3-dimethylbutylidene)propylamine, N-phenyl-3-aminopropyltrimethoxysilane, N-methyl-3-aminopropyltrimethoxysilane, N,N-dimethyl-3-aminopropyltrimethoxysilane, bis[3-(trimethoxysilyl)-propyl]amine, N-(vinylbenzyl)-2-aminoethyl-3-aminopropyltrimethoxysilane hydrochloride;

Ureide based: 3-ureidopropyl trimethoxysilane, 3-ureidopropyl triethoxysilane;

Azide based: 11-azidoundecyltrimethoxysilane;

Isocyanate based: 3-isocyanate propyltrimethoxysilane, 3-isocyanate propyltriethoxysilane;

Isocyanurate based: Tris-(trimethoxysilylpropyl)isocyanurate;

Mercapto based: 3-mercaptopropyltrimethoxysilane, 3-mercaptopropylmethyldimethoxysilane, 3-mercaptopropyltriethoxysilane;

or acid anhydride: 3-trimethoxysilylpropylsuccinic anhydride.

The substrate may contain $SiO_2$ as a main component or may be a glass substrate. The substrate may include a polymer or a resin. The substrate may include a transparent polymer material. The substrate may be configured to include, for example, a resin material such as polyethylene terephthalate (PET), polyethylene naphthalate (PEN), or cycloolefin polymer (COP), or the like. The substrate may be a transparent substrate or an opaque substrate. The substrate may be a flexible substrate. The substrate may be a sapphire substrate.

The main component of the base material may be a polymer. The main component of the base material may be a biopolymer, an organic polymer, or an inorganic polymer. For example, the base material may be or include a porous inorganic material such as silica gel, glass, alumina, molecular sieve, celite, charcoal, ceramic material such as kaolinite, ceramic, hydroxyapatite, a clay such as bentonite, acidic clay, polyacrylamide gel, a polyvinyl alcohol resin, urethane polymer, silicone resin, styrene resin, perfluorosulfonic acid resin, lacquer cellulose, agar, polysaccharide such as alginic acid, carrageenan, collagen (glue or gelatin), chitin, chitosan, polypeptide, or polylysine.

The main component of the base material may be a protein. The main component of the base material may be bovine serum albumin (BSA). When a base material is composed of a protein, generally, a crosslinking agent is used to crosslink and immobilize an enzyme and the protein of the base material. The protein serving as a main component of the base material and the crosslinking agent may be combined and referred to as a "base material" The crosslinking agent may be a photosensitive resin, a water-curable resin, or a thermosetting. The crosslinking agent may be a bifunctional reagent such as glutaraldehyde. The crosslinking agent may be formaldehyde, and may be a bifunctional reagent selected from glyoxal, malondialdehyde, succinaldehyde, and glutaraldehyde.

The main component of the base material may be an ion matrix, and a polyion complex (hereinafter, simply referred to as an ion complex). By mixing polyanions and polycations in aqueous solution, polyion complexes due to strong electrostatic interactions are formed. The ion matrix may be electrostatically immobilized to the substrate. The ionic matrix is capable of electrostatically confining enzymes within the matrix. For example, by mixing oppositely charged (cations and anions) polymers such as polyamino acids, complexes can be formed by electrostatic interactions, into which the enzymes and the like can be confined. Since the ion matrix does not directly bind to the enzyme, a decrease in the activity of the enzyme can be reduced or avoided. The ion matrix may be used for an enzyme which is likely to deactivate by a crosslinking method.

The base material may be a bead. The beads may be carbon fine particles (carbon beads) and may be silica (SiO$_2$) fine particles (silica beads). The beads may be polymeric beads. The material of the beads may be a polymeric polysaccharide such as chitin, chitosan or alginic acid. The bead may be a bead containing a fine metal particle or a magnetizing substance, and may be a magnetic bead. The size of the beads may be 10 nm or greater in terms of their average particle size, and may be 200 nm or smaller. The enzyme may be crosslinked to the bead. The beads may be directly immobilized to the substrate or another base material, and may be disposed so as to be contained within a predetermined volume even if they are not immobilized to the substrate, the base material, or the like. The beads may be movable with a flow of solution without being immobilized to the device main body. The beads may be disposed so as not to substantially come out of the container portion even if they are not immobilized directly to the container portion containing them. Thus, for example, the beads can be maintained in their position while removing unnecessary substances by flowing or rinsing with a diluent, a washing solution, or the like. This allows, for example, repeated uses.

The base material may comprise a porous material. The porous material may be a ceramic, and may be a carbon material. The base material may be a zeolite. The base material may be a metal-organic structure.

"Protease" is a generic term for peptide bond hydrolyzing enzymes that hydrolyze and catabolize proteins and polypeptides. A protease may be an enzyme that degrades a protein into peptide fragments. When a protein contains glycated amino acid residue, peptide fragments containing a glycated amino acid residue and peptide fragments not glycated at all may be present in peptide fragments generated by the action of a protease.

A "protease" may be a protease derived from an animal, may be a protease derived from a plant, and may be a protease derived from a microorganism. The protease may be an exopeptidase and may be an endopeptidase. The protease may be an aspartic protease, a metal protease, a serine protease, or a thiol protease.

A "protease" may comprise a plurality of types or kinds of proteases and may comprise one type or kind of protease. For example, a protease may comprise one or both of a proteinase and a peptidase. Mixing multiple proteases may increase the efficiency of degradation. The protease may comprise a modification-type protease or a modified protease. The proteases may be used with an additive. The additive may be, for example, a surfactant, urea. The additive can destabilize or denature proteins, for example without limitation. By use of a modified protease or an additive, the efficiency of degradation of a protein and the selectivity of the base material can be improved, for example without limitation.

The protease derived from an animal may be trypsin, chymotrypsin, pepsin, elastase, bovine pancreatic protease, cathepsin, calpain, protease type-I, protease type-XX, aminopeptidase N, carboxypeptidase, pancreatin (a mixture of multiple enzymes such as proteases and amylases), or the like.

The protease derived from a plant may be papain, bromelain, gingipain, kallikrein, ficin, chymopapain, actinidin, carboxypeptidase W, and the like.

The proteases derived from a microorganism may be genera *Bacillus* (or origin, the same applies below), *Geobacillus, Paenibacillus, Aspergillus, Penicillium, Streptomyces*, Lysobacter, Yeast, *Tritirachium, Thermus, Pseudomonas, Achromobacter, Rhizopus, Staphylococcus*, or the like.

The protease may be selected based on the digestion or degradation efficiency of the protein, e.g., by absorbance measurement. In some embodiments, proteases having a difference in absorbance of 100 mAbs or more before and after degradation of albumin (HSA) may be used. The difference in absorbance before and after the degradation of albumin (HSA) may be 90 mAbs or more. The difference in absorbance before and after degradation of albumin (HSA) may be 110 mAbs or more.

The protease may be selected from the group consisting of Protease-type XXIV, Orientase 22BF, Orientase 90N, Toyoteam NEP-160, and alkalophilic proteases. The protease may be selected from the group consisting of Protease-type XXIV, Orientase 22BF, Orientase 90N, Toyoteam NEP-160, and alkalophilic proteases. The protease may be selected from the group consisting of a Pronase, and a Protease-type XIV.

The protease may be any one of a neutral protease, an acidic protease, and an alkaline protease. For example, when tears are measured, neutral or weakly alkaline proteases may be employed. The protease may be a thermostable protease (e.g., Thermolysin) that maintains activity even in a high temperature range (e.g., 60° C. or higher). The protease may be a cold active protease that maintains activity even in a low temperature range (e.g., 30° C. or lower).

In some embodiments, the protease may be arranged in a dry state within a sensor. The protease may be formed by natural drying, freeze drying or spray drying, for example without limitation. In some embodiments, it may be arranged in a state dissolved in a solution. Protease dissolved in solution may be stored cool until use. The proteases may be frozen with the solution and may be dissolved and used in use. The protease may be kept in a moisture-containing environment without drying. For example, a protease may be disposed in a gel.

A "ketoamine oxidase" is an oxidizing enzyme that recognizes a ketoamine structure of a peptide or a peptide fragment containing a glycated amino acid or a glycated amino acid residue, and oxidizes the glycated amino acid to produce an amino acid, a glucosone (α-ketoaldehyde) and hydrogen peroxide. Thus, a ketoamine oxidase produces an amount of hydrogen peroxide proportional or related to the amount of the peptides or the peptide fragments comprising glycated amino acid or glycated amino acid residue to be recognized.

The ketoamine oxidase may be a dehydrogenase, may be a kinase, or may be an oxidase. The ketoamine oxidase may be a fructosyl amino acid oxidase (FAOD), a fructosyl peptide oxidase, a fructosyl valylhistidine oxidase, a fructosyl amine oxidase, amadriase, a fructosyl amine deglycase or modified forms thereof.

In some embodiments, the ketoamine oxidase may be an oxidase in which the ε-amino group acts on a glycated amino acid or peptide. The amino acid may be lysine. By using an oxidase in which an ε-amino group selectively acts on a glycated amino acid or peptide, a glycoalbumin sensor can be constructed.

In some embodiments, the ketoamine oxidase may be an oxidase in which the α-amino group acts on a glycated amino acid or peptide. The amino acid may be valine. By using an oxidase in which the α-amino group acts on a glycated amino acid or a peptide, a glycated hemoglobin sensor or a glycated hemoglobin A1c (HbA1c) sensor can be constructed.

In some embodiments, the sensor may comprise a detection portion. The detection portion may be a hydrogen peroxide detection portion. The "hydrogen peroxide detection portion" (hydrogen peroxide sensor) may be an electrode of an electrochemical type, and may be a hydrogen peroxide electrode. The hydrogen peroxide electrode may have a counter electrode, a reference electrode, and a working electrode. In some embodiments, the detection portion may detect oxygen. For example, the amount or concentration of oxygen that decreases in an enzymatic reaction may be detected. Oxygen detection is considered to be relatively insensitive to molecules and ions as noise sources and to be resistant to interference. Oxygen consumption may be measured by oxygen detection. Since tears are atmospherically saturated at the time of collection, the detection portion may be used for sensing oxygen in tears. The detection portion may be configured so that a plurality of detection methods can be used selectively or in combination.

The detection of hydrogen peroxide may be an optical detection. The optical detection may include measurement of absorbance and emission. For example, by adding peroxidase, 4-aminoantipyrine and a color former, a color change of a quinone dye caused by oxidative condensation may be measured, for example, from a back surface of a transparent substrate. In some embodiments, the detection portion may include a luminescent reagent and a photodetector. For example, luminol may be used as a luminescent reagent. The luminol may be arranged in a powder form. Hydrogen peroxide may be reacted with luminol, and the intensity of emission (wavelength 460 nm) by the luminol reaction may be measured. The reagents may further include potassium hexacyanoferrate, sodium hydroxide, or the like. The luminol reaction may be measured by an electrochemiluminescence method in which a gold electrode, a platinum electrode, or an indium tin oxide (ITO) transparent electrode is used and driven by an alternating current. In other cases of detecting a fluorescent reaction, a combination of oxalic acid ester and a fluorescent substance may be used, or lucigenin (acridinium, bis(N-methylacridinium)) may be used. The detection portion may be a hydrogen peroxide sensor of another type.

The term "on the detection portion" may be an upper portion of a part of the surface of the detection portion, or may be disposed so as to cover the entire detection portion. It may also be on a detection portion formed on a substrate. The entire surface of the substrate may be covered, or a part of the substrate may be covered while covering the detection portion.

The sensor may have a liquid container portion. The liquid container portion may comprise one, two or all of an immobilized protease, an immobilized ketoamine oxidase and a detection portion. The liquid container portion may extend in the longitudinal direction. The volume of the liquid container portion may be less than or equal to 1 mL, 500 µL, 300 µL, 200 µL, 100 µL, 50 µL, 30 µL, 20 µL, 10 µL, 5 µL, 4 µL, 3 µL, 2 µL, 1 µL, 0.9 µL, 0.8 µL, 0.7 µL, 0.6 µL, 0.5 µL, 0.4 µL, 0.3 µL, 0.2 µL, or 0.1 µL. The liquid container portion may have a liquid inlet. The liquid container portion may have a liquid outlet. The liquid container portion may have an air hole. The air hole may have a function of discharging the gas that has been in the liquid container portion to the outside of the sensor when the liquid is introduced into the liquid container portion.

Exemplary or potential effects by the glycated protein sensors and the like of the present disclosure will be explained. Proteases can degrade other proteases. Proteases can also degrade (ketoamine) oxidases. Unimmobilized proteases can move in liquid, such as by diffusion, encounter other proteases and ketoamine oxidases, and degrade them. Solutions of proteases are not suitable for storage, and solid proteases need to be weighed each time. By immobilizing the proteases in the device beforehand, the measurement procedure can be made more efficient. The immobilized proteases can be used repeatedly. By immobilizing the ketoamine oxidase and the protease of the present invention, repeated measurements become possible, and the running cost per one measurement can be greatly reduced. The interior of the device may be cleaned between measurements. The glycated protein sensors of the present disclosure can be miniaturized. Further, when the hydrogen peroxide detection portion and the ketoamine oxidase immobilization layer are in close proximity, the diffusion distance of hydrogen peroxide becomes short, and interfering substances in a body fluid reacting with hydrogen peroxide will affect less. When an immobilized layer of ketoamine oxidase and protease is formed as a thin film of, for example, 1 micrometer (µm) or less and is formed on a hydrogen peroxide detection portion, for example, they come into close proximity to each other, thereby enabling highly sensitive measurement. Further, even if the amount of enzyme which is expensive as agent is small, a predetermined sensitivity can be obtained, and it is also possible to reduce the production costs.

Embodiments in which one or more features of the present disclosure described above are arbitrarily combined and are also included in the scope of the present disclosure.

DETAILED DESCRIPTION OF A PREFERRED EMBODIMENT

1. Structure of Sensor

Figure 1:
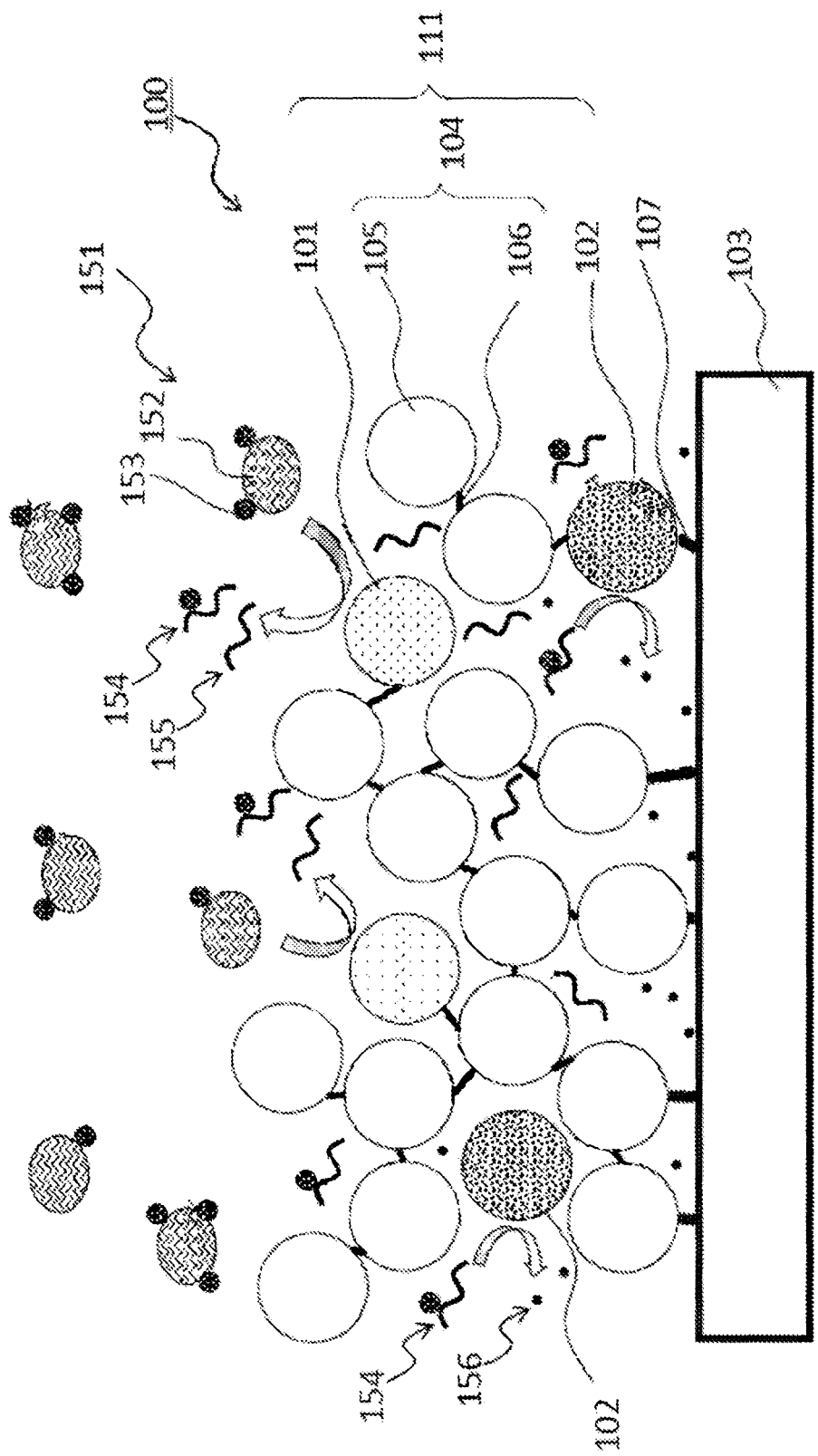
FIG. 1 illustrates a schematic cross-sectional view of a sensor according to an embodiment of the present disclosure.

With reference to FIG. 1, the configuration of a glycated protein sensor according to an embodiment of the present disclosure will be described. Sensor 100 shown in FIG. 1 includes protease 101, ketoamine oxidase 102, and hydrogen peroxide detection portion 103. The proteases 101 and the ketoamine oxidases 102 are crosslinked by glutaraldehyde 106, which is a crosslinking agent, to bovine serum albumin 105, which is a base material. Bovine serum albumins 105 are also cross-linked to each other. These form immobilization layer 104. The immobilization layer 104 is connected to the hydrogen peroxide detection portion 103 by silane coupling agent 107. Thus, the proteases 101 and the ketoamine oxidases 102 are immobilized on the hydrogen peroxide detection portion 103 or the entire sensor 100. The immobilization layer 104, and the proteases 101 and the ketoamine oxidases 102 immobilized by it are combined to form enzyme layer 111.

Glycated protein 151 is introduced to the sensor 100. The glycated protein 151 has a structure in which sugar 153 is linked to protein 152. The glycated protein 151 is degraded by the protease 101 to yield peptide fragments.

Peptide fragments include glycated peptide fragments 154 and non-glycated peptide fragments 155. It is considered that these peptide fragments diffuse through the immobilized membrane 104. The glycated peptide fragments 154 react with the ketoamine oxidase 102 to yield glucosone (not shown) and hydrogen peroxide 156.

It is considered that this hydrogen peroxide 156 also diffuses in the immobilization film 104. The hydrogen peroxide detection portion 103 detects this hydrogen peroxide 156 and outputs a signal related to the concentration thereof.

When the hydrogen peroxide detection portion 103 is a hydrogen peroxide electrode, hydrogen peroxide 156 is decomposed by a hydrogen peroxide electrode, and electrons emitted are detected as a current. The reaction can be described as follows:

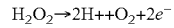

Hydrogen peroxide 156 is consumed at the hydrogen peroxide electrode 103. Therefore, the concentration of hydrogen peroxide 156 in the immobilized film 104 is lowest in the vicinity of the hydrogen peroxide detection portion 103 and increases as it goes away from the hydrogen peroxide detection portion 103. In other words, a concentration gradient of hydrogen peroxide 156 is present in the immobilization film 104. This concentration gradient changes immediately after the start of the measurement and becomes almost stable after a predetermined time. When this is stable, the concentration of hydrogen peroxide 156 detected by the hydrogen peroxide electrode 103 is related to the concentration of the glycated protein 151 introduced into the sensor 100. In advance, the relationship between the concentration of the glycated protein 151 and the current value generated by the hydrogen peroxide electrode 103 is determined. When an actual measurement is performed, based on this calibration, the concentration of the glycated protein 151 in the subject solution can be calculated from the current value generated by the hydrogen peroxide electrode 103.

In sensors according to some embodiments, the protease and the ketoamine oxidase may be immobilized on the same base material (integral type).

Figure 2:
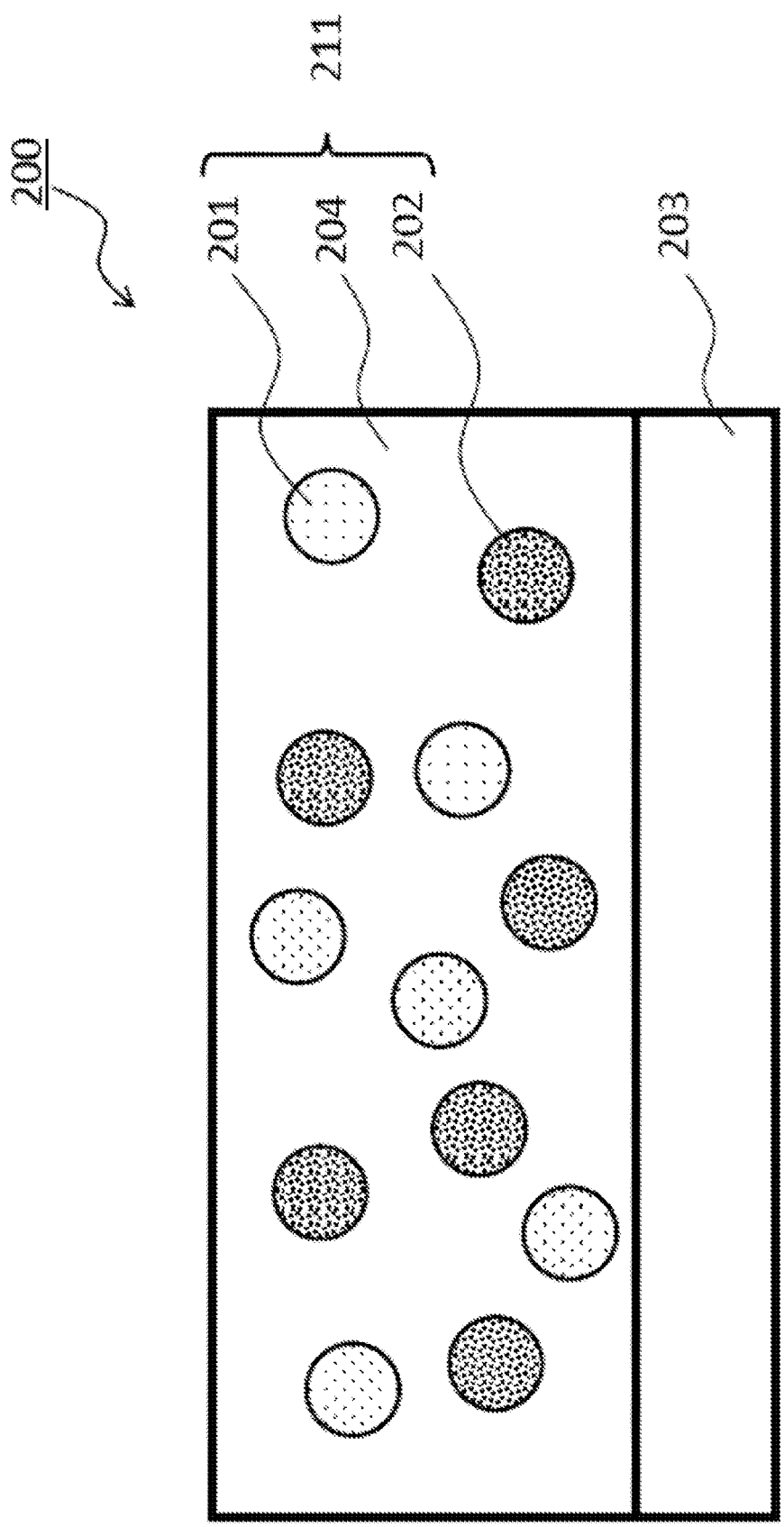
FIG. 2 illustrates a schematic cross-sectional view of a sensor according to an embodiment of the present disclosure.

FIG. 2 shows a structure of an integrated sensor according to some embodiments (second embodiment). Sensor 200 includes protease 201, ketoamine oxidase 202, base material 204, and hydrogen peroxide detection portion 203. The protease 201 and the ketoamine oxidase 202 are immobilized to the base material 204, and the base material 204 is immobilized to the hydrogen peroxide detection portion 203. In the sensor 200 shown in FIG. 2, the same base material 204 is formed as a layer or a film on the hydrogen peroxide detection portion 203, and enzyme layer 211 in which the protease 201 and the ketoamine oxidase 202 are immobilized to the base material 204 is formed on the hydrogen peroxide detection portion 203. The protease 201 and the ketoamine oxidase 202 are immobilized in this same base material 204.

Figure 3:
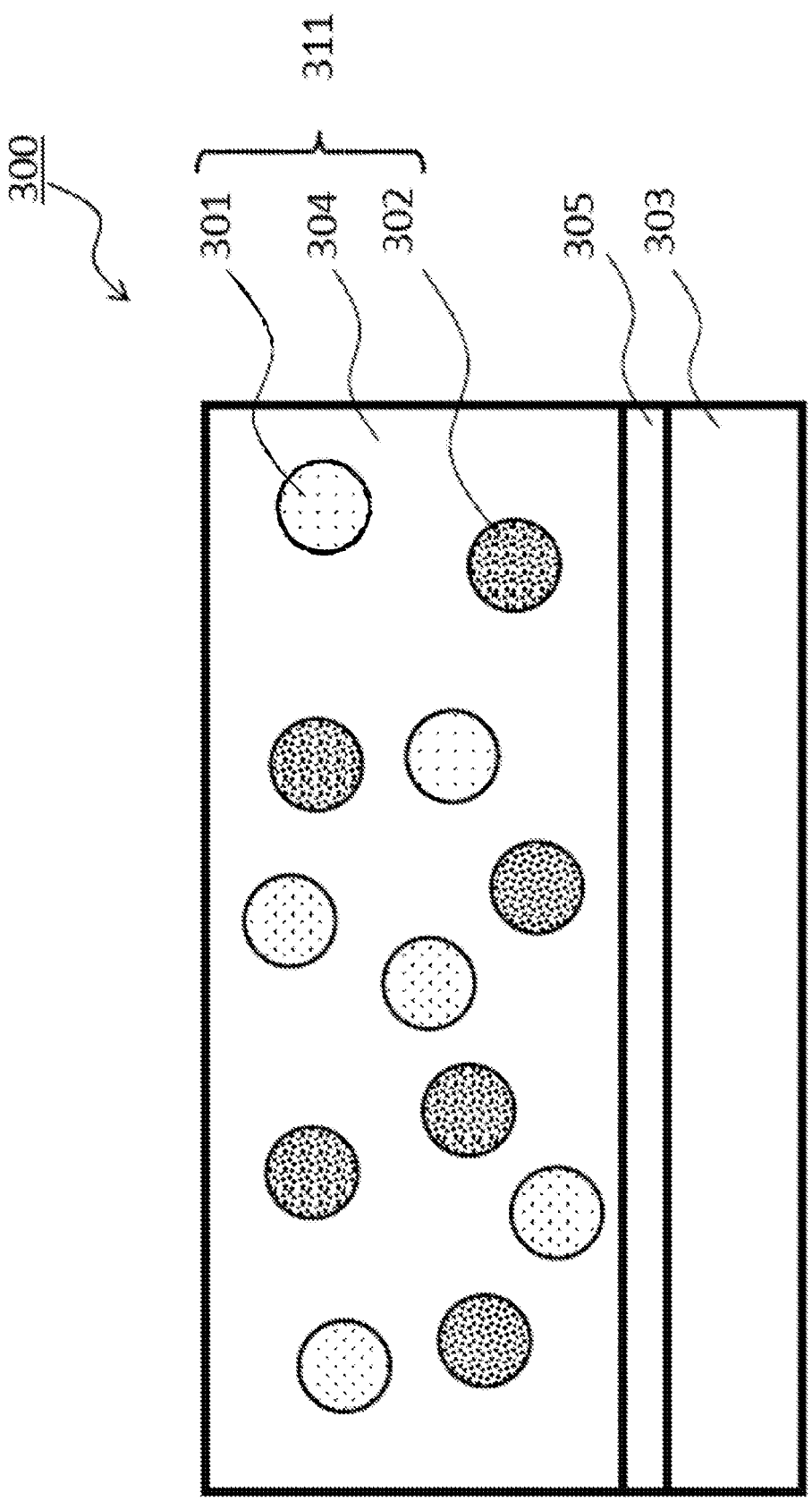
FIG. 3 illustrates a schematic cross-sectional view of a sensor according to an embodiment of the present disclosure.

FIG. 3 shows a structure of a sensor according to some embodiments (third embodiment). Sensor 300 has protease 301, ketoamine oxidase 302, base material 304 to which these are immobilized, and hydrogen peroxide detection portion 303 to which the base material 304 is immobilized. In the sensor 300 shown in FIG. 3, the same base material 304 is formed as a layer or a film on the hydrogen peroxide detection portion 303, and an enzyme layer 311 in which the protease 301 and the ketoamine oxidase 302 are immobilized to the base material 304 is formed on the hydrogen peroxide detection portion 303. The sensor 300 shown in FIG. 3 further includes an adhesive or bonding agent 305 between the base material 304 and the hydrogen peroxide detection portion 303 to bond them together. This bonding agent 305 may be a silane coupling agent. When the hydrogen peroxide detection portion 303 has a metal (not shown) such as an electrode on its surface, the silane coupling agent can relatively firmly bond the metal and the base material 304 made of an organic material.

Figure 4:
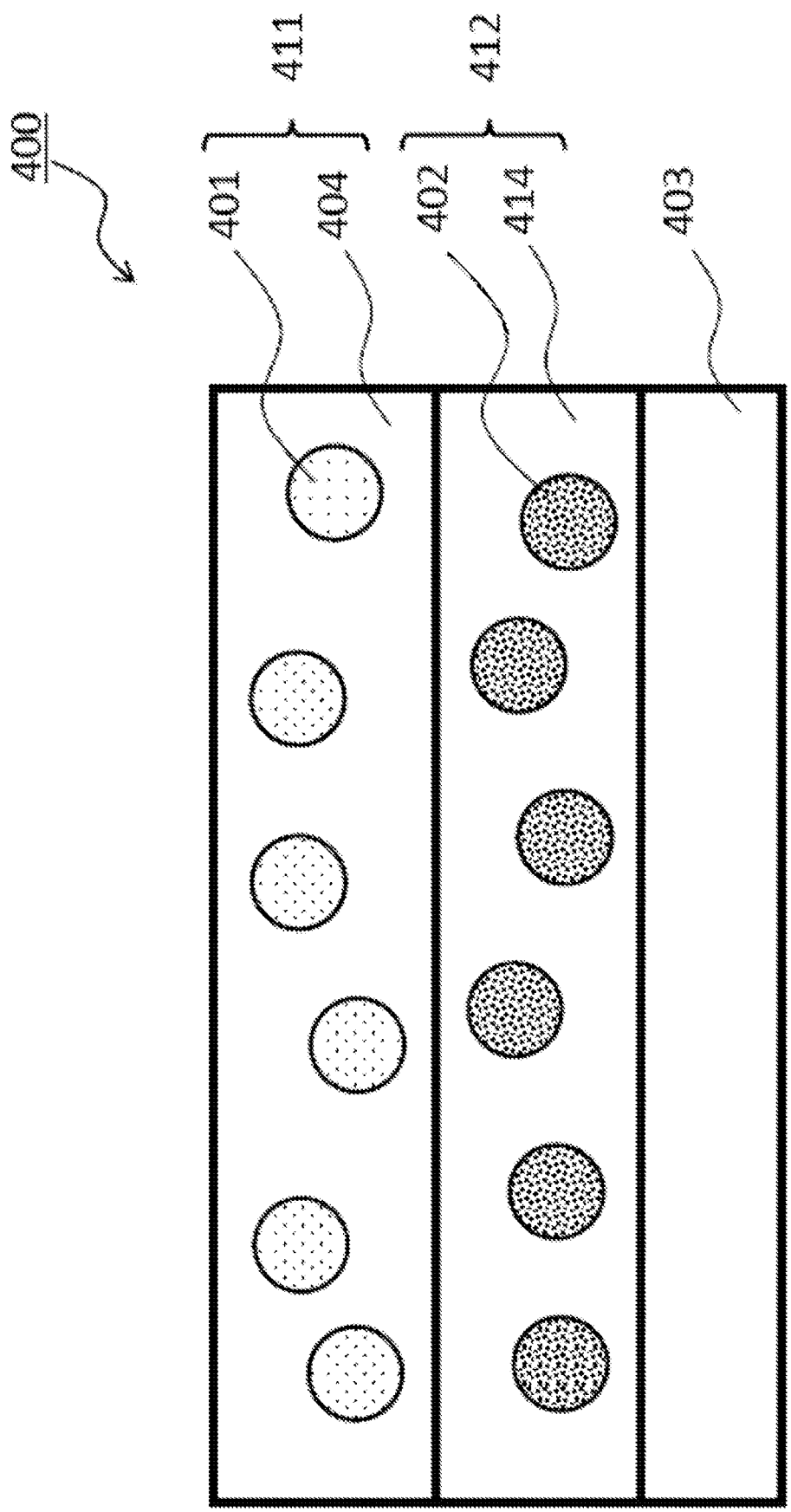
FIG. 4 illustrates a schematic cross-sectional view of a sensor according to an embodiment of the present disclosure.

FIG. 4 shows the structure of a sensor according to some embodiments (fourth embodiment). Sensor 400 has protease 401, ketoamine oxidase 402, base material 404,414 to which these are immobilized, and hydrogen peroxide detection portion 403 to which the base material 414 is immobilized. More particularly, a layer (ketoamine oxidase layer 412) of the base material 414 containing the ketoamine oxidase 402 is formed on the hydrogen peroxide detection portion 403. A layer (protease layer 411) of the base material 404 containing the protease 401 is formed on the ketoamine oxidase layer 412, that is, on a surface opposite to the hydrogen peroxide detection portion 403. In other words, the ketoamine oxidase layer 412 and the protease layer 411 are laminated on the hydrogen peroxide detection portion 403 in this order.

In sensors of the present disclosure, the protease and the ketoamine oxidase may be laminated on the detection portion or may not be laminated. In some embodiments, the protease and the ketoamine oxidase may be disposed close to the detection portion and may be disposed in the vicinity of the detection portion.

In some embodiments, the thickness of the protease, the ketoamine oxidase or the enzyme layer may be smaller than or equal to a value of 100 μm, 50 μm, 20 μm, 10 μm, 1 μm, 500 nm, 300 nm, 250 nm, 200 nm, 100 nm, 50 nm, etc. In some embodiments, the thickness of the protease, the ketoamine oxidase, or the enzyme layer may be greater than or equal to 10 nm, 20 nm, 25 nm, 30 nm, 50 nm, 100 nm, etc.

A sensor according to some embodiments may be disposed such that a ketoamine oxidase portion surrounds a protease portion (enclosed type).

Figure 5:
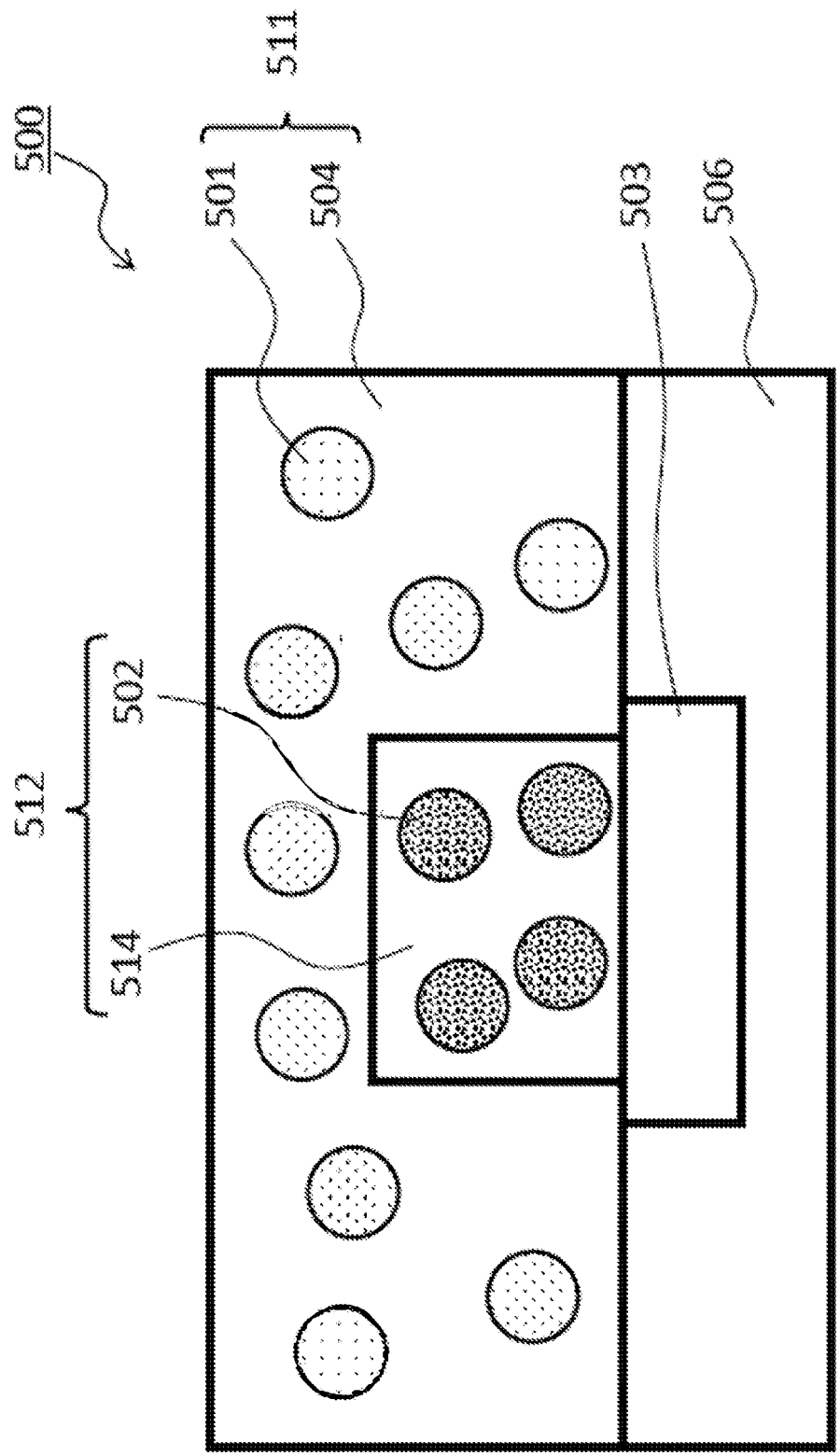
FIG. 5 illustrates a schematic cross-sectional view of a sensor according to an embodiment of the present disclosure.

FIG. 5 shows a structure of a sensor according to some embodiments (fifth embodiment). Sensor 500 has protease 501, ketoamine oxidase 502, base material 504,514 to which these are immobilized, hydrogen peroxide detection portion 503 to which the base material 514 is immobilized, and substrate 506. More particularly, the hydrogen peroxide detection portion 503 is provided to the substrate 506. The base material 514 (immobilized ketoamine oxidase portion 512) on which the ketoamine oxidase 502 is immobilized is formed on the hydrogen peroxide detection portion 503. The base material 504 (immobilized protease portion 511) to which the protease 501 is immobilized is formed so as to surround the immobilized ketoamine oxidase portion 512. In other words, the immobilized ketoamine oxidase portion 512 is disposed on the substrate 506 at a portion where the hydrogen peroxide detection portion 503 is substantially disposed, and the immobilized protease portion 511 is disposed so as to cover the immobilized ketoamine oxidase portion 512 and the surface of the substrate 506 without the hydrogen peroxide detection portion 503. By such a structure, it is possible to relatively increase the amount of immobilization of the protease in comparison with the amount of immobilization of the ketoamine oxidase. Thus, for example, when degradation or digestion by protease of a protein which is a large molecule becomes rate-limiting, the response rate, the detection sensitivity, and the like of the sensor can be improved.

The enzyme may be immobilized within a base material and immobilized on the outer surface of the base material (direct bonding type).

Figure 6:
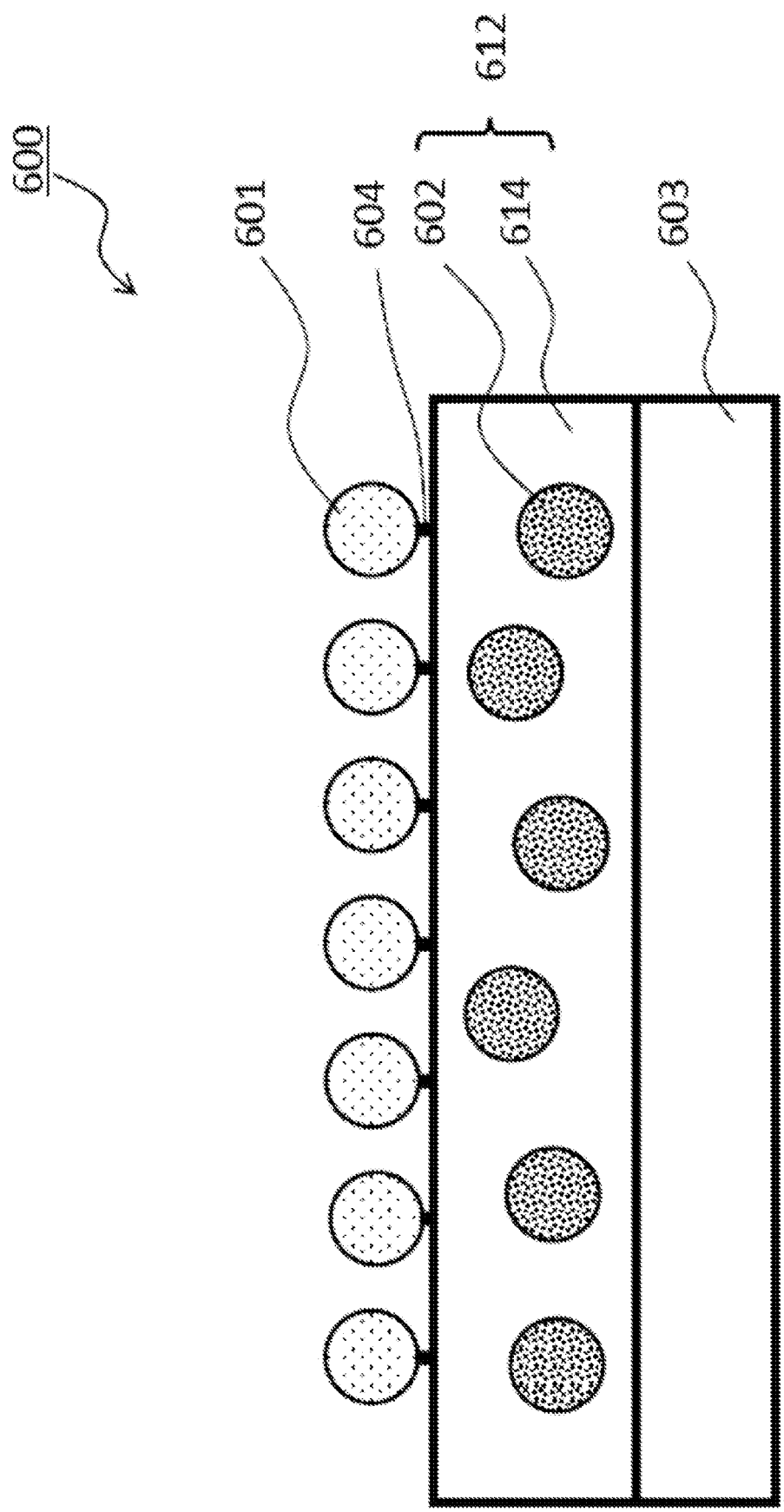
FIG. 6 illustrates a schematic cross-sectional view of a sensor according to an embodiment of the present disclosure.

Sensor 600 shown in FIG. 6 is of the direct bonding type and has protease 601, ketoamine oxidase 602 and hydrogen peroxide detection portion 603 to which these are immobilized. More particularly, base material 614 (ketoamine oxidase layer 612) having the ketoamine oxidase 602 immobilized thereon is formed on the hydrogen peroxide detection portion 603. The protease 601 is fixed to the upper surface of this ketoamine oxidase layer 612 by crosslinking agent 604. The protease 601 of FIG. 6 is immobilized to the base material 614. The protease 601 may be cross-linked to the ketoamine oxidase 602.

Figure 7:
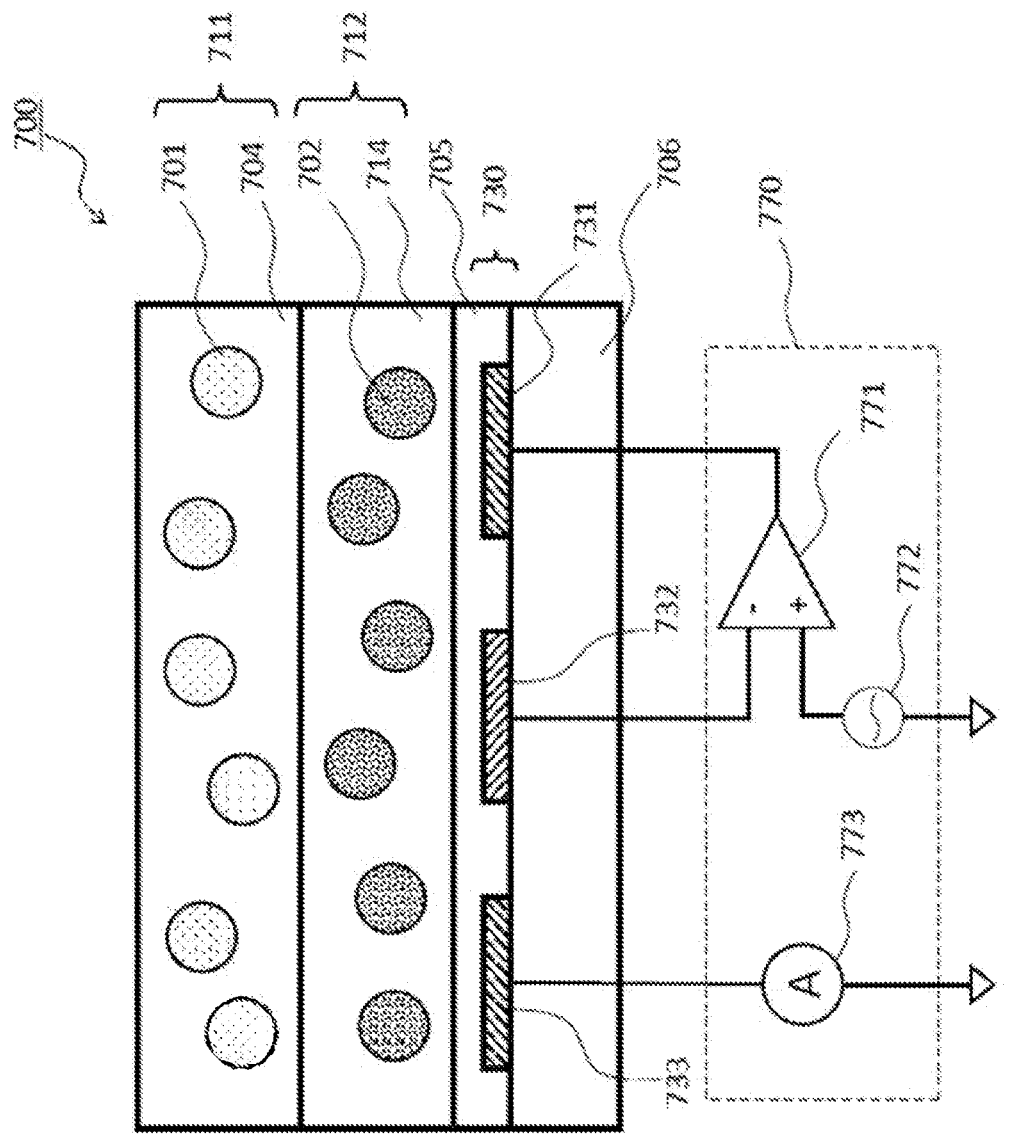
FIG. 7 illustrates a schematic cross-sectional view of a sensor according to an embodiment of the present disclosure.

FIG. 7 shows an example of a sensor structure having a hydrogen peroxide electrode. In FIG. 7, as an example of immobilization of protease and ketoamine oxidase, a laminated structure as in FIG. 4 is shown. However, aspects of the immobilization of the protease and the ketoamine oxidase are not limited thereto, and as described above exemplarily, a laminated structure or a structure other than FIG. 7 may be used, and a structure that is not laminated may be used.

Sensor 700 shown in FIG. 7 has hydrogen peroxide electrode 730 formed on insulating substrate 706, ketoamine oxidase 702 disposed on the hydrogen peroxide electrode 730, base material 714 (ketoamine oxidase layer 712) for immobilizing the same, protease 701 disposed on the ketoamine oxidase layer 712, and base material 704 (protease layer 711) for immobilizing the same. Silane coupling agent 705 for bonding the surface of the electrode 730 and the base material 714 is applied between the hydrogen peroxide electrode 730 and the ketoamine oxidase layer 712.

The hydrogen peroxide electrode 730 shown in FIG. 7 is an electrode for the three-electrode method, and includes counter electrode 731, reference electrode 732, and working electrode 733. The sensor 700 shown in FIG. 7 further includes electrical circuit 770 connected to the hydrogen peroxide electrode 730. The electrical circuit 770 includes operational amplifier 771, voltage generating circuit 772 and current measuring circuit 773. The output (OUT) of the operational amplifier is connected to the counter electrode 731, the inverting input (−IN) is connected to the reference electrode 732, and the non-inverting input (+IN) is connected to the voltage generating circuit 772.

The three-electrode method is a method in which a counter electrode, a reference electrode, and a working electrode are installed so as to be in contact with a solution or a body fluid, a predetermined potential difference is provided between the counter electrode and the working electrode, and a current flowing from the counter electrode to the working electrode is measured. Generally, when a substance such as a metal or a metal oxide enters an electrolytic solution, a potential difference called an interfacial potential occurs between the substance and the electrolytic solution. When a voltage is applied between the counter electrode and the working electrode while considering up to this potential difference, current flows from the counter electrode, and the potential difference between the counter electrode and the solution may change. Due to this change in potential difference, the desired voltage may not be accurately applied to the solution. In the three-electrode method, in order to avoid this, the reference electrode can measure the applied potential of the counter electrode and control the voltage applied to the counter electrode so that the potential is determined to the desired value. There is also a feedback circuit that feeds back the measured potential at the reference electrode to a circuit that controls the counter electrode.

2. Reduction of Noise Caused by Contaminants

Solutions may include contaminants. For example, when a protein in a body fluid is measured, measurement noise is generated by various contaminants such as proteins, peptide fragments, nucleic acids, and ions other than the protein to be measured. Noise due to these contaminants causes measurement faults and measurement errors. Thus, a sensor according to some embodiments of the present disclosure may have a configuration that reduces the impact of contaminants on the measurement signal.

<Noise Reduction Using Ion Exchange Resin>

A sensor according to some embodiments may have an ion exchange resin on the detector.

Figure 8:
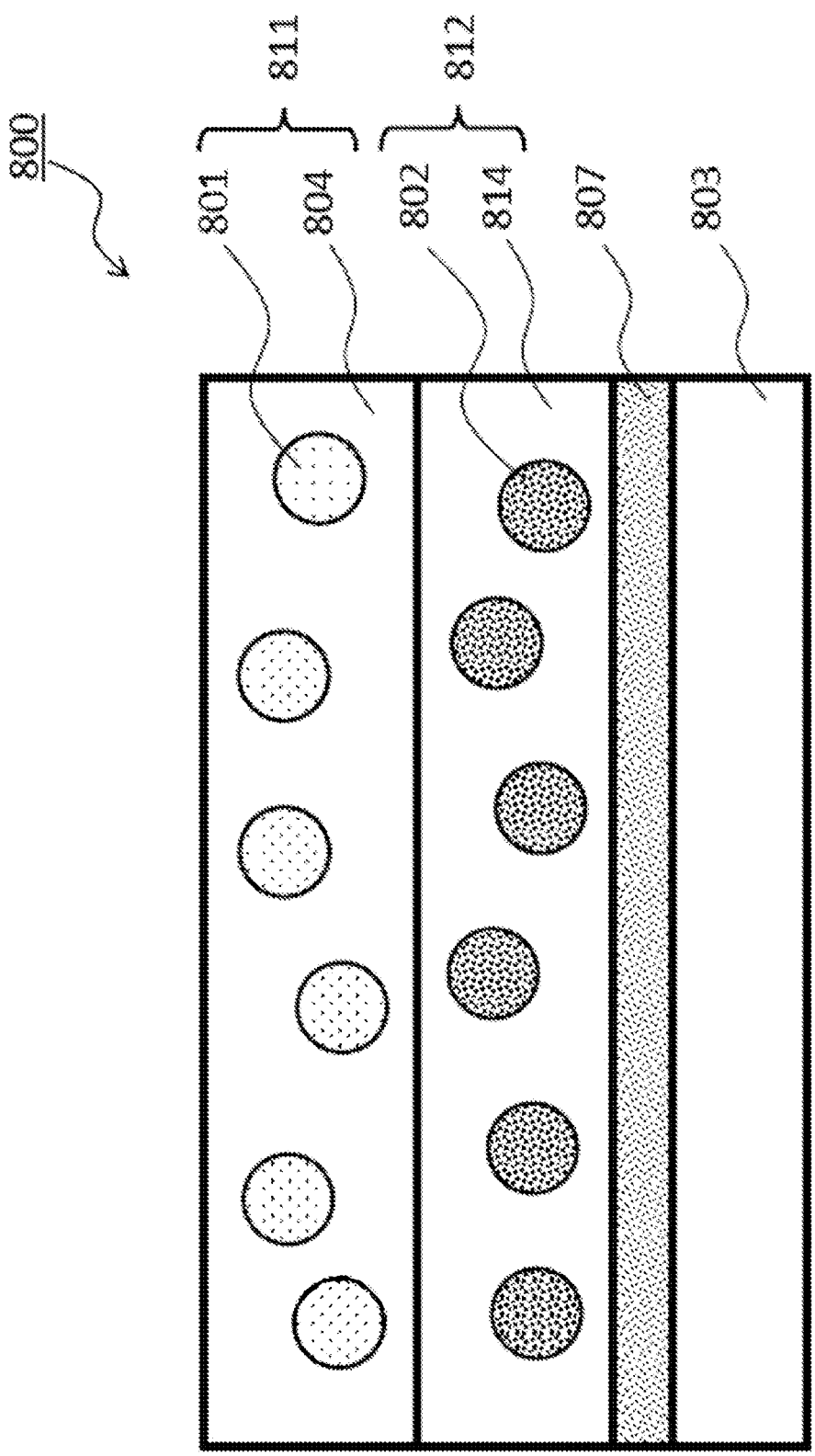
FIG. 8 illustrates a schematic cross-sectional view of a sensor according to an embodiment of the present disclosure.

Sensor 800 shown in FIG. 8 has hydrogen peroxide electrode 803, ketoamine oxidase 802 disposed on the hydrogen peroxide electrode 803, base material 814 (ketoamine oxidase layer 812) that immobilizes it, and protease 801 disposed on the ketoamine oxidase layer 814 and base material 804 (protease layer 811) that immobilizes it. The sensor 800 shown in FIG. 8 further includes ion exchange resin 807 between the ketoamine oxidase layer 812 and the hydrogen peroxide electrode 803.

For example, a cation exchange resin such as Nafion (registered trademark) can be used to inhibit or prevent ascorbic acid or uric acid, particularly negative ions, and the like, present in the body fluid from permeating and reaching the detection portion. For example, an anion exchange resin such as polypyrrole can be used to inhibit or prevent dopamine and the like, particularly plus ions, from permeating and reaching the detection portion.

The ion exchange resin may include one, a plurality or at least one kind of ion exchange resins. The ion exchange resin may be configured to have one, a plurality or at least one type of layers.

In FIG. 8, as an example of immobilization of protease and ketoamine oxidase, a laminated structure as in FIG. 4 is shown. However, the aspects of the immobilization of the protease and the ketoamine oxidase are not limited thereto, and as described above exemplarily, a laminated structure or a structure other than FIG. 8 may be used, and a structure that is not laminated may be used.

<Noise Reduction by Difference Sensor>

Sensors according to some embodiments may be a pair or set of differential or difference sensors. The sensors may include a plurality of pairs or sets of differential or difference sensors. The set of difference sensors included in the difference type sensor may be configured to include a main sensor and a sub-sensor. The main sensor includes an immobilized protease, an immobilized ketoamine oxidase, and a detection portion. The sub-sensor is insensitive to the main substance to be measured (test substance) detected by the main sensor, but has substantially the same or similar sensitivity as the main sensor to the molecules causing noise.

As an example of the sensor, a sensor for measuring glycated proteins in body fluids will be considered. The body fluid contains proteins, peptides, vitamin C, ions, and the like other than the protein which is the test substance. Peptide fragments, for example, are recognized by ketoamine oxidase, which becomes a cause to generate hydrogen peroxide. Also, ions in body fluids can be detected by a hydrogen peroxide detection portion.

Thus, the sub-sensor may be a sensor in which the noise sources including them are detected in a manner that is approximately the same as or of some relevance to the main sensor. The sub-sensor, for example, does not contain a protease (protease-free) for the main sensor and may have almost the same other structure. For example, in the sub-sensor, the surface area and the height, dimensions of a portion containing the base material and the enzyme, the type of the base material, the manufacturing method, and the like may be substantially the same as those of the main sensor. Materials, structures, manufacturing methods, and the like other than the proteases of the main sensor and the sub-sensor may not be the same. In this case, it is only necessary to obtain the mutual relevance by calibration or the like.

In some embodiments, the hydrogen peroxide detector in both or one of the main and sub-sensors of the difference sensor may be covered with an ion exchange resin, and a layer or membrane of ion exchange resin may be disposed on the surface of the hydrogen peroxide detector.

In some embodiments, the configuration of the main sensor may be of the enzyme layer integrated type, e.g., as in FIG. 3.

Figure 9:
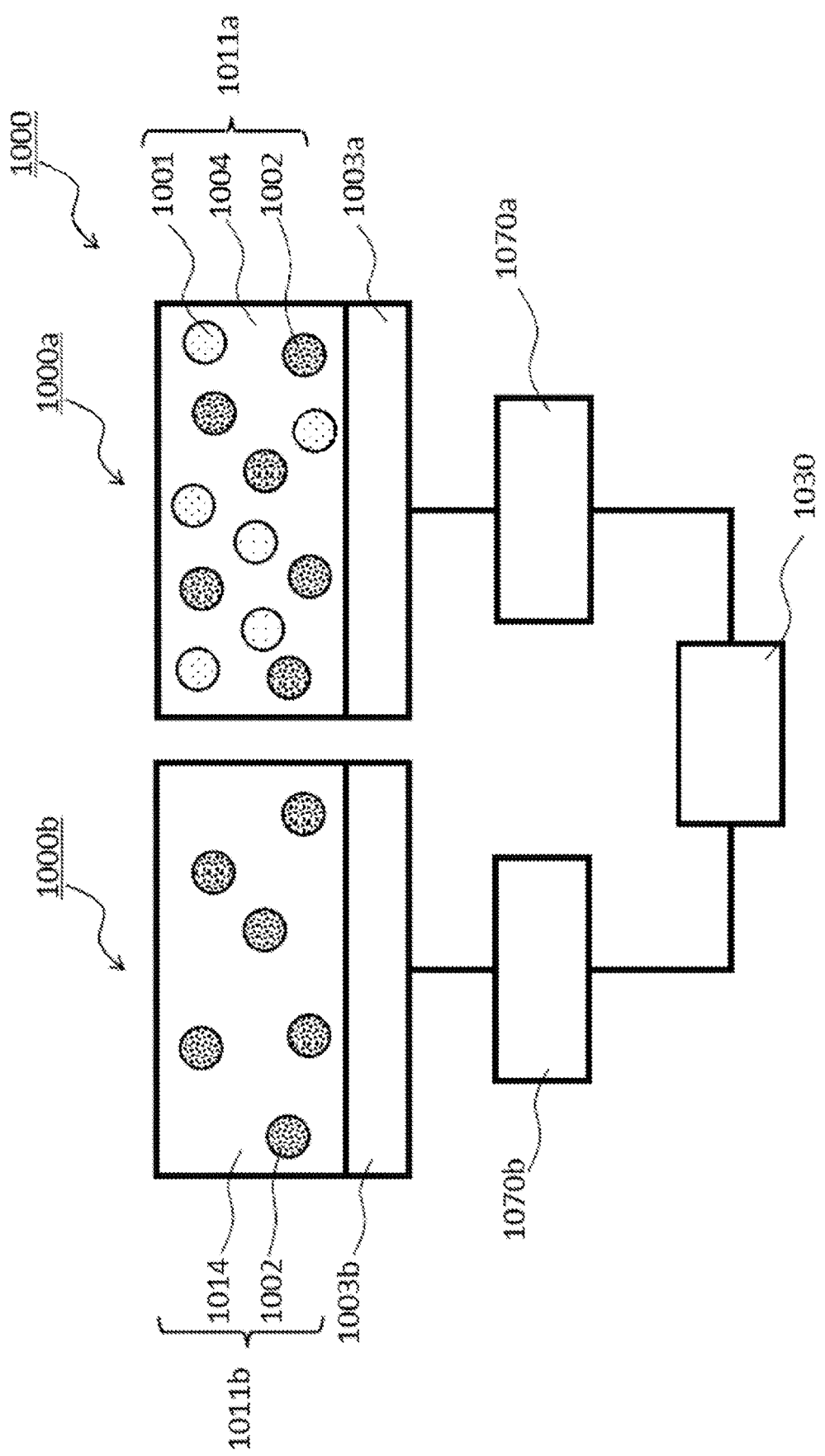
FIG. 9 illustrates a schematic cross-sectional view of a sensor according to an embodiment of the present disclosure.

Sensor 1000 according to FIG. 9 includes main sensor 1000a of the enzyme layer integrated type and sub-sensor 1000b.

The main sensor 1000a shown in FIG. 9 is an enzyme layer integrated type as shown in FIG. 2 or FIG. 3. Specifically, the main sensor 1000a has protease 1001, ketoamine oxidase 1002, base material 1004 on which these are immobilized, and hydrogen peroxide detection portion 1003a to which the base material 1004 is immobilized. In the main sensor 1000a shown in FIG. 9, the same base material 1004 is formed as a layer or a film on the hydrogen peroxide detection portion 1003a, and an enzyme layer 1011a to which the protease 1001 and the ketoamine oxidase 1002 are immobilized to the base material 1004 is formed on the hydrogen peroxide detection portion 1003a. The enzyme molecules of the protease 1001 and the ketoamine oxidase 1002 are immobilized in this same base material 1004.

On the other hand, the sub-sensor 1000b shown in FIG. 9 does not include the protease 1001 in substantially the same configuration as the main sensor 1000a. Specifically, the sub-sensor 1000b includes the ketoamine oxidase 1002, base material 1014, and hydrogen peroxide detection portion 1003b similar to the main sensor 1000a. The enzyme layer 1011b of the sub-sensor 1000b having the ketoamine oxidase 1002 and the base material 1014 may have substantially the same dimensions as the enzyme layer 1011a of the main sensor.

The hydrogen peroxide detectors 1003a, 1003b of the main sensor 1000a and the sub-sensor 1000b are connected to measurement electric circuits 1070a, 1070b, respectively. These electric circuits 1070a, 1070b receive output signals such as currents from the respective hydrogen peroxide detectors 1003a, 1003b, convert the values into digital values, and send the converted values to operation part 1030 such as a CPU. In some embodiments, the transmission from the electrical circuits 1070a, 1070b to the operation part 1030 may be electrical, optical, wired, or wireless.

The operation part 1030 may perform calculations such as a difference between the signals from the main sensor 1000a and the sub-sensor 1000b. By removing an output corresponding to noise such as a contaminant from the output signal of the main sensor 1000a on the basis of the signal from the sub-sensor 1000b, it is possible to detect the signal of the measurement target substance with higher accuracy. The operation part 1030 may further include a transmission unit (not shown) or may be connected to an external transmission unit (not shown). The transmitter may transmit the signal optically, electrically or electromagnetically, wiredly or wirelessly. The signal to be transmitted may be a signal after performing the difference operation in the operation part 1030. In another embodiment, the transmitter may individually transmit signals from the main sensor 1000a and the sub-sensor 1000b. A calculation such as a difference may be performed at the transmission destination. The configuration or function of these operation part is not limited to the present embodiment, and may be applied to other embodiments. The operation part may include a storage medium therein, and may be connected to or connected to a storage medium disposed outside the operation part.

The configuration of the main sensor in the difference type sensor may be, for example, a laminated type as shown in FIG. 4.

Figure 10:
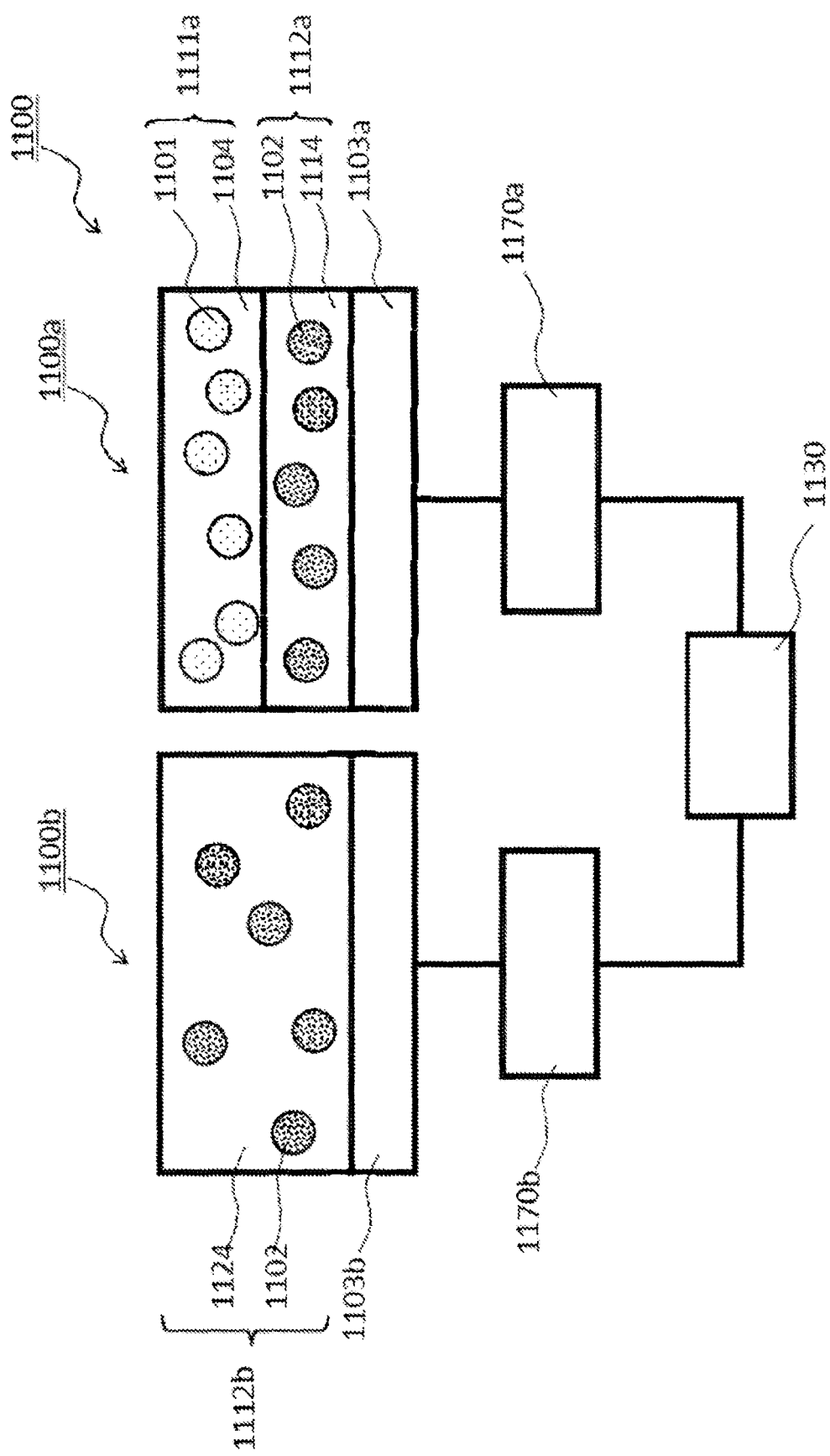
FIG. 10 illustrates a schematic cross-sectional view of a sensor according to an embodiment of the present disclosure.

Sensor 1100 shown in FIG. 10 includes laminated-type main sensor 1100a and sub-sensor 1100b.

The main sensor 1100a shown in FIG. 10 is of a laminated type as shown in FIG. 4. The main sensor 1100a shown in FIG. 10 has protease 1101, ketoamine oxidase 1102, base material 1104, 1114 to which these are immobilized, and hydrogen peroxide detection portion 1103a to which the base material 1114 is immobilized. More particularly, a layer (ketoamine oxidase layer 1112a) of the base material 1114 containing the ketoamine oxidase 1102 is formed on the hydrogen peroxide detection portion 1103a. On the ketoamine oxidase layer 1112a, that is, on the surface opposite to the hydrogen peroxide detection portion 1103a, a layer of the base material 1104 containing the protease 1101 (protease layer 1111a) is formed. In other words, the ketoamine oxidase layer 1112a and the protease layer 1111a are laminated on the hydrogen peroxide detection portion 1103a in this order.

In some embodiments, different materials may be used for the base material at each layer. For example, a base material containing a protein as a main component may be used for the ketoamine oxidase layer, and a base material containing a photocrosslinkable resin as a main component may be used for the protease layer.

On the other hand, the sub-sensor 1100b shown in FIG. 10 has substantially the same configuration as the main sensor 1100a and does not include or is free of the protease 1101 or its base material 1104. Specifically, the sub-sensor 1100b has ketoamine oxidase 1102 similar to that of the sensor 1100a, base material 1124, and hydrogen peroxide detection portion 1103b. The enzyme layer 1112b of the sub-sensor 1100b having the ketoamine oxidase 1102 and the base material 1124 may be approximately the same size as the entire enzyme layer 1111a, 1112b of the main sensor.

The thickness of the enzyme layer may be different between the main sensor and the sub-sensor. In some embodiments, the thickness of the ketoamine oxidase layer of the sub-sensor may be the same as the thickness of the ketoamine oxidase layer of the main sensor. The film thickness of each sensor may be adjusted based on correlations such as signal intensities obtained using the same or different calibration solutions. The concentration and the total amount of the enzyme may be the same between the main sensor and the sub-sensor, and may be different and may be adjusted depending on the sensor. The material of the base material may also be the same or different between the main sensor and the sub-sensor.

The hydrogen peroxide detectors 1103a, 1103b of the main sensor 1100a and the sub-sensor 1100b are connected to measurement electric circuits 1170a, 1170b, respectively. The electric circuits 1170a, 1170b receive output signals such as currents from the hydrogen peroxide detectors 1103a, 1103b, and digitally transmit the values to operation part 1130 such as a CPU.

In some embodiments, the configuration of the main sensor in the difference type sensor may be of an enclosed type, e.g., as in FIG. 5.

In some embodiments, the configuration of the main sensor in the difference type sensor may be a direct bonding type, for example, as in FIG. 6.

Figure 11:
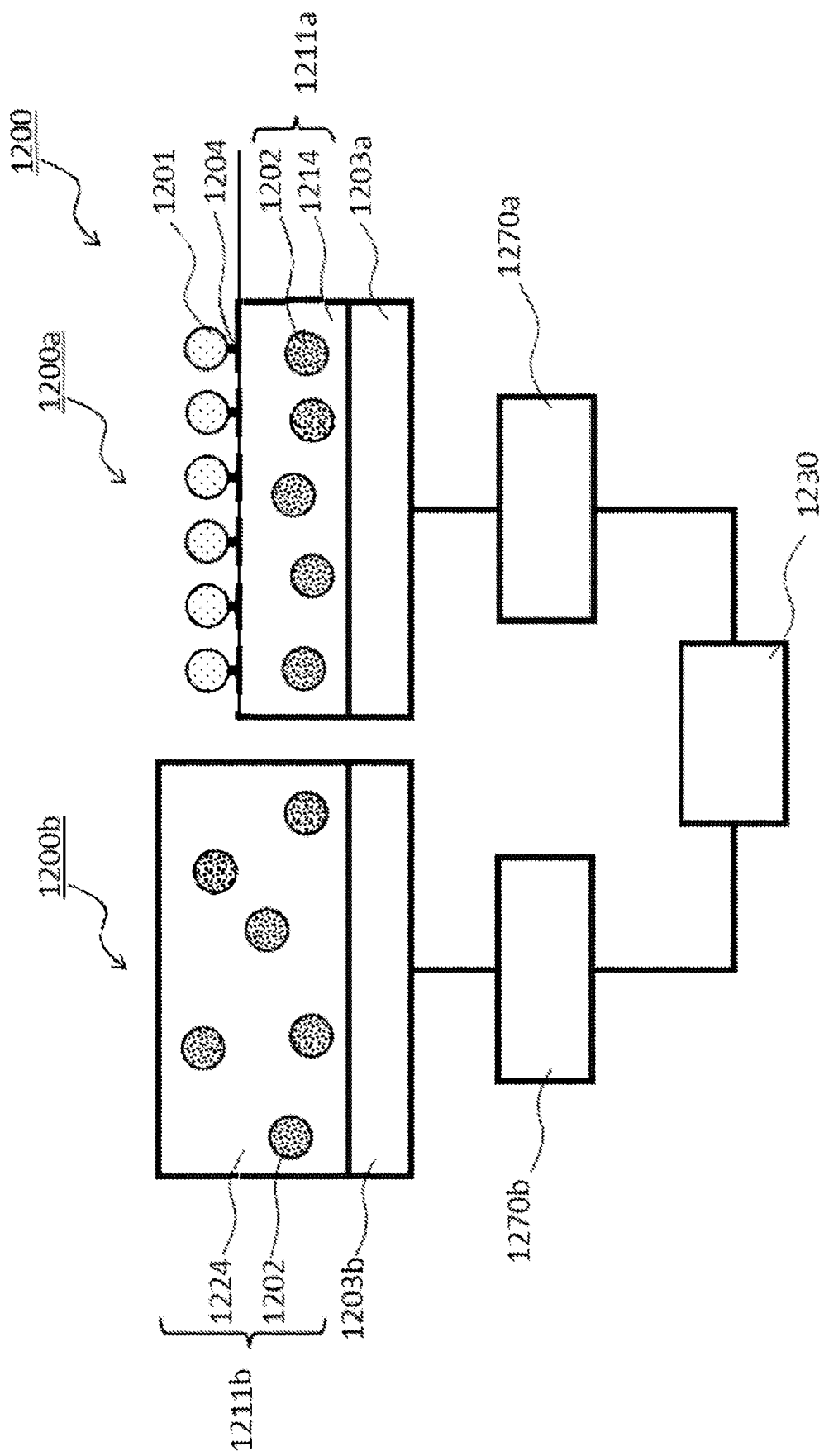
FIG. 11 illustrates a schematic cross-sectional view of a sensor according to an embodiment of the present disclosure.

The sensor 1200 shown in FIG. 11 includes direct bonding type of main sensor 1200a and sub-sensor 1200b.

The main sensor 1200a shown in FIG. 11 is a direct bonding type sensor as shown in FIG. 4, and includes protease 1201, ketoamine oxidase 1202, and hydrogen peroxide detection portion 1203a on which these are immobilized. More particularly, base material 1214 (ketoamine oxidase layer 1212a) having the ketoamine oxidase 1202 immobilized thereon is formed on the hydrogen peroxide detection portion 1203a. The protease 1201 is immobilized to the upper surface of the ketoamine oxidase layer 1212a by crosslinking agent 1204. The protease 1201 of FIG. 11 is immobilized to the base material 1214. The protease 1201 may be cross-linked to the ketoamine oxidase 1202.

On the other hand, the sub-sensor 1200b shown in FIG. 11 does not contain or is free of protease 1201. Specifically, the sub-sensor 1200b includes ketoamine oxidase 1202, base material 1224, and hydrogen peroxide detection portion 1203b similar to the main sensor 1200a. In other words, enzyme layer 1212b containing the ketoamine oxidase 1202 and the base material 1224 is configured on the hydrogen peroxide detection portion 1203b.

In the main sensor 1200a, the protease 1201 is directly bonded on the ketoamine oxidase layer 1212a. In contrast, the uppermost surface of the sub-sensor 1200b may be substantially comprised of the base material 1224. Accordingly, it is considered that the main sensor 1200*a* and the sub-sensor 1200*b* are not necessarily the same or may be different in characteristics such as permeability of molecules or ions to the inside of the base material at the outermost surface. Therefore, the configuration of the enzyme layer 1212*b* of the sub-sensor 1200*b*, e.g., thickness, type of the base material 1224, the concentration of the ketoamine oxidase 1202, the manufacturing method, etc., may be relatively adjusted such that the characteristics of the main sensor 1200*a* and the sub-sensor 1200*b* are substantially the same or related.

The hydrogen peroxide detectors 1203*a*, 1203*b* of the main sensor 1200*a* and the sub-sensor 1200*b* are connected to measurement electric circuits 1270*a*, 1270*b*, respectively. The electric circuits 1270*a*, 1270*b* receive output signals such as currents from the hydrogen peroxide detectors 1203*a*, 1203*b*, and digitally transmit the values to operation part 1230 such as a CPU.

The main sensor and the sub-sensor of the difference type sensor may each include a hydrogen peroxide electrode in the hydrogen peroxide detection portion. For example, the hydrogen peroxide electrode 730 and the electric circuit 770 shown in FIG. 7 may be disposed in the main sensor, and the hydrogen peroxide electrode and the electric circuit having the same or relatively different configurations may be disposed in the sub-sensor.

The main sensor and the sub-sensor of the difference sensor may share a part of the configuration of the hydrogen peroxide detection portion. For example, when a hydrogen peroxide electrode is disposed in the hydrogen peroxide detection portion, the working electrode may be disposed in each sensor, and the counter electrode and the reference electrode may be disposed in one of the sensors and shared.

Figure 12:
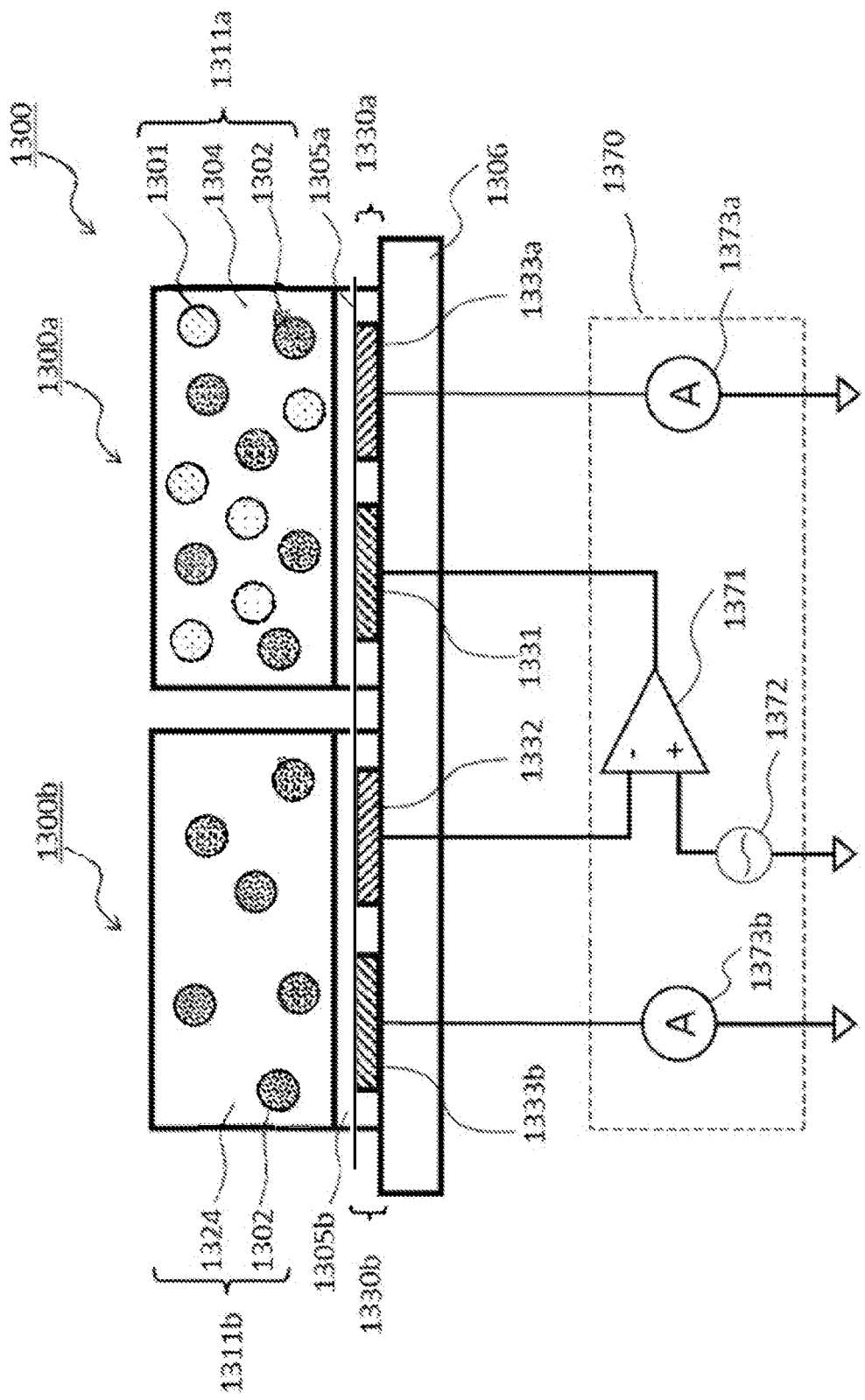
FIG. 12 illustrates a schematic cross-sectional view of a sensor according to an embodiment of the present disclosure.

In the difference sensor 1300 shown in FIG. 12, main sensor 1300*a* and sub-sensor 1300*b* are disposed on substrate 1306.

In the main sensor 1300*a* shown in FIG. 12, enzyme layer 1311*a* is disposed on hydrogen peroxide electrode 1330*a* via silane coupling agent 1305*a*. The enzyme layer 1311*a* contains protease 1301 and ketoamine oxidase 1302 in base material 1304. In the sub-sensor 1300*b* shown in FIG. 12, enzyme layer 1311*b* is disposed on hydrogen peroxide electrode 1330*b* via silane coupling agent 1305*b*. The enzyme layer 1311*b* does not contain the protease 1301 and contains the ketoamine oxidase 1302 in the base material 1324.

The hydrogen peroxide electrode 1330*a* of the main sensor 1300*a* includes working electrode 1333*a* for the main sensor and the counter electrode 1331. On the other hand, the hydrogen peroxide electrode 1330*b* of the sub-sensor 1300*b* includes working electrode 1333*b* for the sub-sensor and reference electrode 1332. These electrodes are connected to electrical circuit 1370.

In other words, the hydrogen peroxide electrodes 1330*a*, 1330*b* shown in FIG. 12 are electrodes for the three-electrode method, and the working electrodes 1333*a*, 1333*b* are disposed in the main sensor 1300*a* and the sub-sensor 1300*b*, respectively. On the other hand, the counter electrode 1331 and the reference electrode 1332 are disposed only in one of the main sensor 1300*a* and the sub-sensor 1300*b*.

The sensor 1300 shown in FIG. 12 further includes electrical circuit 1370 connected to the hydrogen peroxide electrodes 1330*a*, 1330*b*. The electric circuit 1370 includes operational amplifier 1371, voltage generation circuit 1372, and current measurement circuits 1373*a*, 1373*b* connected to the main sensor 1300*a*, the sub-sensor 1300*b*, respectively. The output (OUT) of the operational amplifier is connected to the counter electrode 1331, the inverting input (−IN) is connected to the reference electrode 1332, and the non-inverting input (+IN) is connected to the voltage generating circuit 1372.

At the time of measurement, a solution (not shown) containing a test substance (a substance to be measured, a substance to be measured) comes into contact with both the main sensor 1300*a* and the sub-sensor 1300*b*. Therefore, the counter electrode 1331 can apply a desired voltage to both the main sensor working electrode 1333*a* and the sub-sensor working electrode 1333*b* while generating a constant potential difference with respect to the potential of the reference electrode 1332. Current measurement circuits 1373*a*, 1373*b* detect output signals from the main sensor 1300*a* and the sub-sensor 1300*b*, respectively, and provide output signals to the outside (not shown). With such a configuration, the area of the electrode can be reduced, and the size of the sensor and the device can be miniaturized.

The enzyme layer of the main sensor 1300*a* of FIG. 12 has an integral type structure as shown in FIG. 2, but is not limited thereto. The sub-sensor 1300*b* of FIG. 12 is not limited to the same. The main sensor 1300*a* and the sub-sensor 1300*b* may be configured in any other manners.

In FIG. 12, the current measurement circuits 1373*a*, 1373*b* are arranged to the main sensor 1300*a* and the sub-sensor 1300*b*, respectively, but the present invention is not limited to this configuration. One current measurement circuit and a switching circuit may be arranged, and signals from the main sensor working electrode 1333*a* and the sub-sensor working electrode 1333*b* may be provided to the current measurement circuit and detected or measured at alternating or predetermined timings by using the switching circuit.

The protease, the ketoamine oxidase and the detection portion may not be arranged at the same location or in close proximity, such as by lamination. In some embodiments, ketoamine oxidase and a detection portion are laminated or arranged in proximity with each other, and protease may be arranged apart from these. In another embodiment, the protease, the ketoamine oxidase and the detection portion may be arranged apart from each other. By immobilizing and arranging proteases apart from other components, various conditions, including the time and temperature of the degradation reaction by the protease may be made efficient or optimized. After a sufficient protease degradation reaction, the product of the reaction, peptide fragments, can be passed to the ketoamine oxidase.

In some embodiments, the protease, the ketoamine oxidase, and the detection portion may be arranged in the order of the protease, the ketoamine oxidase, and the detection portion from upstream or from upstream to downstream of the solution, or in other words, according to the direction of introduction of the solution or the order of reaction. Thus, the reaction product in each reaction can be efficiently conveyed to the next reaction.

In some embodiments, the protease and the ketoamine oxidase and the detection portion may be contained in a container portion (chamber) defined in each. Each reaction occurs in the corresponding container portion and one reaction can be carried out separately from another. Thus, it is possible to reduce the limitation and the influence from the conditions and the preparation conditions of the other reaction, and to efficiently perform the desired reaction. For example, taking sufficient time to degrade the glycated protein to peptide fragments with protease, and after a desired time, the peptide fragments can be sent to the ketoamine oxidase.

Figure 13:
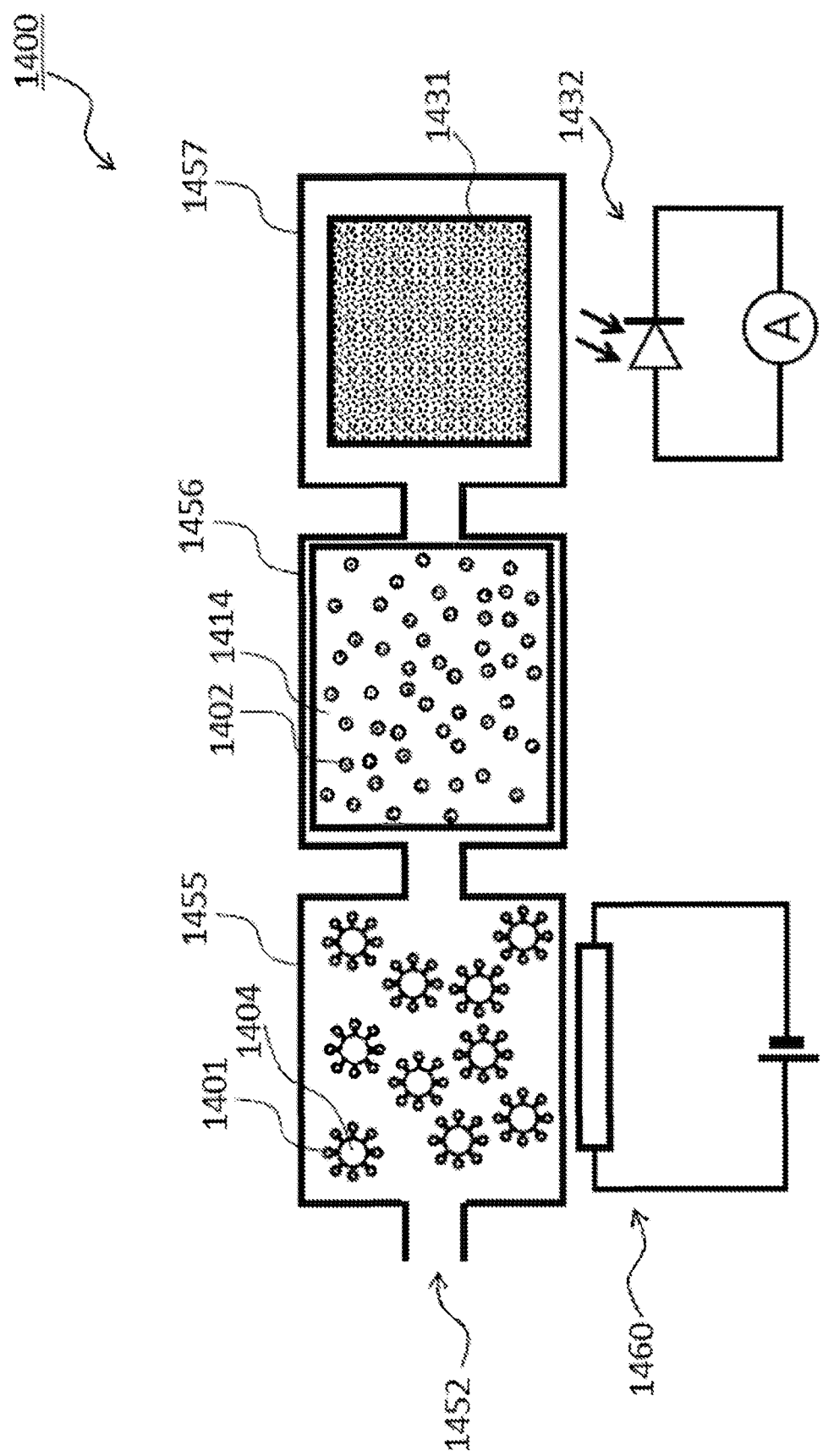
FIG. 13 illustrates a schematic configuration of a sensor according to an embodiment of the present disclosure.

In sensor 1400 shown in FIG. 13, the protease and the ketoamine oxidase and the detection portion are arranged apart from each other. In addition, the protease, the ketoamine oxidase and the detection portion are arranged in the order of the protease, the ketoamine oxidase and the detection portion from the upstream side to the downstream side according to the direction of the introduction direction of the solution or the order of the reaction. Further, the protease, the ketoamine oxidase and the detection portion are contained in a container portion (chamber) defined in each of them and fluidly connected to each other.

FIG. 13 will be described in more detail. The liquid that entered from the liquid inlet 1452 enters the protease container portion 1455. The liquid may enter the liquid inlet 1452 through the flow path. The liquid may be delivered to the solution inlet 1452 by capillary action. In the protease container portion 1455, protease 1401 is accommodated in a state of being immobilized to the beads 1404. In some embodiments, beads 1404 may be immobilized to an inner wall of the container portion 1455. In another embodiment, the beads 1404 may not be immobilized directly relative to the container portion 1455. For example, by narrowing the width of the flow path with respect to the sufficiently large beads 1404, the beads 1404 are substantially in a state of being immobilized in the container portion 1455.

Heater 1460 is disposed to the protease container portion 1455 shown in FIG. 13. The heater 1460 may heat or control the temperature of the solution or the protease 1401 in the protease container portion 1455 to increase the rate of degradation by the protease and the like, and thus the reaction can be made efficient or optimized. Although the electric heater is described in FIG. 13 it is not limited thereto. A heating method other than electricity may be employed for the heater. In another embodiment, a temperature regulator may be disposed.

In some embodiments, the temperature of the protease may be controlled. In some embodiments, the temperatures of the protease, and the ketoamine oxidase, may be controlled together or individually. In some embodiments, the temperatures of some or all of the sensors or sensor chips may be controlled. In some embodiments, the temperature of the protease container portion may be controlled. The heating time and temperature profile of the protease and the like may be controlled.

In some embodiments, the temperature of the protease may be at or higher than any one of 20° C., 25° C., 30° C., 35° C., 40° C., 45° C., 50° C., 55° C., and 60° C. In some embodiments, the temperature of the protease may be at or lower than any one of 80° C., 75° C., 70° C., 65° C., 60° C., 55° C., 50° C., 45° C., 40° C., and 35° C. In some embodiments, the temperature of the protease may be in the range of the optimum temperature of the protease. In some embodiments, the temperature of the protease may be lower than the temperature at which it deactivates.

In the protease container portion 1455, the generated peptide fragments are conveyed to the ketoamine oxidase container portion 1456 in which the ketoamine oxidase 1402 is immobilized to the base material 1414.

In some embodiments, the transfer of the protease in a solution state from the protease containing part 1455 to the ketoamine oxidase containing part 1456 may be performed by capillary action. For example, by selecting or adjusting the shape such as a cross-sectional area or the distance between each container portion and the flow path, the material such as hydrophilicity or hydrophobicity of the inner wall, or the like, the stagnation time of the protease in a solution state in the protease container portion 1455, the timing of liquid delivery to the ketoamine oxidase container portion 1456, or the like can be adjusted.

In some embodiments, the protease container portion 1455 may be configured in a volumetrically changeable manner with a flexible or elastic material such as silicone, and deformed by applying pressure from the outside at a predetermined timing, thereby discharging the liquid from the protease container portion 1455. In doing so, the liquid inlet 1452 may be configured to be closed so that the liquid does not flow back to the liquid inlet 1452.

In the ketoamine oxidase container portion 1456, the ketoamine oxidase 1402 is immobilized to the base material 1414. In FIG. 13, the base material 1414 and the ketoamine oxidase 1402 are formed as an immobilization layer in the ketoamine oxidase container portion 1456. The peptide fragments conveyed into the ketoamine oxidase container portion 1456 react with the ketoamine oxidase 1402 to generate hydrogen peroxide as a result.

In some embodiments, the temperature of the ketoamine oxidase may be controlled. In some embodiments, the temperature of the ketoamine oxidase container portion may be controlled. In some embodiments, the respective temperature may be controlled such that the temperature of the protease and the temperature of the ketoamine oxidase are different. In some embodiments, the temperature of the protease may be controlled to be higher than the temperature of the ketoamine oxidase, or the temperature of the ketoamine oxidase may be controlled to be lower than the temperature of the protease. In some embodiments, temperature control of the protease and the temperature control of the ketoamine oxidase may be performed simultaneously, may be performed in different time zones, or may be performed so that some time zones overlap. In some embodiments, the heating time and the temperature profile of the ketoamine oxidase and the like may be controlled.

In some embodiments, the controlled temperature of the ketoamine oxidase may be at or higher than any one of 10° C.° C., 12° C., 15° C., 20° C., 25° C., 30° C., 35° C. and 37° C. In some embodiments, the controlled temperature of the ketoamine oxidase may be at or lower than any one of 70° C., 60° C., 55° C., 50° C., 45° C., 40° C., 37° C. and 35° C. The temperature control of the ketoamine oxidase may be performed by heating, cooling, or a combination of heating and cooling.

In some embodiments, the ketoamine oxidase may be maintained at room temperature at the time of measurement. In some embodiments, the temperature of the ketoamine oxidase at the time of measurement may be measured to perform temperature correction on the result by the detector. For example, measurements may be performed while keeping the ketoamine oxidase at room temperature, and a temperature correction may be performed with respect to the measurement result. In some embodiments, the temperature of the protease at the time of measurement or upon peptide fragmentation may be measured to perform temperature correction with respect to the result by the detector. In some embodiments, a temperature correction may be performed on the measurement results based on the temperature of the protease at the time of measurement or upon peptide fragmentation and the temperature of the ketoamine oxidase at the time of measurement. Exemplarily, by performing temperature correction, it is possible to simplify the temperature control of at least one of the ketoamine oxidase and the protease. Thus, for example, the power source can be a battery and the sensor configuration can be miniaturized.

Hydrogen peroxide is conveyed to the detection reactor 1457 and detected by the detector 1432. In FIG. 13, reagent 1431 containing luminol is disposed inside the detection reactor 1457, and photodetector (photodiode) 1432 is disposed outside to detect light emission due to the luminol reaction.

The ketoamine oxidase may not be immobilized to the base material within the immobilization layer. The ketoamine oxidase may be immobilized to the beads.

Figure 14:
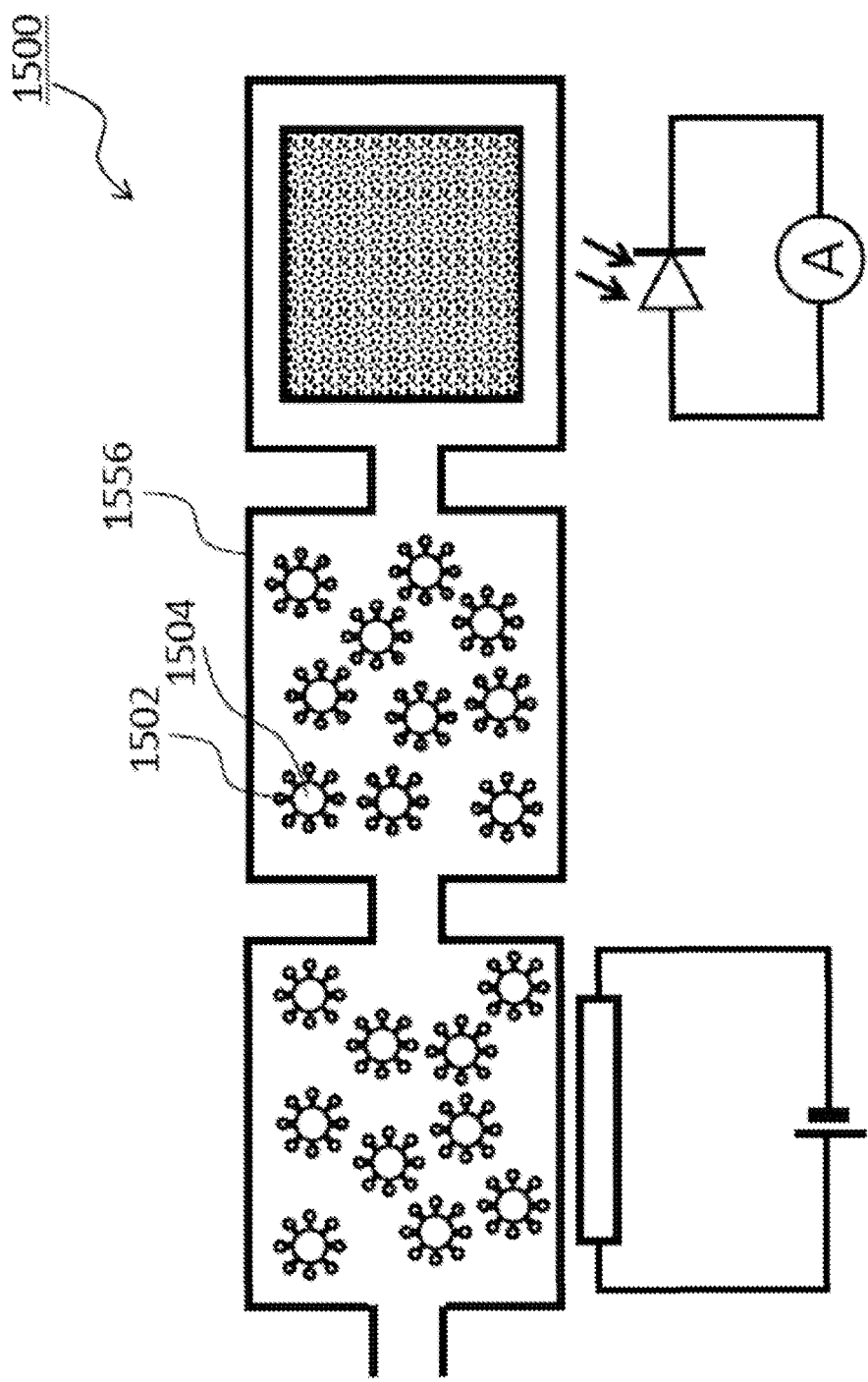
FIG. 14 illustrates a schematic configuration of a sensor according to an embodiment of the present disclosure.

In sensor 1500 shown in FIG. 14, although partially similar to the configuration of the sensor 1400 shown in FIG. 13, the ketoamine oxidase 1502 is immobilized to the beads 1504 and contained within the ketoamine oxidase containing part 1556.

In the sensor 1400 shown in FIG. 13 and the sensor 1500 shown in FIG. 14, the detector is configured to have a reagent for luminol reaction and a photodetector for detecting light emission. However, in a similar configuration, the detector may be another detector.

Other photodetectors may be used as the detector, and a hydrogen peroxide electrode may be used.

In some embodiments, the ketoamine oxidase and the hydrogen peroxide detector may be brought into contact or proximity, and the proteases may be arranged apart therefrom. Arranging the ketoamine oxidase in close proximity with the hydrogen peroxide detector is one way to reduce the effect of noise factors detected by the hydrogen peroxide detector or to improve the detection sensitivity of hydrogen peroxide.

Figure 15:
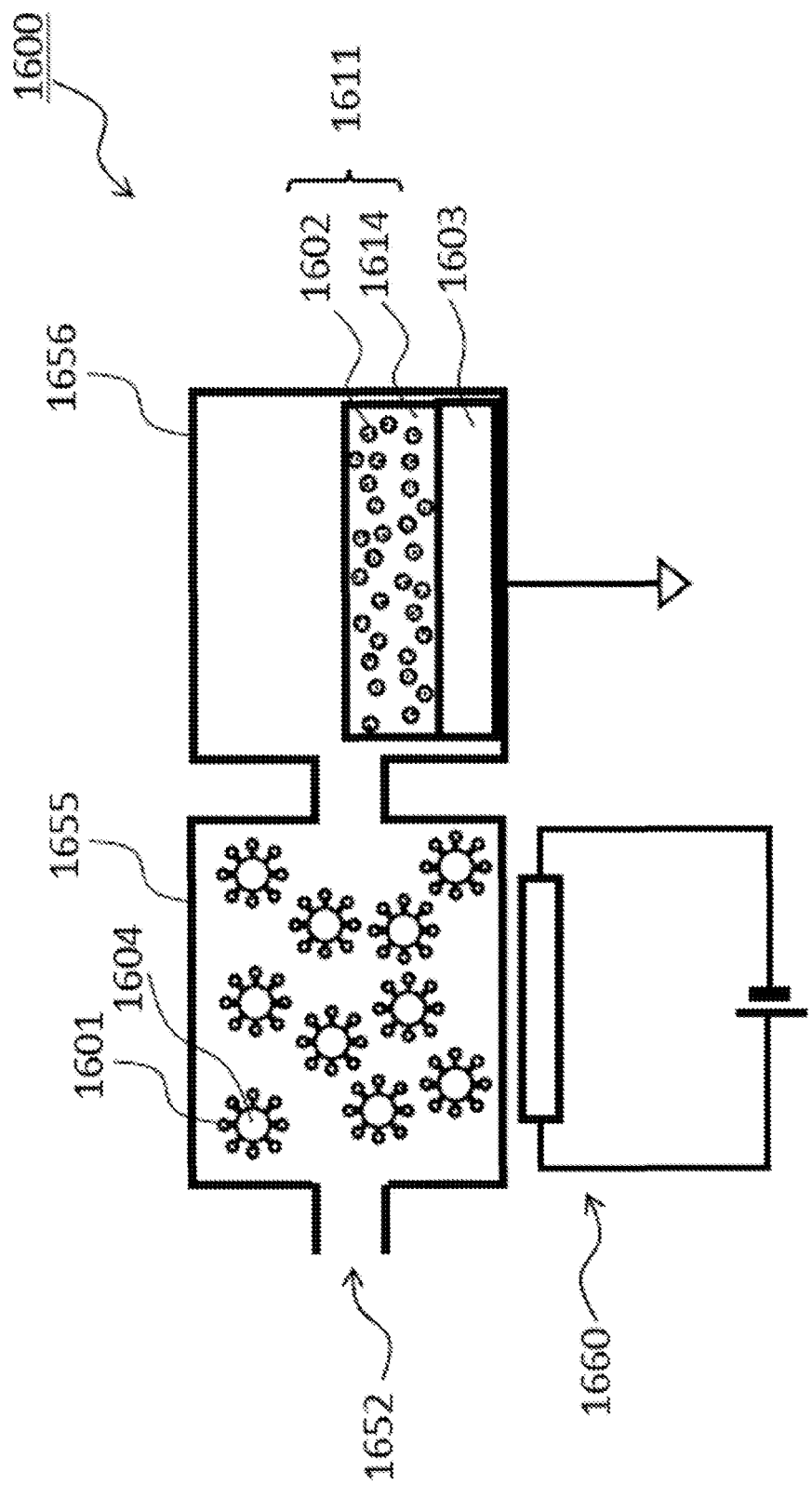
FIG. 15 illustrates a schematic configuration of a sensor according to an embodiment of the present disclosure.

In the sensor 1600 shown in FIG. 15, ketoamine oxidase 1602 is immobilized proximate to hydrogen peroxide detector 1603 and protease 1601 is arranged apart therefrom.

The liquid that entered from liquid inlet 1652 enters the protease container portion 1655. In the protease container portion 1655, the protease 1601 is contained in a state of being immobilized to the beads 1604.

Heater 1660 is disposed to the protease container portion 1655 shown in FIG. 15. The heater 1660 may heat or control the temperature of the solution or the protease 1601 in protease container portion 1655 to make the protease degradation reaction efficient or optimize it. The electric heater is described in FIG. 15, but it is not limited thereto. Another heating method than electricity may be adopted. In another embodiment, a temperature regulator may be disposed.

In the protease container portion 1655, the generated peptide fragments are conveyed to ketoamine oxidase container portion 1656 in which immobilized ketoamine oxidase 1602 and the hydrogen peroxide detector 1603 are contained.

In the ketoamine oxidase container portion 1656, the ketoamine oxidase 1602 is immobilized to base material 1614 to form enzyme layer 1611. In FIG. 15, the base material 1614 and the ketoamine oxidase 1602 are formed as an immobilization layer in the ketoamine oxidase container portion 1656. The peptide fragments conveyed into the ketoamine oxidase container portion 1656 react with the ketoamine oxidase 1602 to generate hydrogen peroxide as a result. The generated hydrogen peroxide is detected with the hydrogen peroxide detector 1603 arranged in close proximity.

Even in a configuration in which the protease and the ketoamine oxidase are arranged apart, there may be a noise cause in a substance or the like in the solution. The sensor according to the present disclosure may further include a mechanism for reducing such noise, and may be configured to be connected to the mechanism.

In some embodiments, the hydrogen peroxide detector may be covered with an ion exchange resin, and a layer or membrane of ion exchange resin may be disposed on the surface of the hydrogen peroxide detector.

A sensor according to some embodiments may be a pair or set of differential or difference sensors having a configuration in which the protease and the ketoamine oxidase are arranged apart.

In a difference sensor according to some embodiments, the hydrogen peroxide detector may be covered with an ion exchange resin, and a layer or a membrane of ion exchange resin may be disposed on the surface of the hydrogen peroxide detector.

Figure 16:
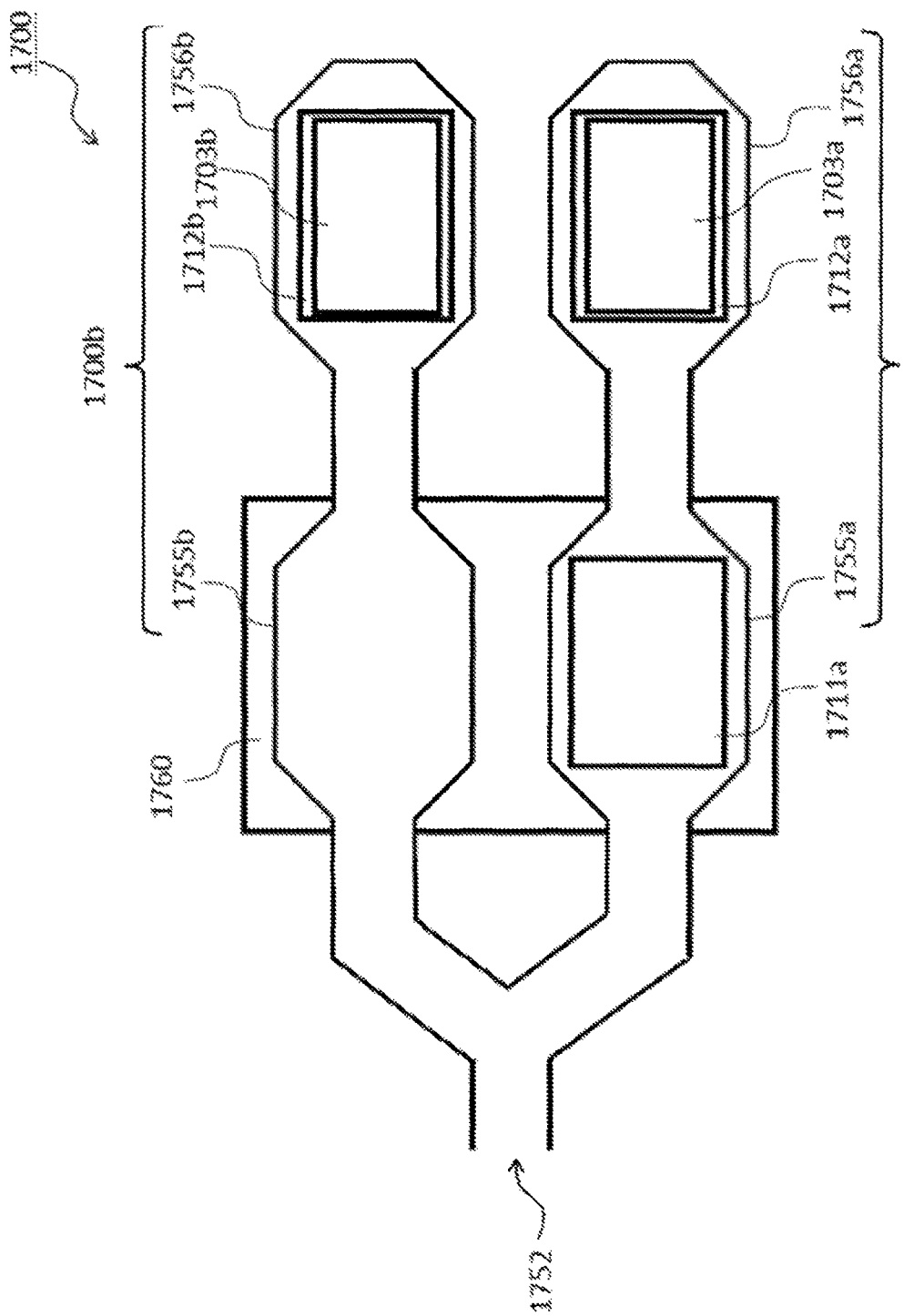
FIG. 16 illustrates a schematic plan view of a sensor according to an embodiment of the present disclosure.

In sensor 1700 shown in FIG. 16, the protease is separated from the ketoamine oxidase and disposed in a separate container portion.

The solution introduced through inlet 1752 is divided into main sensor 1700a and sub-sensor 1700b. The solution is introduced into the protease container portion 1755a in the main sensor 1700a. Enzyme layer 1711a to which protease is immobilized is disposed in the protease container portion 1755a. The peptide fragments generated in the protease container portion 1755a are conveyed through the channel to ketoamine oxidase containing container 1756a. Ketoamine oxidase layer 1712a and hydrogen peroxide detector 1703a to which ketoamine oxidase is immobilized are disposed in the ketoamine oxidase container 1756a shown in FIG. 16. By the reaction of the ketoamine oxidase container portion 1756a, the glycated peptide fragments are eventually detected as hydrogen peroxide.

On the other hand, the flow path and the container portion of the sub-sensor 1700b are configured in the same manner as the main sensor 1700a, but the protease is not disposed. In other words, the chamber 1755b into which the solution is first introduced has a structure similar to that of the protease container portion 1755a of the main sensor 1700a, but does not contain protease. As a next chamber (container portion) of the chamber 1755b without protease, ketoamine oxidase container portion 1756b is disposed. In the ketoamine oxidase container 1756b of the sub-sensor 1700b, similar to the ketoamine oxidase container 1756a of the main sensor 1700a, the ketoamine oxidase layer 1712b having ketoamine oxidase immobilized thereto and hydrogen peroxide detector 1703b are disposed.

Heater 1760 is provided in the protease container portion 1755a of the main sensor 1700a and the corresponding chamber 1755b of the sub-sensor 1700b. Thus, the rate of the degradation reaction by the protease in the protease container portion 1755a is increased, and the same reaction can be made efficiently or optimized. Furthermore, the configuration and conditions of the flow path of the sub-sensor 1700b may be as similar as those of the main sensor 1700a except for the absence of protease.

The difference signal between the output signal from the hydrogen peroxide detector 1703a of the main sensor 1700a and the output signal from the hydrogen peroxide detector 1703b of the sub-sensor 1700b can be calculated. From this difference operation, it is possible to determine the concentration of the hydrogen peroxide of interest in the hydrogen peroxide detector 1712a and the concentration of the glycated protein which is the test substance in the original solution related thereto.

In some embodiments, the protease and the ketoamine oxidase may be separately subjected to temperature control. In some embodiments, a temperature control device for each of the protease and the ketoamine oxidase may be disposed. The temperature control device may be a heating device, a cooling device, or both, or may be a temperature and cooling controllable device.

In some embodiments, the sensor may have a temperature control container portion between the protease container portion and the ketoamine oxidase container portion. In some embodiments, the container portion for temperature control may change or control the temperature of the solution delivered from the protease container portion to approach the operating temperature of the ketoamine oxidase when there is a difference in the operating temperature between the protease and ketoamine oxidase. In some embodiments, a heating device may be disposed with respect to the protease and a cooling device may be disposed to the container portion for temperature control. In some embodiments, a heating device may be disposed relative to the ketoamine oxidase.

Figure 17:
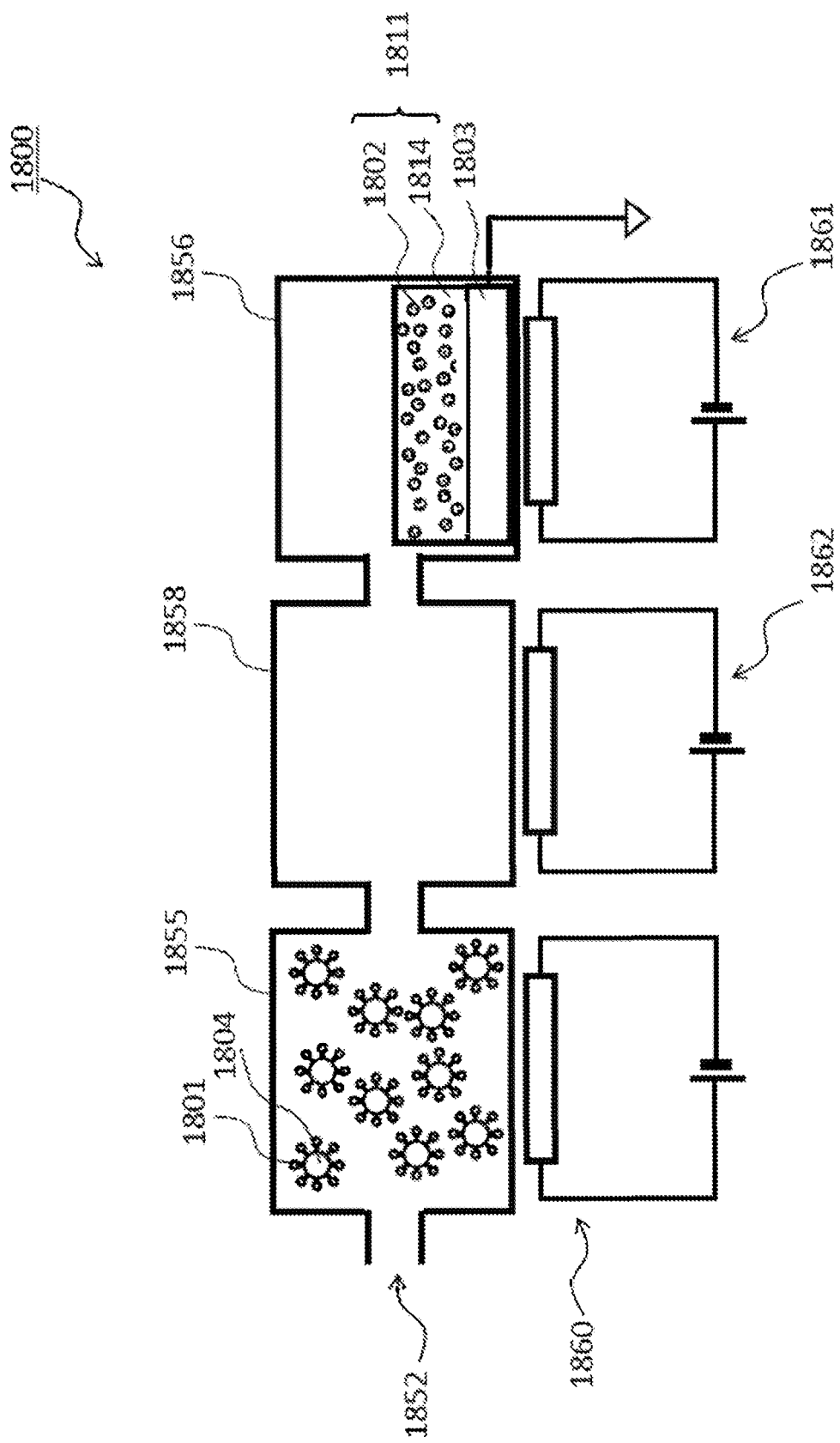
FIG. 17 illustrates a schematic configuration of a sensor according to an embodiment of the present disclosure.

Sensor 1800 shown in FIG. 17 has protease container portion 1855, cooling solution container portion (cooling portion) 1858, and ketoamine oxidase container portion 1856, which are fluidly connected in a serial manner. The protease container portion 1855 includes liquid inlet 1852, from which a solution can be introduced into the protease container portion 1855. In the protease container portion 1855, protease 1801 is contained in a state of being immobilized to beads 1804.

Heater 1860 is disposed to the protease container portion 1855 shown in FIG. 17. The heater 1860 may heat or control the temperature of the solution or the protease 1801 in the protease container portion 1855 to increase the speed of the protease reaction, and thus the reaction can be made efficient or optimized.

The peptide fragments generated in the protease container portion 1855 are conveyed to the ketoamine oxidase container portion 1856 which is fluidly connected via the cooling solution container portion 1858. Immobilized ketoamine oxidase 1802 and hydrogen peroxide detector 1803 are contained in the ketoamine oxidase container portion 1856. The hydrogen peroxide detector 1803 is connected to a measuring device (not shown) and can transmit an electric signal to the measuring device (not shown).

In the ketoamine oxidase container portion 1856, the ketoamine oxidase 1802 is immobilized to base material 1814 to form enzyme layer 1811. In FIG. 17, the base material 1814 and the ketoamine oxidase 1802 are formed as an immobilization layer in the ketoamine oxidase container portion 1856. The peptide fragments conveyed into the ketoamine oxidase container portion 1856 react with the ketoamine oxidase 1802 to generate hydrogen peroxide as a result. The generated hydrogen peroxide is detected with the hydrogen peroxide detector 1803 arranged in close proximity.

Heater 1861 is disposed in the ketoamine oxidase container portion 1856. The heater 1861 may heat or control the temperature of the solution or the ketoamine oxidase 1802 in the ketoamine oxidase container portion 1856 to increase the speed of the enzymatic reaction, and thus the reaction can be made efficient or optimized.

In FIG. 17, individual heaters 1860, 1861 are arranged in the protease container portion 1855 and the ketoamine oxidase container portion 1856, respectively. Thereby, temperature control or heating can be individually performed with respect to the protease 1801 and the ketoamine oxidase 1802. This allows independent temperature control, e.g., in time or temperature, or both. In some embodiments, the temperature of the protease container portion 1855 or the protease 1801 can be controlled higher than the temperature of ketoamine oxidase container portion 1856 or the ketoamine oxidase 1802. In some embodiments, the temperature of the protease container portion 1855 or the protease 1801 can be controlled below the temperature of ketoamine oxidase container portion 1856 or the ketoamine oxidase 1802.

If the solution heated in the protease container portion 1855 is sent to the ketoamine oxidase container portion 1856, it may be time consuming and inefficient for the solution to reach an appropriate temperature for the ketoamine oxidase 1802, or accurate measurement may not be possible. Therefore, the solution may be once cooled before being introduced into the ketoamine oxidase container portion 1856. The sensor 1800 as shown in FIG. 17 allows the heated protease container portion 1855 to maintain the heated solution in the cooling solution container portion 1858. The solution is cooled using a cooling device (circuit/element) 1862 (e.g., a Peltier element) to approach the optimal temperature or operating temperature of the ketoamine oxidase 1802. Thereafter, the solution may be sent to the ketoamine oxidase container portion 1856. This makes it possible, for example, to perform the measurement efficiently or accurately.

The sensor 1800 shown in FIG. 17 may be used as follows as an example. First, a solution containing a substance to be measured is introduced into the protease container portion 1855. The protease container portion 1855 may start heating before introducing the solution, or may start heating after introducing the solution. After performing peptide fragmentation in the protease container portion 1855, the solution is sent to the cooling solution container portion 1858. The cooling solution container portion 1858 may start cooling before introducing the solution, or may start cooling after introducing the solution. After cooling to a sufficient or appropriate temperature in the cooling solution container portion 1858, the solution may be sent to the ketoamine oxidase container portion 1856. The ketoamine oxidase container portion 1856 may start heating after the solution is introduced.

In some embodiments, liquid feeding may be performed by applying pressure from the solution inlet 1852. In some embodiments, liquid delivery may be performed by varying the volume of each container portion 1855, 1856, 1858 or by applying pressure to each container portion. The protease container portion 1855 may have an air hole (not shown). In some embodiments, the pressure during liquid delivery may be a positive pressure. In some embodiments, the pressure during liquid delivery may be a negative pressure. In some embodiments, a valve may be disposed near each or both of the inlet and the outlet of each container portion. The valve may function to remove bubbles from the flow path that may be generated, such as due to differences in the temperature of each receptacle.

In some embodiments, when the solution exits from the protease container portion, the protease and the beads may exit the protease container portion. For example, the protease and the beads may enter the cooling container portion and may enter the ketoamine oxidase container portion. In some embodiments, the sensor may be configured such that the protease and the beads remain substantially in the protease container portion upon delivery of solution.

In FIG. 17, electric heaters 1860, 1861 and cooling device 1862 are described, but not limited thereto. The heaters 1860, 1861 may employ heating schemes other than electricity. The cooling device 1862 may employ a cooling scheme other than the Peltier element. In other embodiments, other temperature regulators may be arranged.

In some embodiments, the solution inlet 1852, the protease container portion 1855, the cooling solution container portion 1858, and the ketoamine oxidase container portion 1856 may be a single component, e.g., a cassette or a disposable fluid device. In some embodiments, the heaters 1860, 1861 and the cooling device 1862 may be fixed to the main body. The sensor 1800 may be configured such that the fluidic device is inserted into or fixed to the main body. Insulation may be disposed between the heaters 1860, 1861 and the cooling device 1862. Thus, for example, the efficiency of the temperature control can be increased.

3. Arrangement of Hydrogen Peroxide Electrodes

Various configurations are possible for the layout or arrangement of the hydrogen peroxide electrodes. Hereinafter, configurations of hydrogen peroxide electrode will be exemplarily described.

<Electrode Arrangement Example 1>

The hydrogen peroxide electrode shown in the present disclosure is not limited to applications of measuring glycated proteins or fructosamine, and may also be used in other applications including electrochemical measurements of solutions. That is, a sensor or a sensor chip according to an embodiment of the present disclosure includes a hydrogen peroxide electrode. The reference electrode of the hydrogen peroxide electrode may be sandwiched between the counter electrode and the working electrode. The sensor chip may have a liquid container portion. The liquid container portion may extend in the longitudinal direction. The volume of the liquid container portion may be smaller than or equal to 10 µL, 5 µL, 4 µL, 3 µL, 2 µL, 1 µL, 0.9 µL, 0.8 µL, 0.7 µL, 0.6 µL, 0.5 µL, 0.4 µL, 0.3 µL, 0.2 µL, or 0.1 µL. The liquid container portion may have a liquid inlet. The liquid container portion may have a liquid outlet. The liquid container portion may have an air hole. The air hole may have a function of discharging the gas present in the liquid container portion to the outside of the sensor chip when the liquid is introduced into the liquid container portion. The sensor chip may have an electrical circuit and may be configured to be connected to an electrical circuit. The sensor chip may have an output terminal for connection with an electrical circuit.

Figure 18:
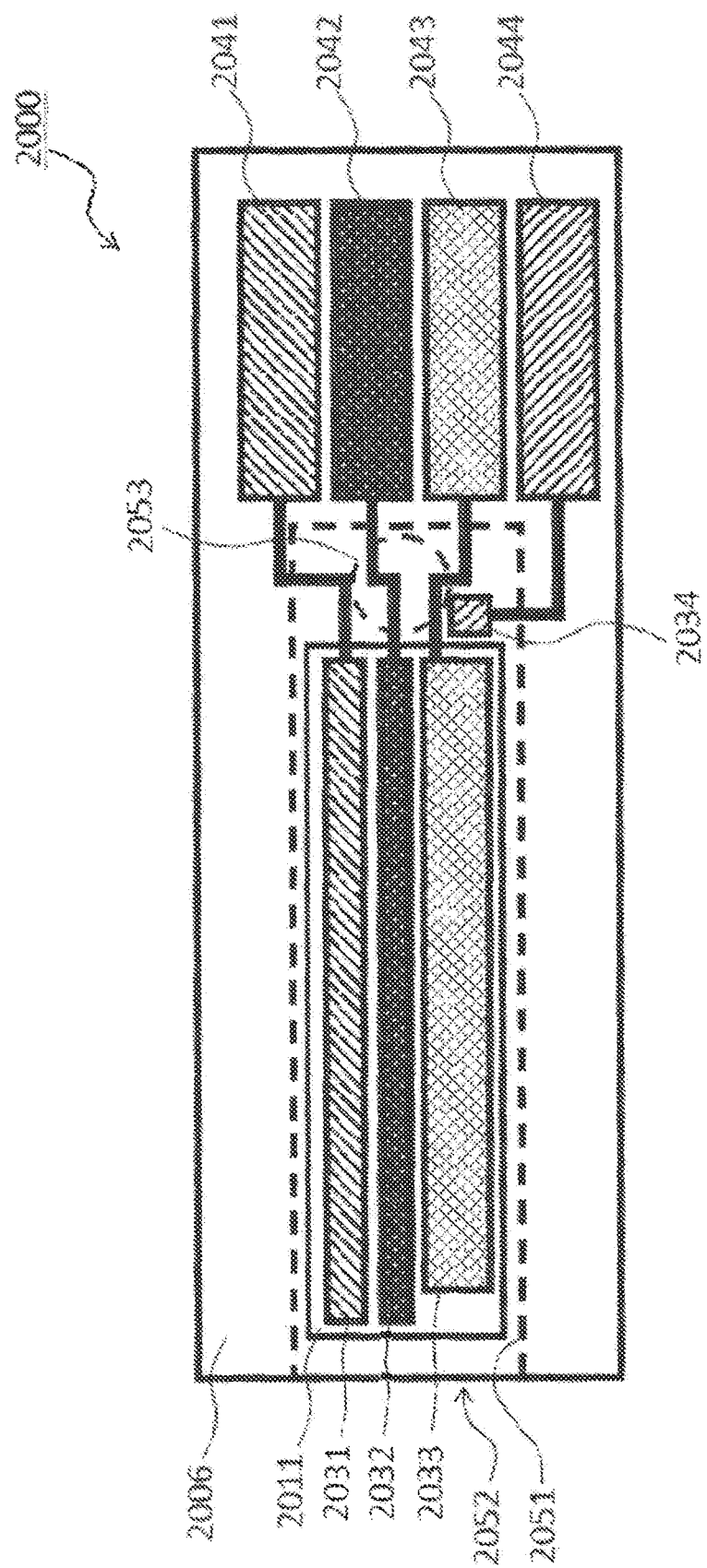
FIG. 18 illustrates a schematic plan view of a sensor chip according to an embodiment of the present disclosure.

FIG. 18 is a top view schematically showing the electrode configuration of a sensor chip as one embodiment. In sensor chip 2000 of FIG. 18, counter electrode 2031, reference electrode 2032, and working electrode 2033 are disposed on substrate 2006 so as to contact the introduced solution, and enzyme layer 2011 is disposed so as to cover these electrodes.

The sensor chip 2000 may further include a member defining a flow path or a liquid container portion, for example, a chip cover, and may be formed as a sensor chip without such a chip cover. In FIG. 18, a sensor chip cover (not shown) defining the flow path and the liquid container portion is covered on the upper surface of the sensor chip. Portion 2051 on the sensor chip corresponding to the liquid container portion is defined, and the liquid is introduced into the liquid container portion 2051 through inlet 2052. The chip cover has air hole 2053 on a side opposite to the liquid inlet 2052 with respect to the liquid container portion 2051.

Hydrogen peroxide electrodes 2031,2032,2033 are arranged so as to extend longitudinally along the liquid container portion 2051 in parallel with each other. The liquid comes to the side of the inlet 2052, and the end of the working electrode 2033 is formed to be shorter than the end of the other electrodes, that is, the counter electrode 2031 and the end of the reference electrode 2032. The liquid introduced from the inlet 2052 extends in the longitudinal direction in the liquid container portion 2051. If the liquid contacts the working electrode 2033 initially or simultaneously with another electrode, large current flows and the electrode may be damaged. With such a configuration, damage to the electrode can be avoided.

The sensor chip 2000 shown in FIG. 18 further includes liquid detection electrode 2034 in the liquid container portion. In FIG. 18, the electrode 2034 is disposed at a position where the liquid comes into contact last when the liquid enters the liquid container portion 2051. By detecting the presence or absence of liquid at the liquid detection electrode 2034, it is possible to confirm that the liquid container portion 2051 or the hydrogen peroxide electrodes 2031, 2032,2033 are sufficiently filled with liquid. When the liquid is detected by the liquid detection electrode 2034, it may be notified to the user that the collection of the liquid has been terminated. Alternatively, if the liquid is not detected by the liquid detection electrode 2034 even after waiting for a predetermined time or more, a notification may be made to the user such that the measurement is not started because the liquid cannot be sufficiently collected, or the collection of the liquid is to be redone, or the use of another chip is recommended.

The sensor chip 2000 shown in FIG. 18 has output terminals 2041, 2042, 2043, 2044 electrically connected to the counter electrode 2031, the reference electrode 2032, the working electrode 2033, and the liquid detection electrode 2034. The sensor chip may be configured to be connected in a pluggable or detachable manner to an electrical circuit or another device having an electrical circuit, neither of which is shown. In the sensor chip 2000 shown in FIG. 18, the output terminal is disposed in the detachable portion.

Only one detection electrode is shown in FIG. 18. However, in some embodiments, a disposed of detection electrodes may be disposed. A plurality of electrodes may be placed in the flow path in the direction of travel of the liquid. For example, the detection electrode may be disposed at a location where the detection portion first touches the liquid, at a location where the detection portion is completely in contact with the liquid, or intermediate therebetween. For example, the first sensing electrode may sense that liquid has begun to enter the detection portion, the flow path, or the liquid container portion. The middle electrode can detect whether or not the liquid is entering. If the liquid does not enter the middle electrode, only a part of the detection portion is used, and therefore, it may be used to notify that measurement is impossible or to notify that measurement can be performed with a large error.

Other arrangements and variations will be exemplarily described below. The arrangements and descriptions may be partially omitted. Other configurations may be applied to the embodiments and examples.

<Multiple Electrode Arrangements>

A plurality of or a plurality of types of sensors or hydrogen peroxide electrodes may be disposed in the liquid container portion of the sensor chip. The plurality of sensors may be of the same type of sensors, or may be a combination of a main sensor and a sub-sensor for difference measurement as described above.

<Electrode Arrangement Example 2>

Figure 19:
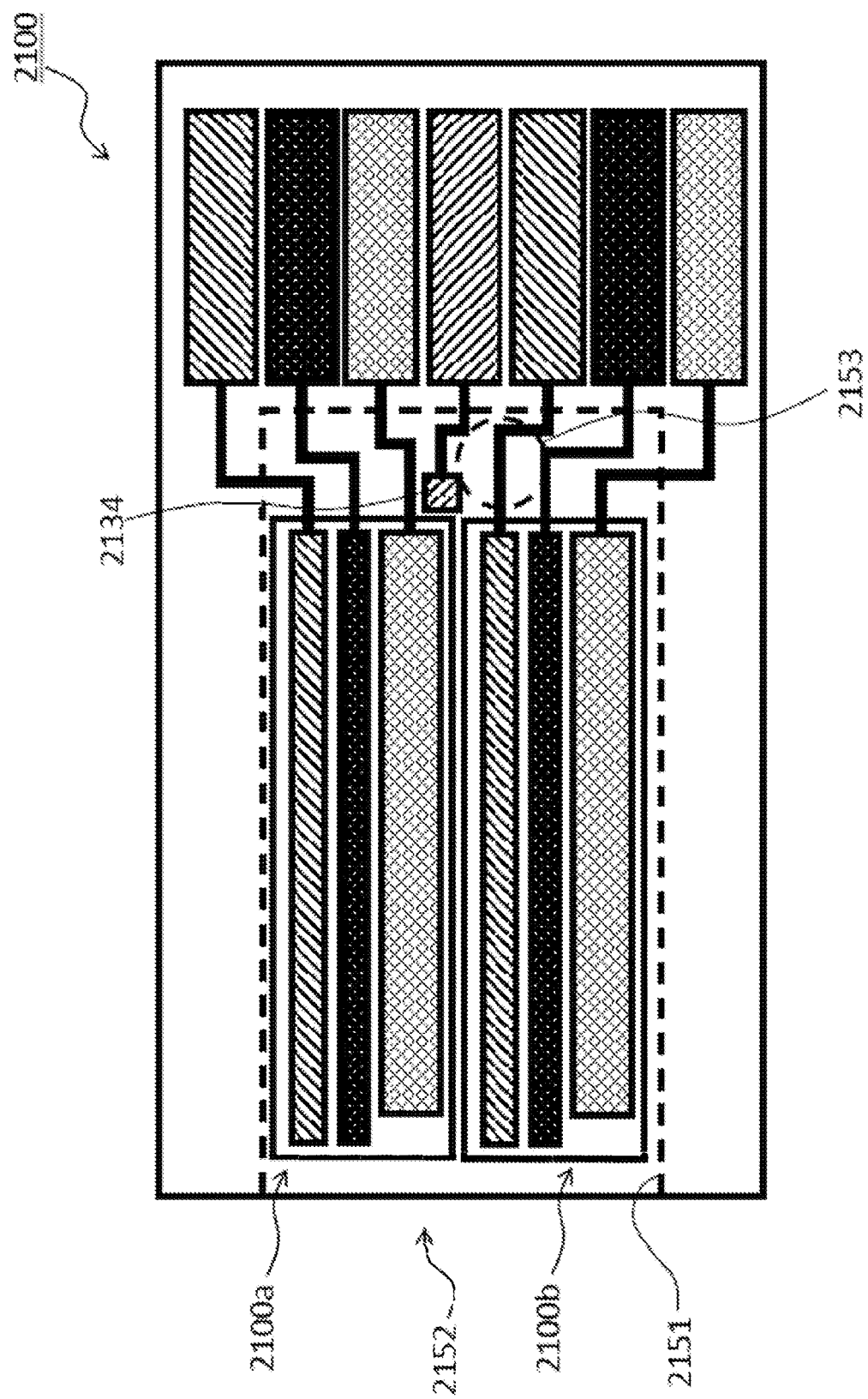
FIG. 19 illustrates a schematic plan view of a sensor chip according to an embodiment of the present disclosure.

In sensor chip 2100 shown in FIG. 19, a plurality of sensors 2100*a*, 2100*b* are arranged in parallel with each other in the longitudinal direction in liquid container portion 2151. The reference electrodes and the counter electrodes of the plurality of sensors 2100*a*, 2100*b* are connected to each other and the working electrodes in a common manner in the circuit. The liquid is introduced from fluid inlet 2152, and by the capillary phenomenon and the action of an immobilization film which also functions as a hydrophilic water-containing polymer, or the like, flows in the liquid container portion 2151, and while the air inside is extruded from air hole 2153, it fills the liquid container portion 2151 and finally reaches detection electrode 2134.

<Electrode Arrangement Example 3>

Figure 20:
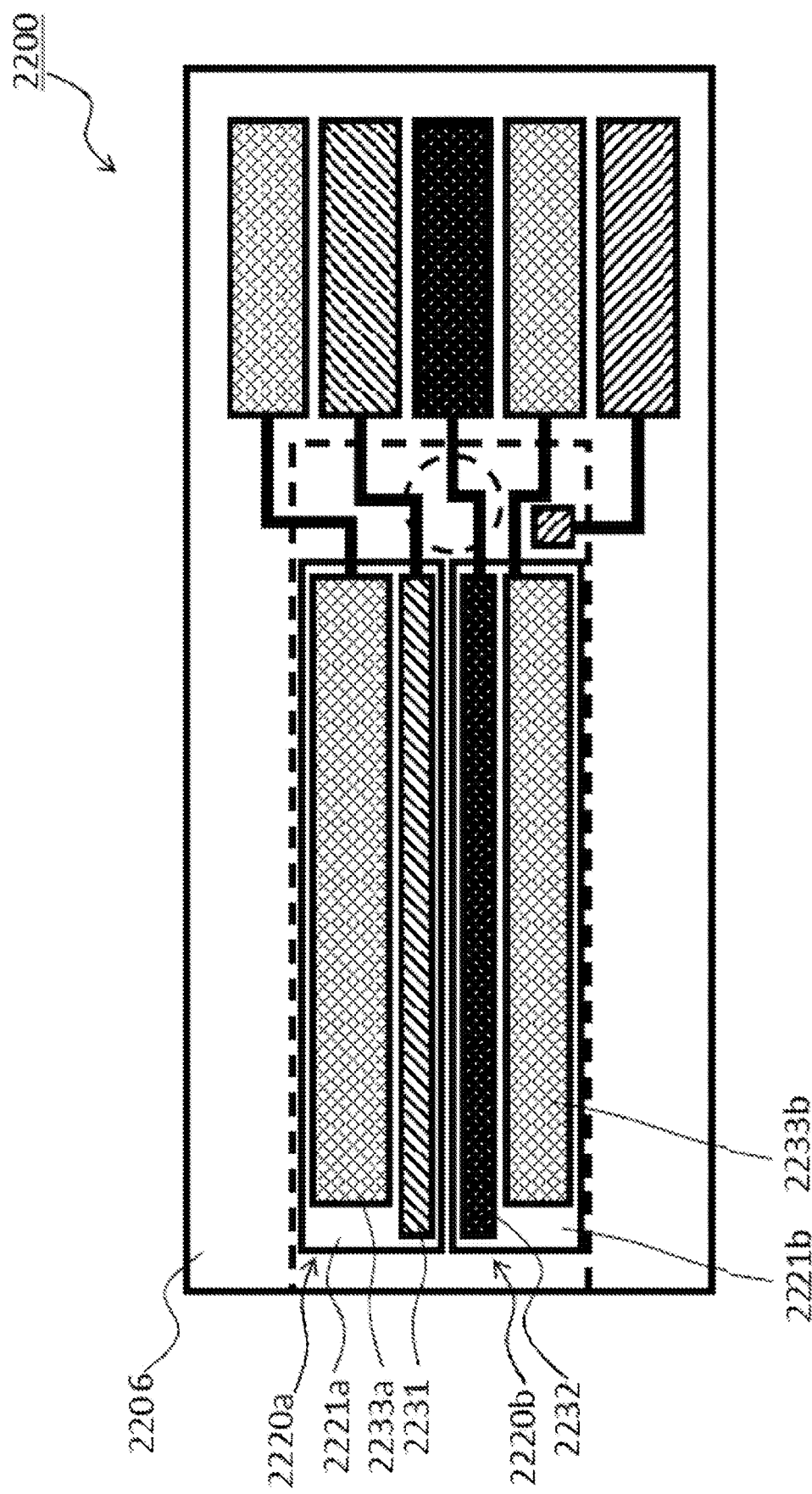
FIG. 20 illustrates a schematic plan view of a sensor chip according to an embodiment of the present disclosure.

In sensor chip 2200 shown in FIG. 20, a part of the hydrogen peroxide electrode as shown in FIG. 12 is shared by a plurality of sensors. That is, the sensor chip 2200 shown in FIG. 20 includes main sensor 2220*a* and sub-sensor 2220*b*. In the main sensor 2220*a*, working electrode 2233*a* and counter electrode 2131 are disposed on substrate 2206, and enzyme layer 2221*a* for the main sensor is disposed on these electrodes. In the sub-sensor 2220*b*, working electrode 2233*b* and reference electrode 2232 are disposed on the substrate 2206, and enzyme layer 2221*b* for the sub-sensor is disposed on these electrodes. Reference electrode 2232 is disposed or sandwiched between the counter electrode 2231 and the working electrode 2233*b* on the substrate 2206.

<Multi-Sensor Assembly Type>

When disposing multiple sensors on the same sensor chip, it is not necessary to directly form all the sensors on the main body substrate of the sensor chip. For example, each manufactured sensor may be bonded onto the main body substrate.

Figure 21:
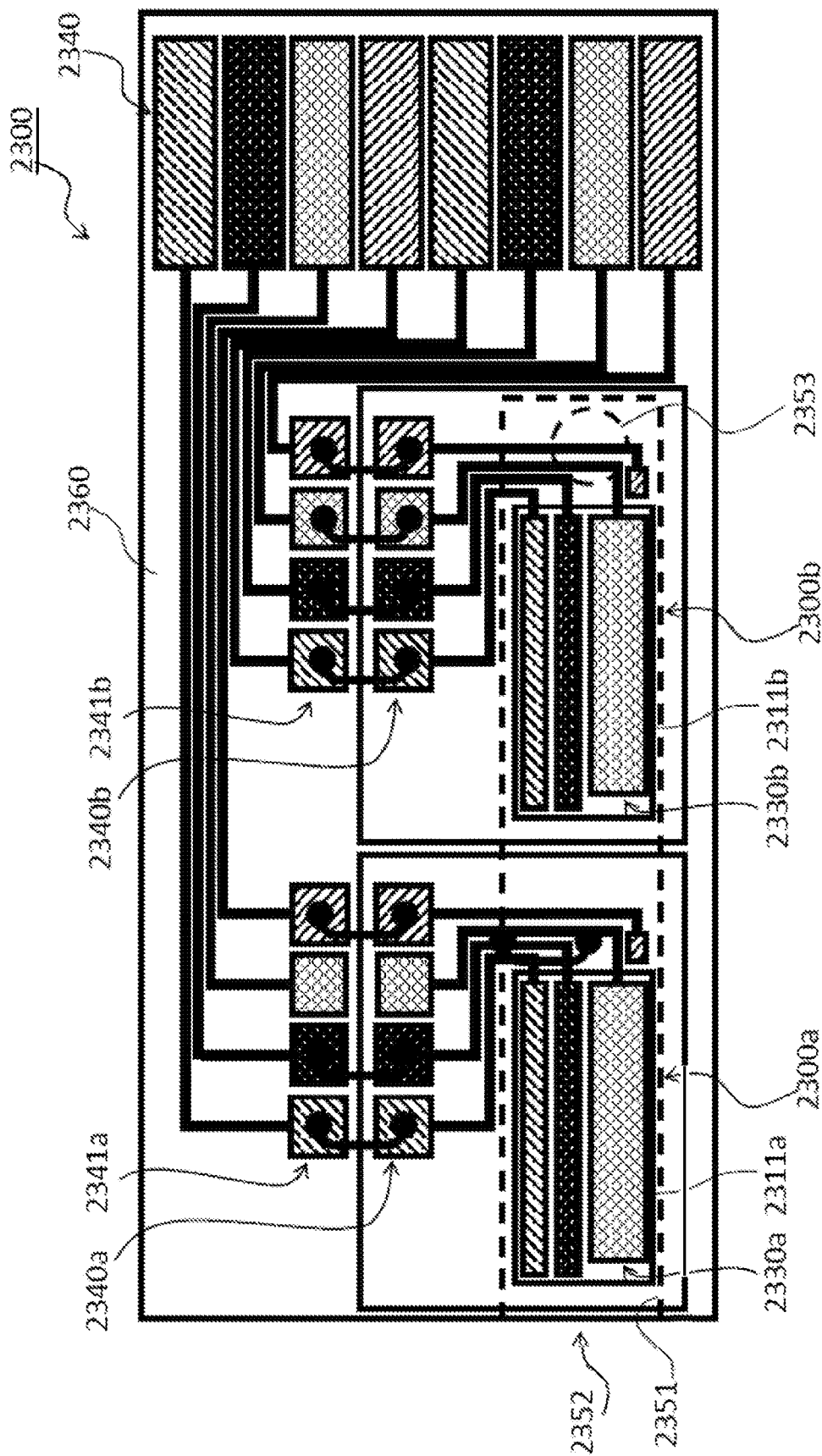
FIG. 21 illustrates a schematic plan view of a sensor chip according to an embodiment of the present disclosure.

In sensor chip 2300 shown in FIG. 21, two already manufactured sensors 2300*a*, 2300*b* are bonded onto main body substrate 2360.

Enzyme layers 2311*a*, 2311*b* or hydrogen peroxide electrodes 2330*a*, 2330*b* of the sensors 2300*a*, 2300*b* are formed so as to extend in the longitudinal direction of liquid container portion 2351 extending from liquid inlet 2352 toward air hole 2353.

In the sensor chip 2300 of FIG. 21, on the main body substrate 2360 and on each sensor, corresponding bonding pads 2340*a*, 2340*b*, 2341*a*, 2341*b* are formed, respectively. These bonding pads are electrically bonded after or during bonding of the sensors 2300*a*, 2300*b* onto the main body substrate 2360. For example, the bonding pads may be connected to each other by wire bonding.

In the sensor chip 2300 of FIG. 21, output terminal 2340 which can be connected to an electric circuit (not shown) or the like is disposed on the main body substrate 2360. These output terminals 2340 are connected to the corresponding bonding pads 2341*a*, 2341*b* by wiring. The counter electrode and the reference electrode may be short-circuited via the sensor chip 2300 or an electrical circuit. With such a configuration, for example, depending on the durability of the enzyme layer or the configuration of the other layer, when it is difficult to simultaneously manufacture two sensors in one chip or when the yield of the two sensors is remarkably different, it is possible to separately manufacture the two sensors and to combine the non-defective products thus the total manufacturing costs can be suppressed.

<Other Electrode Directions>

The hydrogen peroxide electrode may be formed along a direction other than the longitudinal direction of the elongated liquid container portion.

Figure 22:
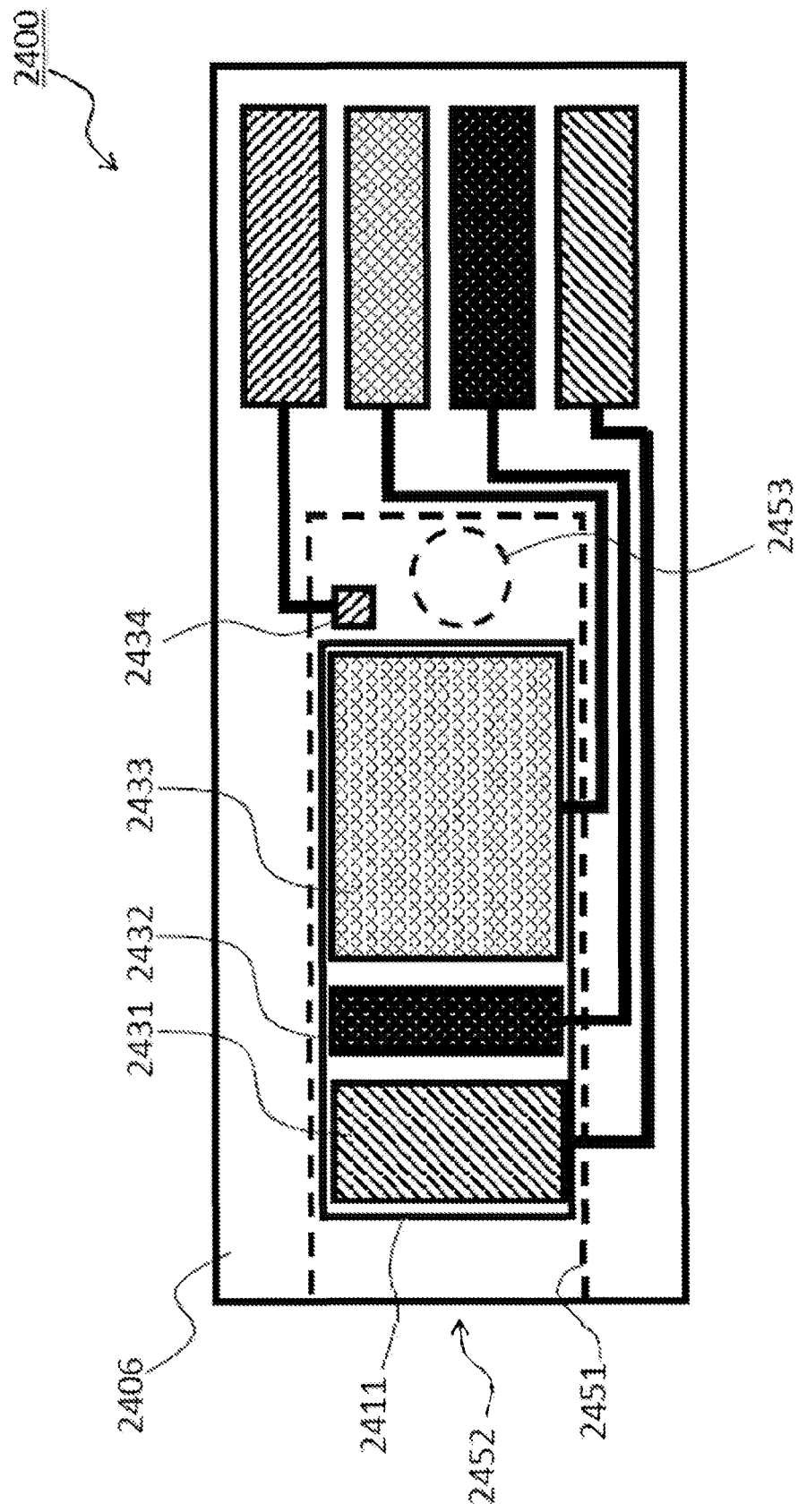
FIG. 22 illustrates a schematic plan view of a sensor chip according to an embodiment of the present disclosure.

For example, like sensor chip 2400 shown in FIG. 22, each electrode extending perpendicularly to the longitudinal direction of the liquid container portion 2451 may be disposed on substrate 2406. More specifically, in the hydrogen peroxide electrode of FIG. 22, counter electrode 2431, reference electrode 2432, and working electrode 2433 are arranged in a direction perpendicular to the longitudinal direction from liquid inlet 2452 to air hole 2453 in liquid container portion 2451. The reference electrode 2432 is sandwiched between the counter electrode 2431 and the working electrode 2433. The working electrode 2433 is disposed at the last position within the three electrodes of the hydrogen peroxide electrode in the liquid flow direction during liquid introduction. Liquid detection electrode 2434 is disposed after these hydrogen peroxide electrodes. On top of the hydrogen peroxide electrode, enzyme layer 2411 is formed. Since the reference electrode 2432 is sandwiched between the counter electrode 2431 and the working electrode 2433 as in this electrode configuration, for example, external noise is reduced, and the liquid finally comes into contact with the work electrode 2433 when entering the liquid container portion 2451, thereby enabling safe measurement while avoiding an excessive current from flowing.

4. Method of Manufacturing Sensor

Hereinafter, a method of manufacturing a dual glycated protein sensor according to an embodiment of the present disclosure will be described with reference to cross-sectional schematics of FIGS. 23A to 23I.

<Formation of Hydrogen Peroxide Electrode>

Figure 23A:
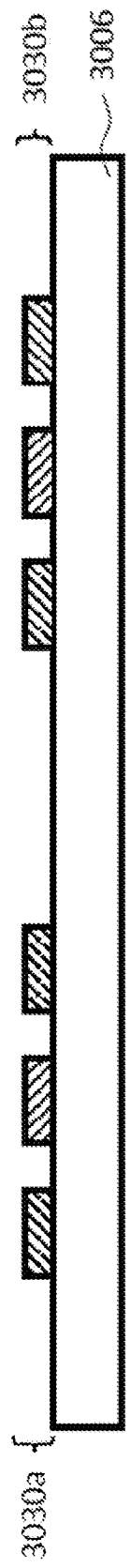
FIG. 23A illustrates a cross sectional view showing a manufacturing process of a sensor according to the present disclosure.

As shown in FIG. 23A, two sets of electrodes, i.e., first hydrogen peroxide electrode 3030*a* and second hydrogen peroxide electrode 3030*b* are formed on insulating substrate 3006. The insulating substrate 3006 may be a substrate mainly composed of glass, quartz, or ceramics. The insulating substrate 3006 may be polyethylene terephthalate (PET), polyethylene naphthalate (PEN), cycloolefin polymer (COP) resin, or the like. These are known as materials excellent in water resistance, heat resistance, chemical resistance and adhesion to the above electrode.

In each of the sets of hydrogen peroxide electrodes 3030*a*, 3030*b*, a working electrode by laminating Ti/Pt, a reference electrode by laminating Ti/Pt/Ag/AgCl, and a counter electrode by laminating Ti/Pt are formed. These laminated structures are not shown in the figure. These electrodes can be formed by, for example, sputtering, ion plating, vacuum deposition, chemical vapor deposition, electrolysis, screen printing, or the like. The sputtering method can form platinum film of thin film with high accuracy in a comparatively short time. For example, first, a film of titanium (Ti) and platinum (Pt) are formed in this order and patterned. Next, the working electrode and the counter electrode are covered, and silver (Ag) is formed on the reference electrode. Finally, a chlorination treatment is performed on the surface of the silver. As a result, the laminated electrode structure as described above can be formed. Ti is often formed for the purpose of increasing the adhesion between the substrate and Pt. Thus, the Ti layer of the hydrogen peroxide electrode may be omitted depending on the substrate and the film forming conditions. For example, when an insulating substrate made of a flexible sheet such as PET resin or COP resin is used, the Ti layer of the hydrogen peroxide electrode may be omitted.

<Formation of Enzyme Layer for Sub-Sensor>

Figure 23B:
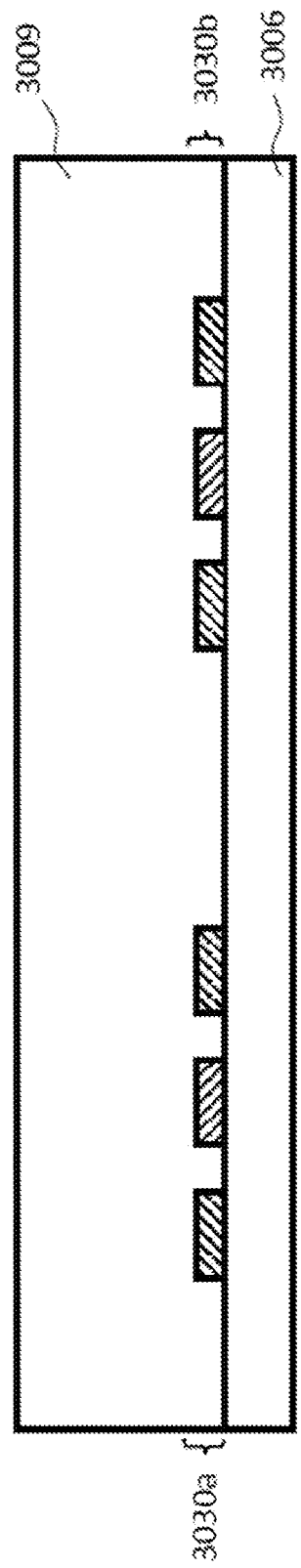
FIG. 23B illustrates a cross sectional view showing a manufacturing process of a sensor according to the present disclosure.

First, as shown in FIG. 23B, positive photoresist 3009 used in a photolithography process such as semiconductor manufacturing is spin-coated on the insulating substrate 3006 to cover two sets of the hydrogen peroxide electrodes 3030*a*, 3030*b*.

Figure 23C:
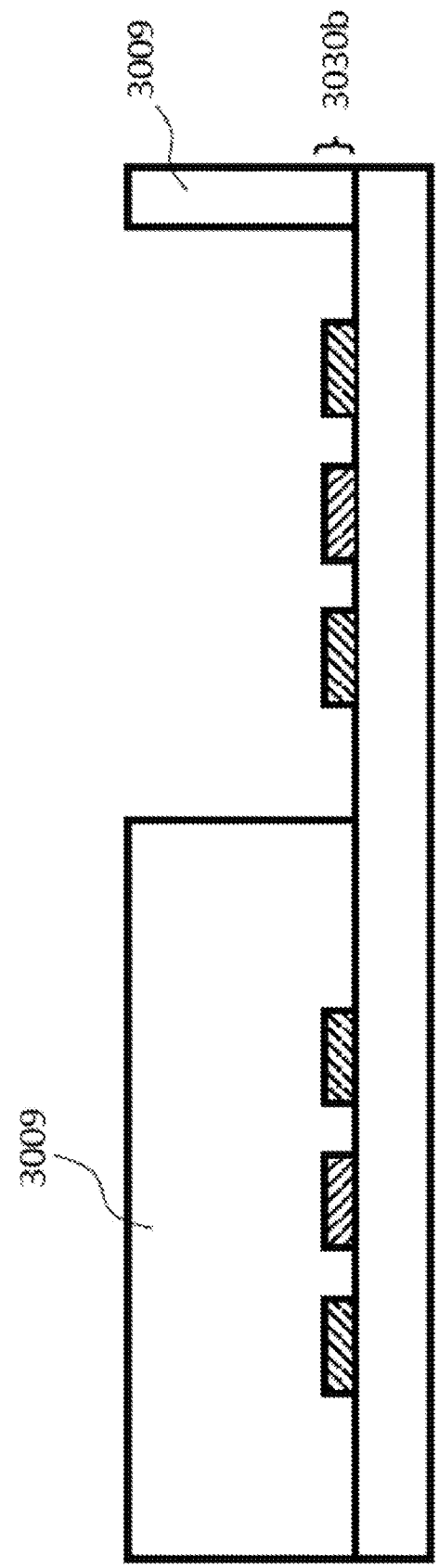
FIG. 23C illustrates a cross sectional view showing a manufacturing process of a sensor according to the present disclosure.

Subsequently, as shown in FIG. 23C, the resist 3009 is patterned by exposure, development, and etching to open the second hydrogen peroxide electrode 3030*b*.

Figure 23D:
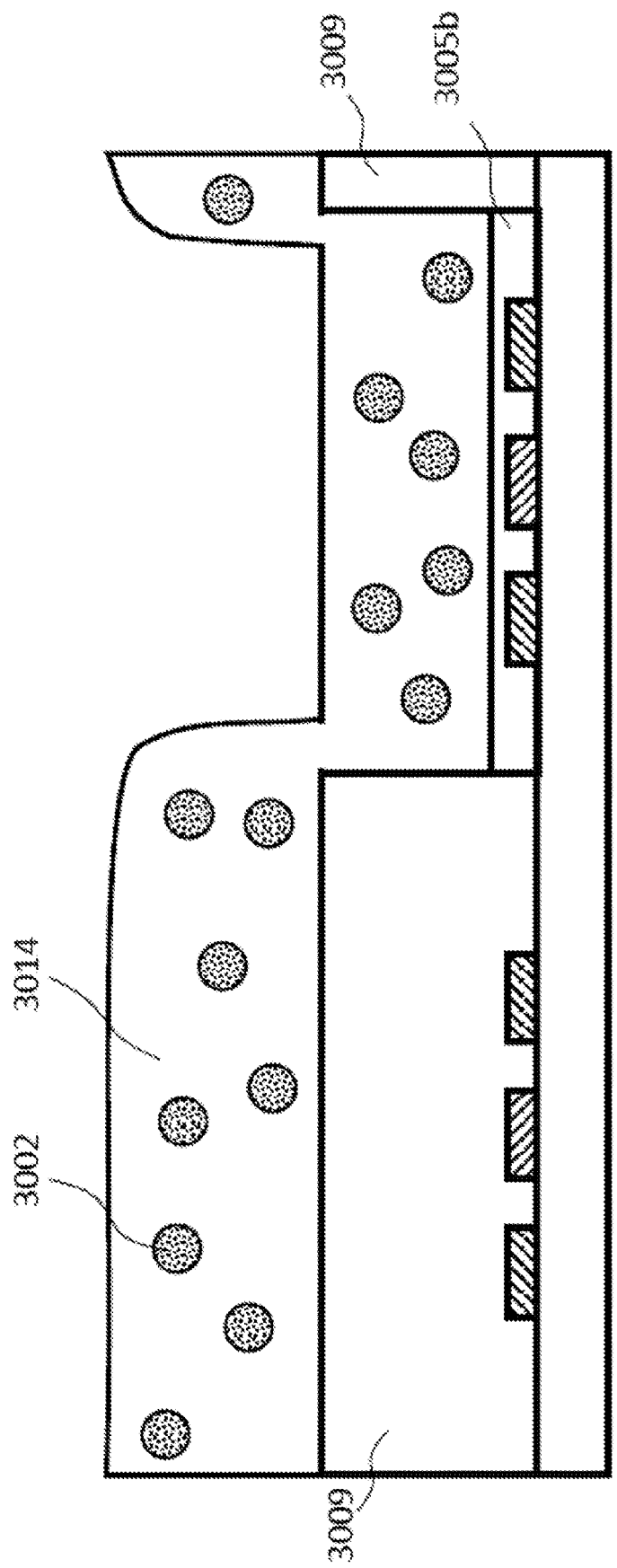
FIG. 23D illustrates a cross sectional view showing a manufacturing process of a sensor according to the present disclosure.

As shown in FIG. 23D, 3-aminopropyltriethoxysilane (APTES) solution, which is a silane coupling agent 3005*b*, is spin-applied at a rotational speed of 3000 rpm for 30 seconds and dried. Thereafter, a solution containing BSA and ketoamine oxidase 3002 serving as base material 3014 is mixed with glutaraldehyde. Then, the mixed solution is spin-coated on the substrate. The ketoamine oxidase 3002 is cured by the cross-linking reaction of glutaraldehyde.

Figure 23E:
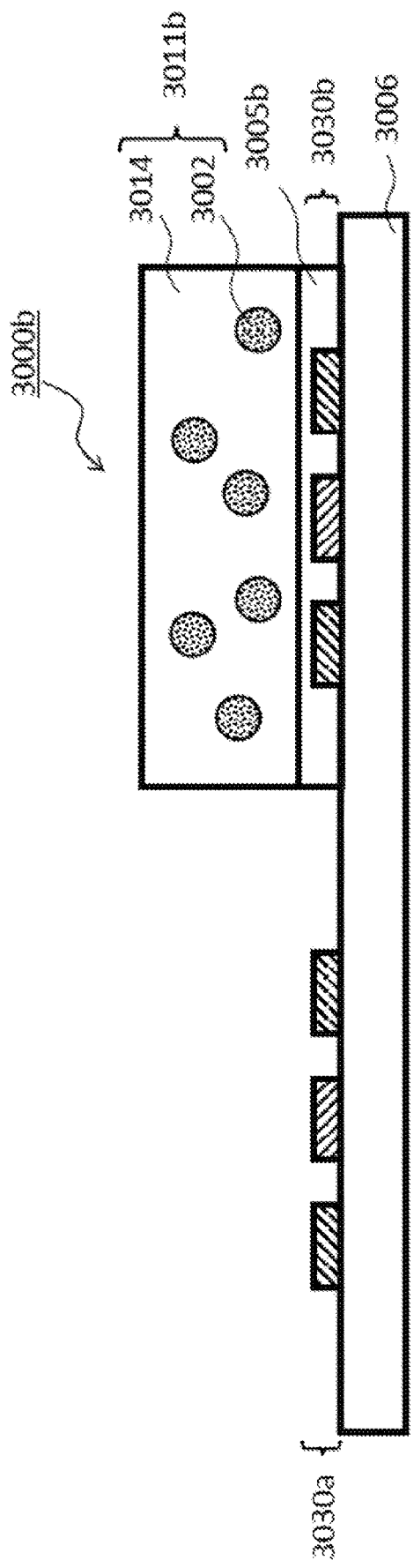
FIG. 23E illustrates a cross sectional view showing a manufacturing process of a sensor according to the present disclosure.

The resist 3009 is sonicated in acetone to lift off. Only on the second hydrogen peroxide electrode 3030*b*, enzyme membrane 3011*b* containing BSA serving as the base material 3014 and the ketoamine oxidase 3002 remains via the silane coupling agent 3005*b*. As a result, the sub-sensor 3000*b* is formed on the insulating substrate 3006, and the first hydrogen peroxide electrode 3030*a* for the main sensor is exposed. (FIG. 23E)

Figure 23F:
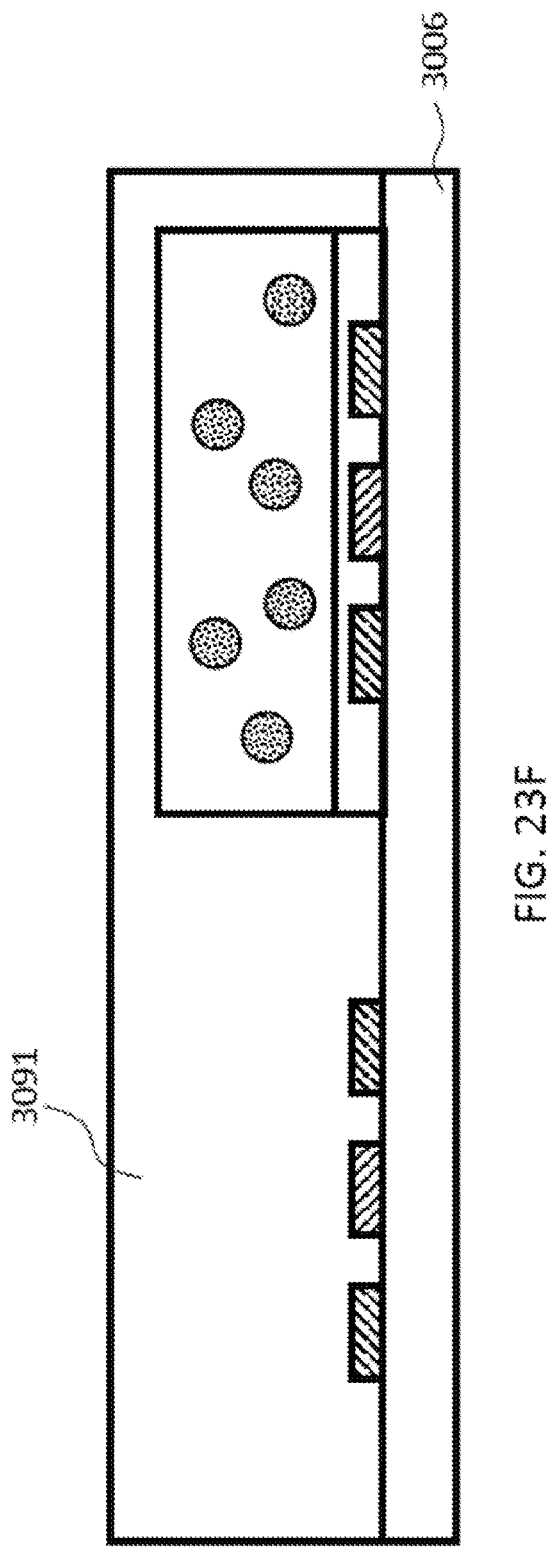
FIG. 23F illustrates a cross sectional view showing a manufacturing process of a sensor according to the present disclosure.

Similar to the process described in FIG. 23B, again the resist 3091 is spin-coated on the entire insulating substrate 3006. After application, the resist 3091 is cured so that the enzyme does not deactivate (FIG. 23F).

<Formation of Enzyme Layer for Main Sensor>

Figure 23G:
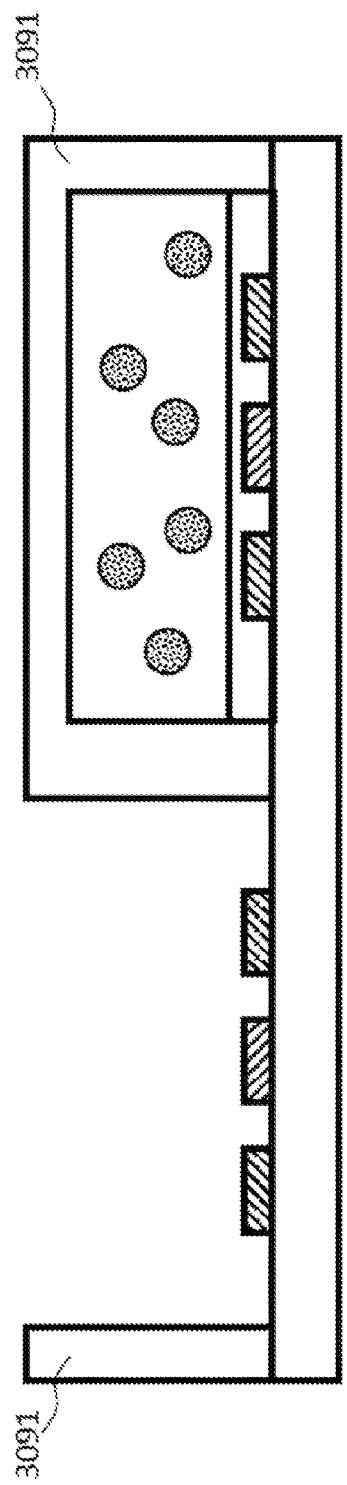
FIG. 23G illustrates a cross sectional view showing a manufacturing process of a sensor according to the present disclosure.

First, patterning is performed on the resist 3091 by exposure, development, and etching to open the first hydrogen peroxide electrode (FIG. 23G).

Figure 23H:
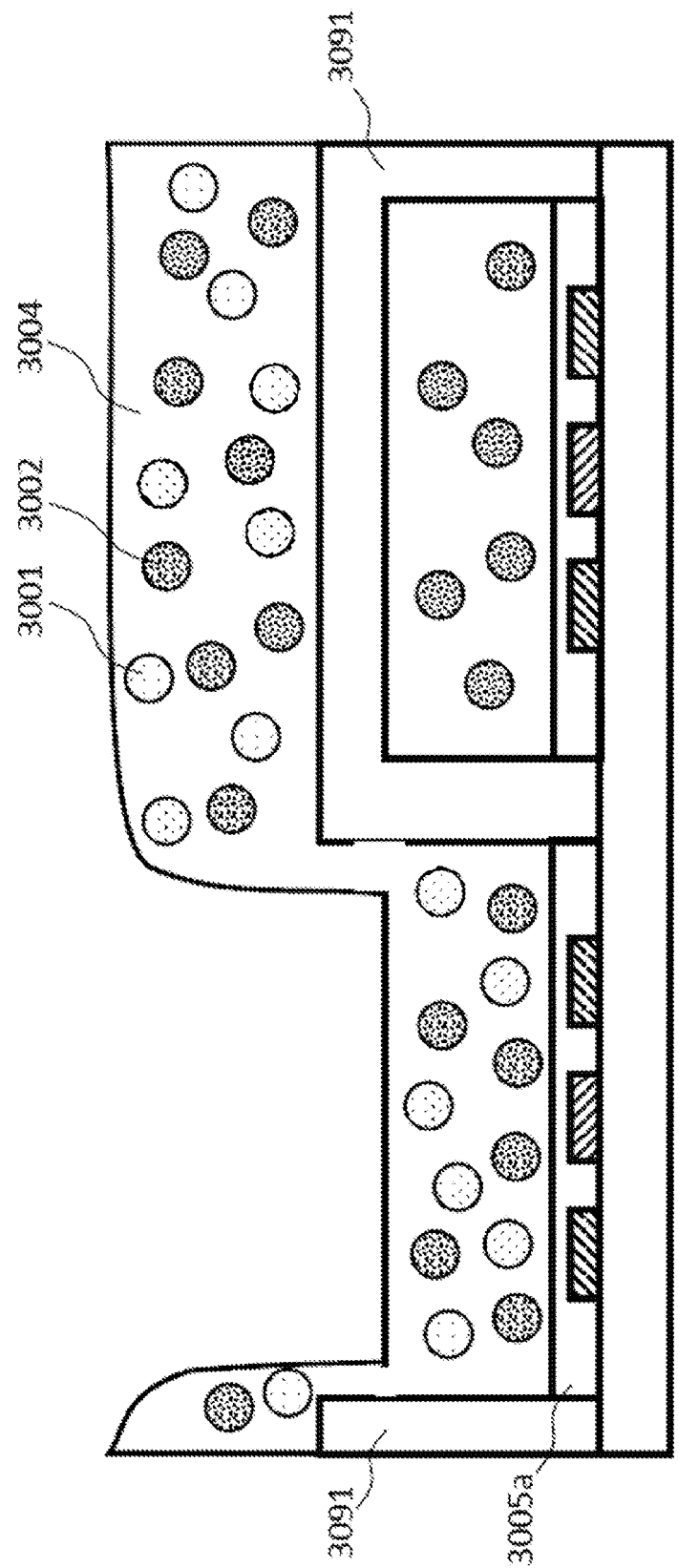
FIG. 23H illustrates a cross sectional view showing a manufacturing process of a sensor according to the present disclosure.

With an opening on the first hydrogen peroxide electrode 3030*a*, 3-aminopropyltriethoxysilane (APTES) solution, which is a silane coupling agent 3005*a*, is spin-coated at a rotational speed of 3,000 rpm for 30 seconds and dried in the same manner as in FIG. 23D. Thereafter, solution containing BSA serving as the base material 3004, ketoamine oxidase 3002 and protease 3001 is mixed with glutaraldehyde. Then, the mixed solution is spin-coated on the substrate. The ketoamine oxidase 3002 and the protease 3001 are cured by the cross-linking reaction of glutaraldehyde (FIG. 23H).

Figure 23I:
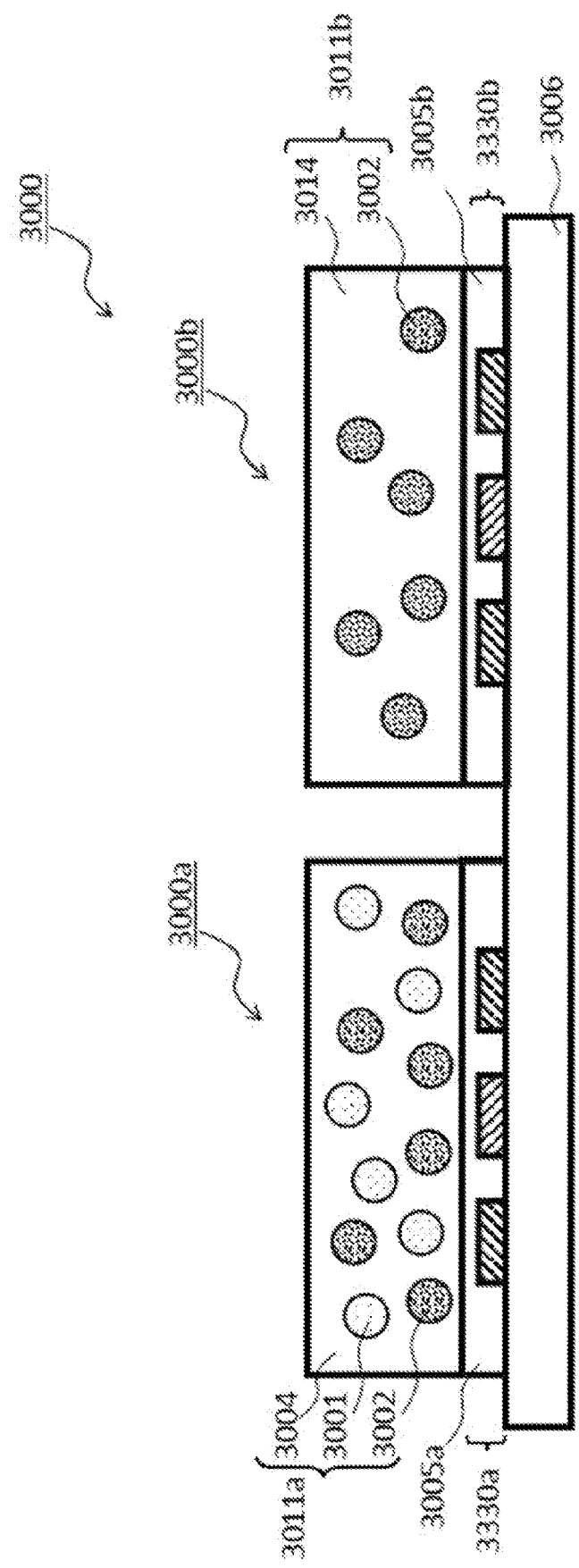
FIG. 23I illustrates a cross sectional view showing a manufacturing process of a sensor according to the present disclosure.

The resist 3091 is sonicated in acetone to lift off. In this manner, a sensor was produced in which, on the first and second hydrogen peroxide electrodes 3330*a*, 3330*b* on the insulating substrate 3006, the enzyme layer 3011*a* containing the protease 3001 and the ketoamine oxidase 3002 immobilized to the BSA 3004 serving as a base material, respectively, via silane coupling agents 3005*a*, 3005*b*, and the enzyme layer 3011*b* including only the ketoamine oxidase 3002 serving as an enzyme and immobilized on the BSA 3014 serving as a base material, remained. That is, the main sensor 3000*a* and the sub-sensor 3000*b* were formed on the insulating substrate 3006. In this manner, a differential type sensor 3000 having a dual glycated albumin sensor enzyme layer that differs only in the presence or absence of protease 3001 can be generated (FIG. 23I).

Note that, although a method of manufacturing patterning by a resist has been described in this embodiment, a metal mask having an opening on the first hydrogen peroxide electrode and a metal mask having an opening on the second hydrogen peroxide electrode may be used.

In some embodiments, the glycoprotein sensor (detection portion, detector) may comprise an albumin sensor (detection portion, detector). A glycated protein sensor and an albumin sensor may be combined and referred to as a sensor, and a system configured to be capable of measuring both glycated protein and albumin may be referred to as a glycated protein sensor. The sensor may be configured such that bodily fluids and liquids obtained from the same collection are applied to both the glycated protein sensor and the albumin sensor. In another embodiment, the sensor may be configured such that body fluids and liquids collected at different timings are supplied to the glycated protein sensor and the albumin sensor. In some embodiments, the glycated protein sensor may be configured to be connected to an albumin sensor. By cooperating with the albumin sensor, the glycoalbumin (GA) value can be measured more easily and efficiently.

As an albumin sensor, for example, measurement by a dye-binding method or an electrochemical method using a change in an absorption wavelength or an absorption spectrum when albumin is bound to a dye such as bromocresol green (BCG), bromocresol purple (BCP), or the like is possible. Further, it may be a device or an apparatus based on an immunoassay using an antibody or the like.

In some embodiments, the enzyme (ketoamine oxidase and/or protease) may be covered with a protective agent. The protective agent may be a protective layer, a protective film, or a protective coating.

Figure 24:
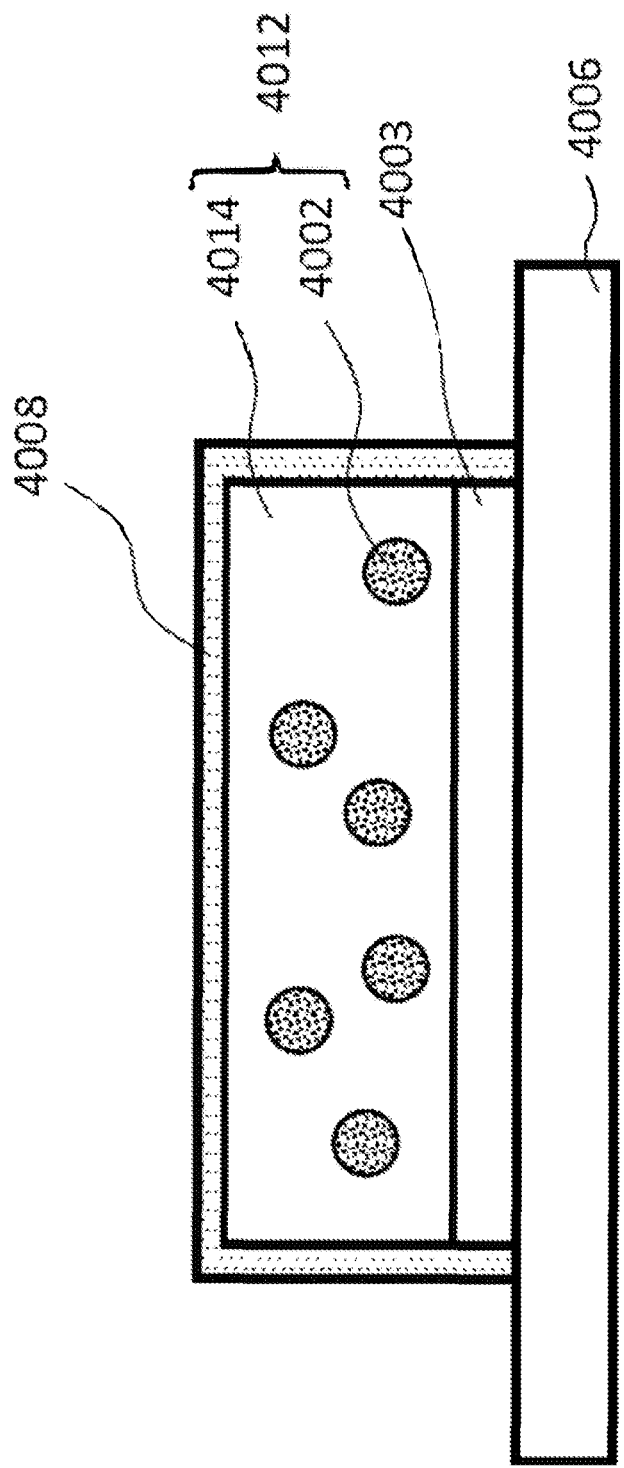
FIG. 24 illustrates a schematic showing the configuration of a portion of a sensor according to an embodiment of the present disclosure.

As shown in FIG. 24, a protective agent may be disposed to cover the enzyme layer. In FIG. 24, a ketoamine oxidase moiety is shown, and proteases and other elements and configurations have been omitted. Hydrogen peroxide detector 4003 is disposed on substrate 4006, on which ketoamine oxidase 4002 is encompassed within base material 4014 to form ketoamine oxidase layer 4012. Protective film 4008 is disposed so as to cover the ketoamine oxidase 4002 or the ketoamine oxidase layer 4012. The protective film 4008 may also be disposed to cover the hydrogen peroxide detector 4003.

Figure 25:
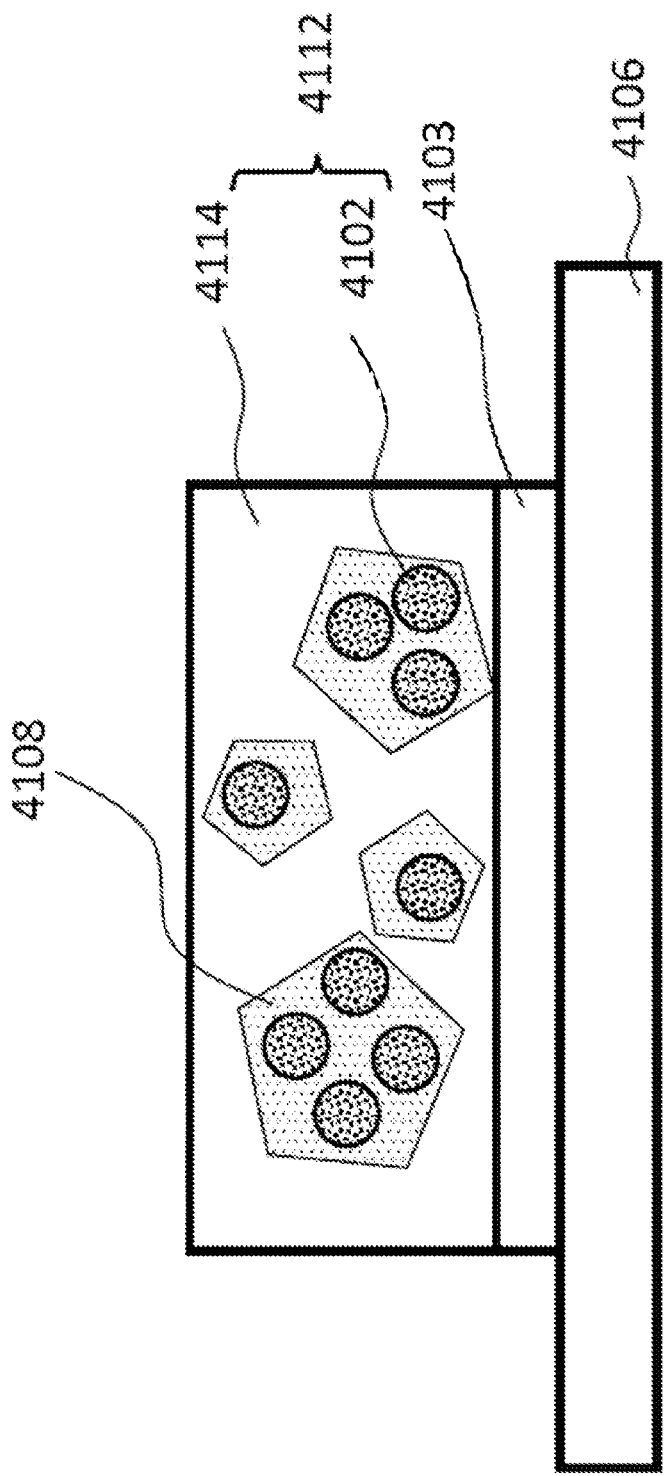
FIG. 25 illustrates a schematic showing the configuration of a portion of a sensor according to an embodiment of the present disclosure.

As shown in FIG. 25, the protectant may be disposed to cover each enzyme molecule, or may be disposed to cover a portion of the enzyme or an assembly of enzyme molecules. In FIG. 25, a ketoamine oxidase moiety is shown, and proteases and other elements and configurations have been omitted. Hydrogen peroxide detector 4103 is disposed on substrate 4106, on which ketoamine oxidase 4102 is encompassed within base material 4114 to form ketoamine oxidase layer 4112. The protective coating may cover the ketoamine oxidase 4102 individually or on a molecule-by-molecule basis. It may be formed so as to cover a plurality of ketoamine oxidases 4102.

In some embodiments, the protecting agent of the enzyme may be selected from the materials of the base material.

In some embodiments, the protecting agent of the enzyme may be of the same material as the base material of the enzyme. When the base material of the enzyme and the protective agent are formed of the same material, peeling or breakage due to thermal stress due to a difference in thermal expansion coefficient, due to, for example, heating during measurement or a temperature change at room temperature, can be avoided. Protective agents can avoid deterioration of the enzyme, or extend its life, for example without limitation. For example, a protease that is not immobilized to the device body, or a portion of the immobilized protease, may flow off and contact the ketoamine oxidase to degrade or denature it. Protective agents can avoid or suppress, for example, the degradation of such ketoamine oxidase. In some embodiments, a protecting agent for ketoamine oxidase may be formed of a material that is less likely to be degraded by protease.

As a method of forming a protective agent, a protective film may be formed after a FOAD film is applied (e.g., spin coating or bar coating), crosslinked (left standing, crosslinking time), and dried. The protective film may be formed so as to have a uniform film thickness. The protective film may be applied by spin coating, bar coating, blade coating, spray coating, or dipping depending on the nature of the solution used. The applied protective film may be held at a predetermined temperature for a predetermined time. The necessary film thickness may be obtained by the treatment after the coating.

The protective agent may be, for example but not limited to, a fluororesin, a photocurable resin, a water curable resin, cellulose (ethylcellulose, acetylcellulose, etc.), nylon, polystyrene, a non-protein resin, a polyion complex, a complex, an inorganic polymer, a solid polymer electrolyte, a porous polymer metal complex (e.g., ZIF-8), a metal organic structural body, or a phospholipid. In some embodiments, a protective agent for ketoamine oxidase may comprise albumin and may consist substantially of albumin. In some embodiments, albumin as a protective agent may be BSA. It was confirmed using a system where the life time of ketoamine oxidase without a protective agent is one week that the lifetime of the ketoamine oxidase was extended to about one month and the time to half the output was doubled by covering the ketoamine oxidase with the protecting agent by the BSA.

By way of non-limiting example, the protective agent can reduce the effect on lifetime due to thermal vibration, etc. due to the liquid. The enzyme may be comprehensively immobilized by a base material, may be partially immobilized, and may be coated by a base material. As one interpretation, a protective agent may protect a portion of an enzyme molecule that is exposed on a surface of a base material. As one interpretation, it can also be considered that protecting enzymes with protectants increases their lifetime. By way of non-limiting example, it is possible to reduce the effect of contaminants on the activity of enzymes, the efficiency of enzymatic reaction, and the like. By way of non-limiting example, protective membranes or the like can avoid or reduce the enzyme from falling off or leaving the base material. By way of non-limiting example, a protective film can avoid denaturation (protein denaturation) due to abrupt changes in parameters such as external pressure, pH, and salt concentration, which it undergoes during liquid feeding or the like.

Hereinafter, the protease and the ketoamine oxidase will be described with reference to some embodiments.

Example 1

The operating characteristics of various proteases were compared. As proteases, 16 mg of Orientase 22BF (HBI Enzymes Inc.), 133 mg of Nucleicin (HBI Enzymes Inc.), 12.8 mg of Orientase AY (HBI Enzymes Inc.), 8.0 mg of Orientase OP (HBI Enzymes Inc.), 16 mg of Sumizyme MP (SHINNIHON CHEMICALS Corporation), and 4 mg of Protease XIV (Sigma Aldrich Japan) were respectively dissolved in 400 µL of TES buffer solution and dialyzed overnight, which were used as protease solutions. 4 mg of Thermolysin (Fujifilm Wako Pure Chemical Corporation), 4 mg of Trypsin (Fujifilm Wako Pure Chemical Corporation), 4 mg of α-chymotrypsin (Tokyo Chemical Industry Co., Ltd.), 4 mg of Papain (Nacalai Tesque, Inc.), and 4 mg of Bromelain (Fujifilm Wako Pure Chemical Corporation) were also respectively dissolved in 400 µL of TES buffer and used as they were.

12 µL of GA-L calibrator (GA concentration: 14.9 mg/mL, albumin concentration: 47.9 mg/mL) of glycoalbumin kit Lucica GA-L (Asahi Kasei Pharma Corporation) and 93 µL of TES buffer solution were mixed, and 15 µL of protease solution was added thereto. The mixed solution was heated at 37° C. or 60° C. for 10 min using an aluminum block incubator. The mixed solution was removed from the aluminum block and placed in a refrigerator immediately so that digestion would not proceed at the residual heat or at room temperature, and then stored at a low temperature. This is referred to as GA-digested sample. Meanwhile, the protease solution and the TES buffer were mixed. This mixed solution was subjected to a heat treatment in the same manner. This is referred to as protease self-digested sample.

Absorbance measurements wered carried out using ALB R-2 solution, a commercially available glycoalbumin kit Lucica and a microplate reader. The digestion rate of albumin for each protease was determined from absorbance change before and after the digestion of GA-digested samples.

Figure 26:
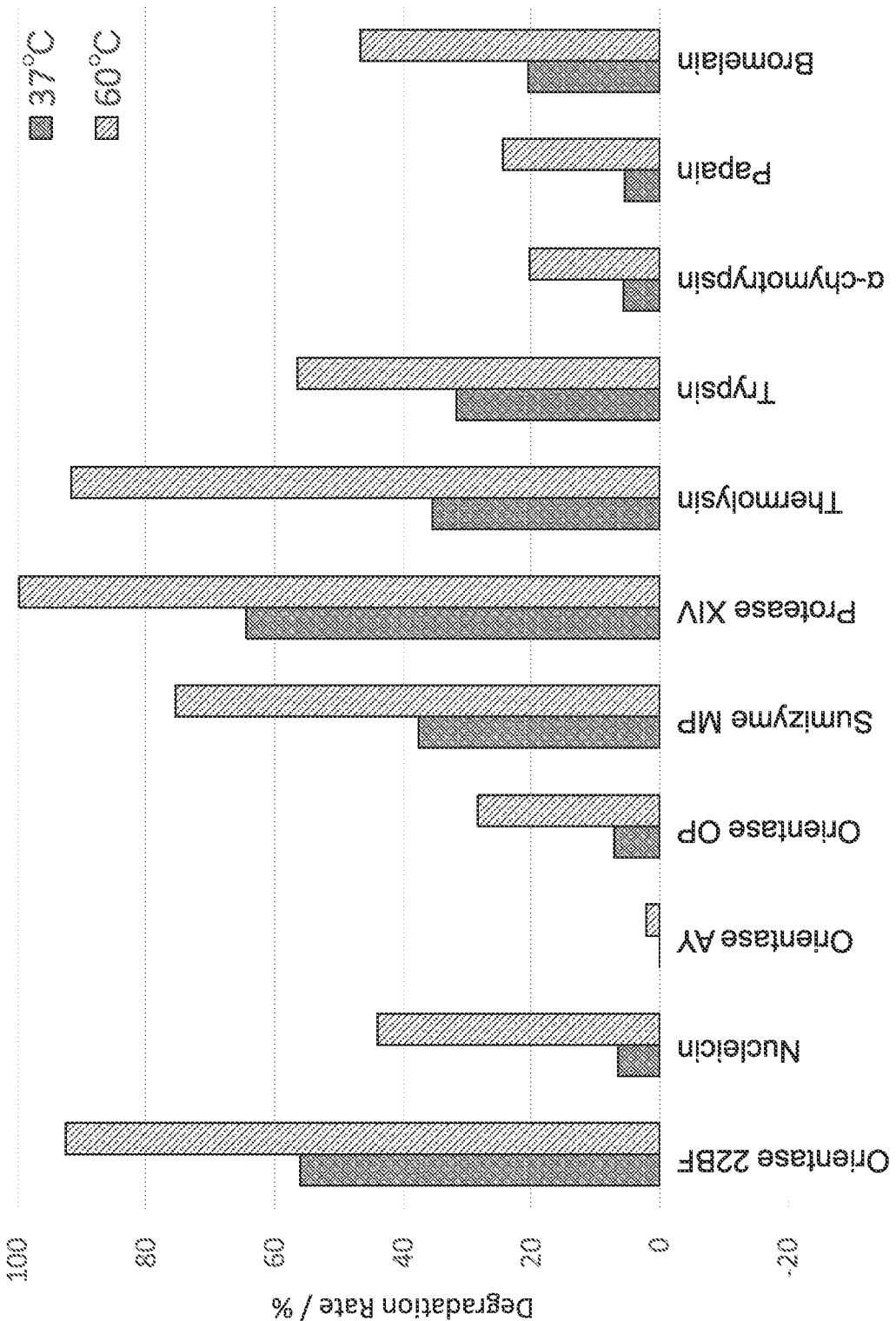
FIG. 26 shows a graph showing the degradation rate of proteases.

FIG. 26 shows the digestion rate at heating temperatures of 37° C. and 60° C. Orientase 22BF and protease XIV showed relatively high digestion rates at 37° C. At 60° C., Orientase 22BF, Protease XIV, Sumizyme MP, and Thermolysin showed relatively high digestion rates. Orientase 22BF, Protease XIV, Sumizyme MP, and Thermolysin are all bacterial-derived proteases. In one interpretation, a bacterial protease may have a higher digestion rate than an animal or plant derived protease, or an animal or plant derived protease may have a lower digestion rate than a bacterial protease. This interpretation is indicative of one idea, and there may be other theories or experimental results. Based on the present experimental results, in some embodiments, a protease selected from the group of Orientase 22BF, Protease XIV, Sumizyme MP, and Thermolysin may be used as a protease used for digestion of albumin. Alternatively, a plurality of proteases among them may be used in combination.

Figure 27:
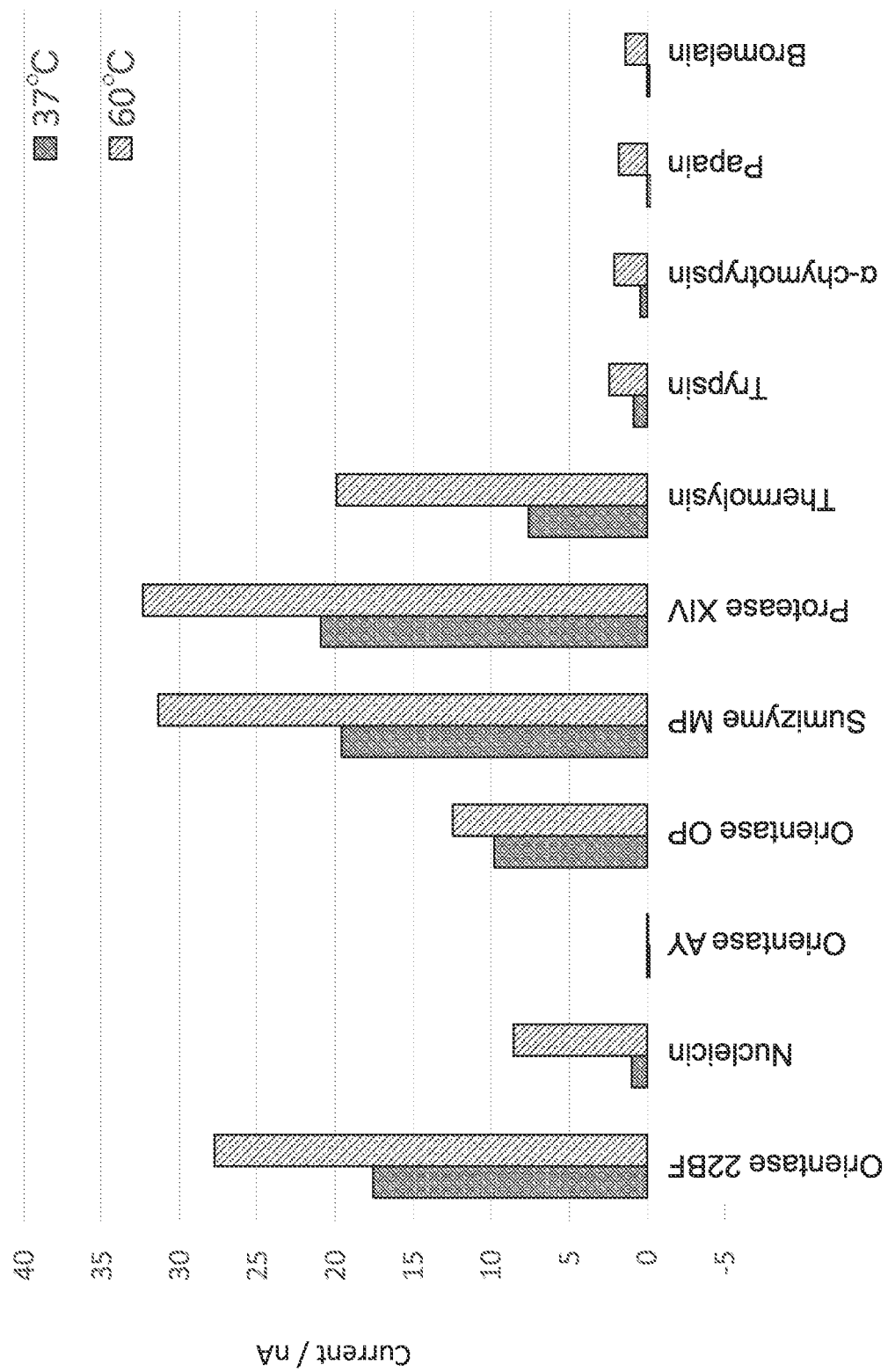
FIG. 27 shows a graph showing a sensor output for each protease.

In FIG. 27, the current of the GA-digested sample was measured using a FAOD electrode. From the difference between the output of the digested GA sample and that of the protease self-digested sample, the net output by the digested GA is shown. As shown in FIG. 27, Orientase 22BF, Protease XIV and Sumizyme MP gave relatively high outputs. One interpretation is that Orientase 22BF, Protease XIV and Sumizyme MPs are preferred proteases for digesting albumin to glycated peptide fragments of sizes that FAOD can respond to. This interpretation is indicative of one idea, and there may be other theories or experimental results.

Example 2

The operating temperature of the protease was investigated. 16 mg of Orientase 22BF (manufactured by HBI Enzymes Inc.) was dissolved in 400 µL of TES buffer and dialyzed overnight to be used as protease solution.

12 µL of GA-L calibrator (GA concentration: 14.9 mg/mL, albumin concentration: 47.9 mg/mL) of glycoalbumin kit Lucica GA-L (Asahi Kasei Pharma Corporation) and 93 µL of TES buffer solution were mixed, and 15 µL of protease solution was added thereto. At the same time, a sample solution containing only protease and a sample solution containing only calibrator were also prepared. These were held for 2.5 min or 10 min at each temperature of 20° C., 30° C., 40° C., 50° C., 60° C., and 70° C. using an aluminum block incubator. The mixed solution was removed from the aluminum block and placed in a refrigerator immediately so that digestion would not proceed at the residual heat or at room temperature, and then stored at a low temperature.

Figure 28:
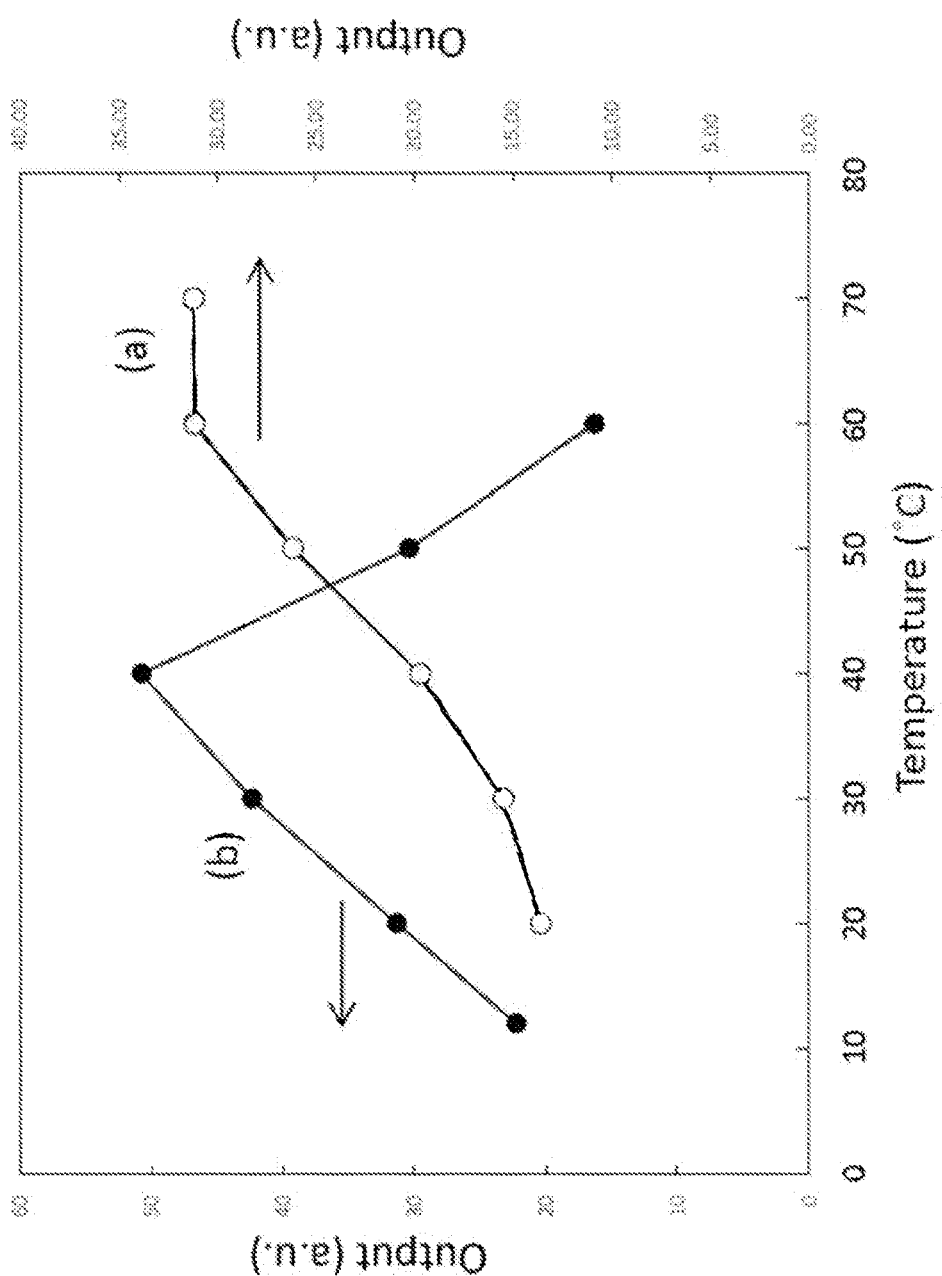
FIG. 28 shows a graph showing the dependence of the operation of protease and ketoamine oxidase on the temperature.

The output current value of the FAOD electrode was measured when the GA-digested samples was introduced. From the output current value of this GA digestion sample, the difference between the output current value of the protease-only sample solution (protease self-digested sample) and the output current value of the GA-only sample solution (GA digested sample), i.e., [output current value of the GA digested sample]−[output current value of the protease-only sample solution]−[output current value of the GA-only sample solution], was used as the net digested GA output current value. In FIG. 28, the output current value of the net digested GA was plotted as a function of the temperature of the digestion process (digestion temperature) (a).

As shown in FIG. 28, the output current value from FAOD electrode became highest around 60° C. or between 60° C. and 70° C. In some embodiments, the digestion temperatures of the proteases may be set to ranges where the output current values from FAOD electrodes are higher. For example, the digestion temperature of the protease may be set to around 60° C. or between 60° C. and 70° C. at which the output current value from FAOD electrode is higher in FIG. 28. The digestion temperature of the protease may be greater than or equal to 50° C., 55° C. or 60° C. The digestion temperature of the protease may be lower than or equal to the deactivation temperature of the protease. In some embodiments, the digestion temperature of the protease may be different from the optimal temperature range of FAOD.

Example 3

The operation temperature of ketoamine oxidase (FAOD) was examined. Trifluoroacetic acid salt of N-ε-(1-deoxyfructosyl)-L-lysine (FK) (Peptide Institute, Inc.) was dissolved in TES buffer to make 12.8 µM of FK solution. The output current value from FAOD electrode was measured when the FK solution was introduced, at respective temperatures of 10° C., 20° C., 30° C., 40° C., 50° C., and 60° C. ((b) in FIG. 28B).

As shown in FIG. 28, the output current value from the FAOD electrode became highest at around 40° C. In one interpretation, the optimal temperature range of the FAOD electrodes is around 40° C. The temperature of the FAOD electrodes or the vicinity thereof may be set to about 40° C. In some embodiments, the temperature of the FAOD electrode or vicinity thereof may be different from the optimum temperature or temperature range of the protease.

Example 4

The dependency of the output current of the FAOD electrode on the GA concentration was investigated. Albumin powders with different GA values were dissolved in TES buffer respectively, to prepare GA sample solutions. 4 mg of Protease XIV (Sigma Aldrich Japan) and 16 mg of Orientase 22BF (HBI Enzymes Inc.) were dissolved in 400 µL of TES buffer respectively, and dialyzed overnight to prepare protease solutions.

40 µL of latex beads (IMMUTEX P0113, Cosmo Bio Co., Ltd.) dispersion solution was mixed with 400 µL of TES buffer, and 50 mg of 4-(4,6-dimethoxy-1,3,5-triazine-2-yl)-4-methylmorpholinium chloride (DMT-MM, Tokyo Chemical Industry Co., Ltd.) was added thereto and dissolved, and this solution was stirred at room temperature for 2 hours. The supernatant was removed by centrifugation (12,000 rpm for 20 min). Additional 400 µL of TES buffer was added, and this solution was stirred. The same procedure was repeated three times to wash the beads and remove excess DMT-MM. After removing the supernatant at the third time, 400 µL of dialyzed protease solution was added, and this solution was stirred in a refrigerator for 4 hours. After centrifugation (12,000 rpm for 20 min) with additional 400/µL of TES buffer, the supernatant was removed. 800 µL of TES buffer was added and the solution was stirred. The same procedure was repeated three times to wash the beads to remove excess protease. After removing the supernatant at the third time, 200 µL of TES buffer was added and the solution was stored in the refrigerator.

60 µL of 1.67 mg/mL GA sample solution and 20 µL of protease-immobilized bead solution were mixed well. The mixed solution was heated using an aluminum block incubator for 30 minutes at 37° C. After 30 minutes, 40 µL of TES buffer was added, and after centrifugation (12,000 rpm for 30 minutes), the supernatant was separated. This solution served as a digested GA sample.

Figure 29:
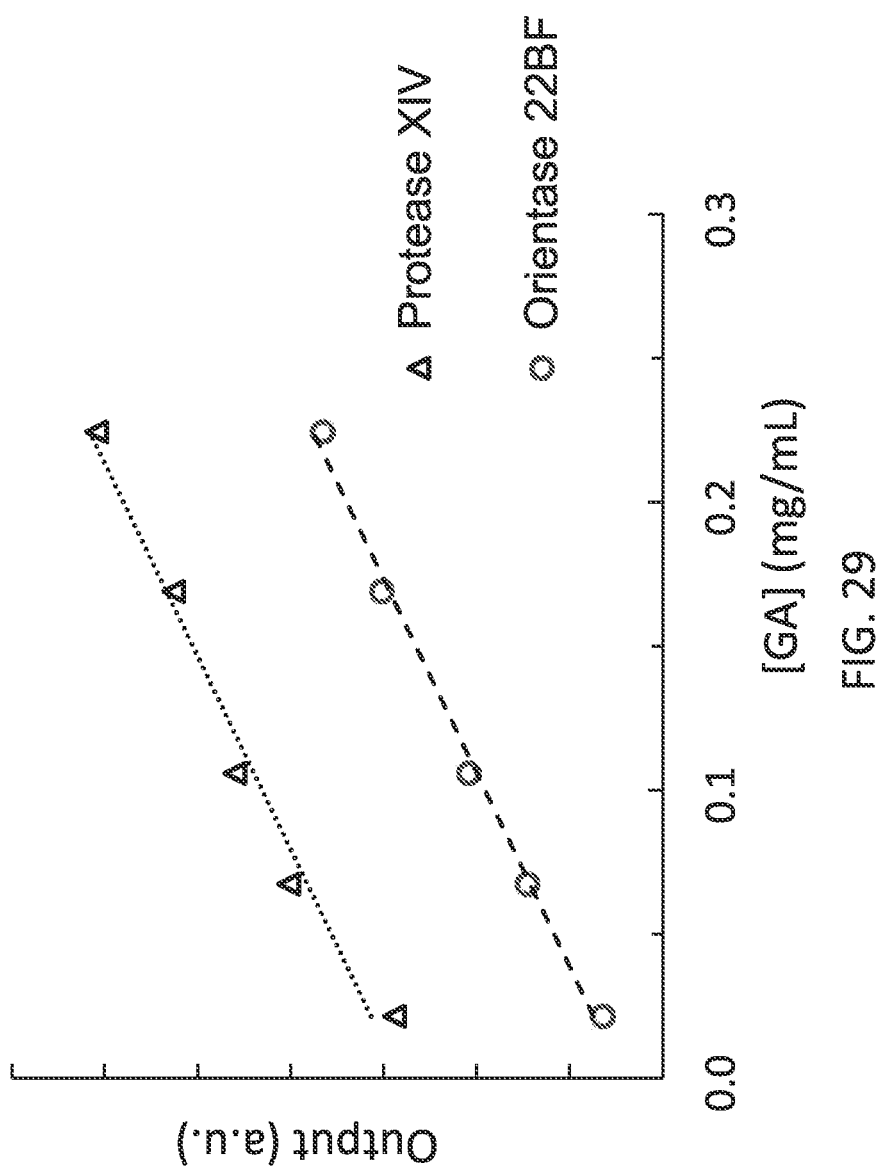
FIG. 29 shows a graph showing the dependence of the sensor output on the glycoalbumin concentration.

The digested GA-sample solution was introduced, and the output current values from the FAOD electrode were measured. FIG. 29 shows the output current values as a function of GA concentration. As shown in FIG. 29, although the intercept values differed depending on the protease, there was a linear relationship between the GA concentration and the output current value from the FAOD electrode by the digested GA samples. Furthermore, the GA solution was digested using protease immobilized on beads, and the output current value from FAOD electrode by its digestive solution was found to vary depending on the GA concentration of the system. Therefore, it was shown that the immobilized protease and the FAOD electrode can be used to measure GA-concentration.

6. Measurement Method

Hereinafter, some embodiments of the measurement method according to the present disclosure will be described.

A measurement solution containing the glycated protein is introduced into the sensor. The immobilized protease contacts the measurement solution containing a glycated protein to fragment this glycated protein and generate peptide fragments. After the generation, the peptide fragments diffuse and lead to immobilized ketoamine oxidase. The immobilized ketoamine oxidase generates hydrogen peroxide from the peptide fragments containing glycated amino acid residues among the peptide fragments. The hydrogen peroxide detector detects hydrogen peroxide generated by the ketoamine oxidase.

In some embodiments, glycated protein to be measured may be glycated albumin.

In some embodiments, first, a glycated protein sensor comprising an immobilized protease, an immobilized ketoamine oxidase, and a hydrogen peroxide detection portion is prepared. Further, a measurement solution containing a glycated protein is prepared. The measuring solution is then introduced into the glycated protein sensor. The glycated protein sensor is used to detect glycated proteins in the measurement solution.

In some embodiments, the concentration of the glycated protein may be determined from the output signal of the hydrogen peroxide detector. Detecting the glycated protein in the measurement solution may include determining or calculating the concentration of the glycated protein in the measurement solution.

The concentration of the glycated protein associated with the output signal from the hydrogen peroxide detection portion may be determined. In advance or prior to the desired measurement, the relationship, the correlation, the function, or the like between the concentration of the glycated protein in the calibration solution and the output signal of the hydrogen peroxide detector may be obtained. Using or referring to the reference data, the reference table, the association, the correlation, the function, and the like, thus obtained, the concentration of the glycated protein in the measurement solution may be determined from the output signal of the hydrogen peroxide detector obtained from the measurement solution. For example, when a detector measures a current, from the current value measured by an electric circuit, an operation may be performed to determine the concentration of glycated protein with reference to a table (calibration curve) associating the current value thereof with the concentration of glycated protein. The relevance or the like may be a calculation for obtaining a difference between a converted concentration value based on the current value from the main (first) sensor and a converted concentration value based on the current value from the sub (second) sensor.

In some embodiments, the glycated protein may be detected, the presence of the glycated protein above or above a certain threshold may be detected, the concentration of the glycated protein may be determined, the glycated protein may be quantified, and the degree of glycation of the protein may be determined.

In some embodiments, the amount of total protein which is the glycated protein to be measured and the corresponding non-glycated protein combined in the measurement solution or the concentration thereof in the solution may be determined. The glycated protein may be glycated albumin.

In some embodiments, a ratio or a proportion of a concentration of a glycated protein (glycated one of a target protein) to a concentration of a total amount of a target protein may be determined. In some embodiments, the average blood glucose level in the period from the previous measurement to the current measurement may be calculated by conversion from this ratio. In some embodiments, an average blood glucose level for a corresponding period of time may be determined from the ratio obtained from two consecutive measurements. In some embodiments, an average blood glucose level for a corresponding period of time may be determined from the ratio obtained from multiple measurements. In some embodiments, an average blood glucose level may be determined by dividing the sum of the ratios obtained from multiple measurements by the number of times. In some embodiments, the average blood glucose level may be determined as a weighted function of the ratio obtained at each time, and the function may be determined, as an example, to weigh the ratio more on more recent measurements.

In some embodiments, a measurement of glycated protein concentration may be notified to a user, such as an alert.

The user may be a person who actually uses a glycoprotein sensor, and may mean a person who measures glycoprotein of himself/herself or another person, a person who intends to measure, a person who is obliged or recommended to measure, or the like. The user may be an individual, may be a single or a plurality of individuals, or may be at least one. The user may be an organization such as one, a plurality, or at least one corporations or companies.

The notification to the user may be performed at a predetermined or appropriate timing. For the first and subsequent measurements, the notification may be performed at regular or indefinite intervals. The interval between any two measurements may be 3 days, 5 days, 6 days, 7 days, 10 days, 15 days, 20 days, 30 days, 40 days, 50 days, 60 days, 1 week, 2 weeks, 3 weeks, 4 weeks, 5 weeks, 6 weeks, 7 weeks, 8 weeks, 9 weeks, 10 weeks, 1 month, 2 months, 3 months, 4 months, 5 months, 6 months, or any other period. For a measurement of glycated albumin, it may be notified at a period such as 7 days, 10 days, 15 days, 20 days, 1 weeks, 2 weeks, 3 weeks, or the like.

In some embodiments, washing may be performed between multiple measurements. The wash may include flowing a buffer such as pure water, saline, TES, or the like, with respect to the whole or a portion of the immobilized protease, the immobilized ketoamine oxidase and the detection portion.

A program or a computer program according to some embodiments of the present disclosure may cause a computer to execute each step included in the measurement method described in the present application, or may cause a computer to read and execute the step. A computer-readable storage medium according to some embodiments of the present disclosure may store a program or a computer program for causing a computer to execute each step included in the measurement method described in the present application.

A01
A glycated protein sensor comprising:
    an immobilized protease;
    an immobilized ketoamine oxidase; and
    a hydrogen peroxide detection portion.

A01a
    The glycated protein sensor of embodiment A01,
    wherein the immobilized ketoamine oxidase is disposed proximate the hydrogen peroxide detection portion, A01b
    The glycated protein sensor of embodiment A01a,
    wherein the immobilized protease is disposed proximate the immobilized ketoamine oxidase.

A01c
    The glycoprotein sensor of any one of embodiments A01 to A01b,
    further comprising a liquid container portion for storing a liquid to be measured.

A01d
    The glycated protein sensor according to embodiment A01c,
    wherein a volume of the liquid container portion is 100 µL or smaller.

A02
A glycated protein sensor comprising:
    a hydrogen peroxide detection portion; and
    an enzyme layer being disposed on the hydrogen peroxide detection portion and comprising an immobilized protease and an immobilized ketoamine oxidase.

A03
    The glycated protein sensor of embodiment A02,
    wherein the enzyme layer has a laminate of a protease layer comprising an immobilized protease and a ketoamine oxidase layer comprising an immobilized ketoamine oxidase.

A04
    The glycated protein sensor of embodiment A03,
    wherein the ketoamine oxidase layer and the protease layer are laminated in the order of the ketoamine oxidase layer and the protease layer from the closer to the hydrogen peroxide detection portion.

A05
    The glycated protein sensor of embodiment A03,
    wherein the ketoamine oxidase layer includes a first ketoamine oxidase layer and a second ketoamine oxidase layer, and
    wherein the first ketoamine oxidase layer, the protease layer, and the second ketoamine oxidase layer are laminated in this order.

A06
The glycated protein sensor of embodiment A02,
wherein the enzyme layer comprises: a ketoamine oxidase layer comprising an immobilized ketoamine oxidase; and a protease immobilized on a surface of the ketoamine oxidase layer, opposite to the hydrogen peroxide detection portion.

A07
The glycated protein sensor of any one of embodiments A02 to A06,
further comprising an ion exchange resin disposed between the hydrogen peroxide detection portion and the enzyme layer.

A08
The glycated protein sensor of embodiment A01,
wherein the immobilized protease is disposed apart from the immobilized ketoamine oxidase.

A09
The glycated protein sensor of embodiment A08, comprising:
a protease container portion containing the immobilized protease;
a ketoamine oxidase container portion containing the immobilized ketoamine oxidase, and being fluidly connected to the protease container portion; and
a liquid feeding mechanism for feeding liquid from the protease container portion to the ketoamine oxidase container portion.

A10
The glycated protein sensor of embodiment A08 or A09,
further comprising a heater for heating the protease and/or the ketoamine oxidase.

A11
The glycated protein sensor of embodiment A08 or A09.
further comprising a protease heater for heating the protease container portion.

A12
The glycated protein sensor of embodiment A11,
wherein the protease heater is configured to heat the protease container portion to 40° C. or higher, or 50° C. or higher.

A13
The glycated protein sensor of embodiment A11 or A12,
further comprising a protease temperature sensor for measuring the temperature of the protease container portion or the protease.

A14
The glycated protein sensor of any one of embodiments A11 to A13,
further comprising a temperature control mechanism for controlling the heat value of the protease heater based on information from the protease temperature sensor.

A15
The glycated protein sensor of any one of embodiments 11 to A14,
further comprising a ketoamine oxidase heater for heating the ketoamine oxidase container portion.

A16
The glycated protein sensor of embodiment A15,
wherein the ketoamine oxidase heater is configured to heat the ketoamine oxidase container portion at a temperature of room temperature or higher and 50° C. or lower.

A17
The glycated protein sensor of embodiment A15 or A16,
further comprising a ketoamine oxidase temperature sensor for measuring the temperature of the ketoamine oxidase container portion or the ketoamine oxidase.

A18
The glycated protein sensor of any one of embodiments A15 to A17,
further comprising a temperature control mechanism for controlling the heat value of the ketoamine oxidase heater based on information from the ketoamine oxidase temperature sensor.

A19
The glycated protein sensor of any one of embodiments A11 to A18,
further comprising a cooling unit fluidly connected to both the protease container portion and the ketoamine oxidase container portion, the cooling unit comprising a cooling mechanism.

A21
The glycated protein sensor of embodiment 1,
wherein the immobilized protease,
the immobilized ketoamine oxidase, and
the hydrogen peroxide detection portion
are arranged in the above order from the upstream of the solution containing a test substance.

A22
The glycated protein sensor of any one of embodiments A01 to A21,
wherein the protease is immobilized to a base material, A23
The glycated protein sensor of embodiment A22,
wherein the protease is immobilized on a bead.

A24
The glycated protein sensor of any one of embodiments A01 to A23,
wherein the hydrogen peroxide detection portion includes a hydrogen peroxide electrode.

A25
The glycated protein sensor of any one of embodiments A01 to A23,
wherein the hydrogen peroxide detector includes a photodetector.

A26
The glycated protein sensor of any one of embodiments A01 to A23,
wherein the hydrogen peroxide detector includes a luminescent reagent that reacts with hydrogen peroxide and a photodetector.

A27
A glycated protein sensor comprising:
a first sensor comprising:
a first immobilized protease;
a first immobilized ketoamine oxidase; and
a first hydrogen peroxide detection portion, and
a second sensor comprising:
a second immobilized ketoamine oxidase; and
a second hydrogen peroxide detection portion.

A28
A glycated protein sensor comprising:
a first hydrogen peroxide detection portion;
a first enzyme layer being disposed on the first hydrogen peroxide detection portion and comprising an immobilized protease and an immobilized ketoamine oxidase;

a second hydrogen peroxide detection portion; and
a second enzyme layer being disposed on the second hydrogen peroxide detection portion and comprising an enzyme consisting substantially of the immobilized ketoamine oxidase.

A29
The glycated protein sensor of embodiment A28,
wherein the first hydrogen peroxide detection portion and the second hydrogen peroxide detection portion include a hydrogen peroxide electrode.

A30
The glycated protein sensor of embodiment A29,
wherein the first hydrogen peroxide detection portion comprises a first working electrode and one of a counter electrode and a reference electrode, and
wherein the second hydrogen peroxide detection portion comprises a second working electrode, the other of the counter electrode and the reference electrode.

A31
The glycated protein sensor of embodiment A29 or A30, further comprising a current measuring circuit for applying a potential to the counter electrode and measuring a current flowing through the first working electrode and a current flowing through the second working electrode.

A32
The glycated protein sensor of any one of embodiments A01 to A31,
wherein the glycated protein comprises glycated albumin.

A33
The glycated protein sensor of embodiment A32,
further comprising an albumin sensor.

B01
A method of measuring a glycated protein comprising:
providing a measurement solution including a glycated protein;
directing the measurement solution to an immobilized protease;
using the immobilized protease to fragment the glycated protein to generate peptide fragments;
using an immobilized ketoamine oxidase, to generate hydrogen peroxide from a peptide fragment comprising a glycated amino acid residue among the peptide fragments; and
using a hydrogen peroxide detector to detect the hydrogen peroxide generated by the ketoamine oxidase.

B02
A method of measuring a glycated protein, comprising:
providing a glycated protein sensor comprising:
an immobilized protease;
an immobilized ketoamine oxidase; and
a hydrogen peroxide detection portion;
providing a measurement solution containing a glycated protein;
directing the measurement solution to the glycated protein sensor; and
detecting the glycated protein in the measurement solution using the glycated protein sensor.

B03
The method for measuring a glycated protein, of embodiment B02,
further comprising: determining a concentration of the glycated protein associated with an output signal from the hydrogen peroxide detection portion.

B04
The method for measuring a glycated protein of embodiment B02 or B03,
wherein the glycated protein is glycated albumin or glycated hemoglobin, the method further comprising:
determining a concentration of albumin or hemoglobin; and
determining a glycated albumin value or glycated hemoglobin value, which is a ratio of the concentration of the glycated albumin or the concentration of the glycated hemoglobin to the concentration of the albumin or the concentration of the hemoglobin.

B05
The method for measuring a glycated protein of any one of embodiments B02 to B04, further comprising:
notifying a user that measurements of the concentration of the glycated protein should be taken every week, 2 weeks, 3 weeks, 4 weeks or 1 month.

B06
The method for measuring a glycated protein of any one of embodiments B02 to B05,
wherein the glycated protein comprises glycated albumin.

B07
The method for measuring a glycated protein of embodiment B06,
further comprising calculating an average blood glucose level from ratios of the albumin concentration or the hemoglobin concentration of a plurality of times.

B08
A program for causing a computer to execute each step included in the measurement method of any one of the embodiments B02 to B07.

B09
A computer readable storage medium storing the program of embodiment B07.

B10
A method of measuring a glycated protein, comprising:
providing a glycated protein sensor comprising:
a first hydrogen peroxide detection portion;
a first enzyme layer being disposed on the first hydrogen peroxide detection portion and comprising an immobilized protease and an immobilized ketoamine oxidase; and
a second enzyme layer being disposed on the second hydrogen peroxide detection portion and comprising an enzyme consisting substantially of the immobilized protease;
introducing a measurement solution containing a glycated protein to the glycated protein sensor; and
determining, from an output signal from the first hydrogen peroxide detection portion and an output signal from the second hydrogen peroxide detection portion, a concentration of the glycated protein associated with these output signals.

C01
A method for manufacturing a glycated protein sensor, comprising:
providing a substrate;
disposing a hydrogen peroxide detection portion on the substrate;
immobilizing a ketoamine oxidase on the substrate; and
immobilizing the protease on the substrate.

C02
The method of manufacturing a glycated protein sensor, of embodiment C01,
wherein said immobilizing the ketoamine oxidase on the substrate comprises immobilizing the ketoamine oxidase on the hydrogen peroxide detection portion, and wherein said immobilizing the protease on the substrate comprises immobilizing the protease on the hydrogen peroxide detection portion.

C03

The manufacturing method of embodiment C02, wherein said immobilizing the ketoamine oxidase on the hydrogen peroxide detection portion comprises forming a ketoamine oxidase layer having the ketoamine oxidase immobilized on a first base material, and wherein said immobilizing the protease on the hydrogen peroxide detection portion comprises forming on the ketoamine oxidase layer a protease layer having the protease immobilized on a second base material.

C04

The manufacturing method of embodiment C03, wherein said immobilizing the ketoamine oxidase on the hydrogen peroxide detection portion further comprises forming on the protease layer a second ketoamine oxidase layer having the ketoamine oxidase immobilized on a third base material.

C05

The manufacturing method of embodiment C02, wherein said immobilizing the ketoamine oxidase on the hydrogen peroxide detection portion, and said immobilizing the protease on the hydrogen peroxide detection portion comprises mixing the ketoamine oxidase and the protease with a common base material to form a same enzyme layer on the hydrogen peroxide portion.

C06

A method for manufacturing a glycated protein sensor, comprising:
providing a substrate;
forming a first hydrogen peroxide detection portion and a second hydrogen peroxide detection portion on the substrate;
immobilizing a first ketoamine oxidase and a protease on the first hydrogen peroxide detection portion; and
immobilizing a second ketoamine oxidase on the second hydrogen peroxide detection portion.

C07

The manufacturing method of embodiment C06, wherein said providing the substrate comprises providing a first substrate and a second substrate, and wherein said forming the first hydrogen peroxide detection portion and the second hydrogen peroxide detection portion on the substrate comprises forming the first hydrogen peroxide detection portion on the first substrate, and forming the second hydrogen peroxide detection portion on the second substrate, and the method further comprising:
providing a main body substrate; and bonding the first substrate and the second substrate on the main body substrate.

While several embodiments and examples of the present disclosure have been described above, these embodiments and examples/aspects are used for exemplarily explanations of the present disclosure. For example, each of the embodiments described above has been described in detail in order to explain the present disclosure in an easy-to-understand manner, and dimensions, configurations, materials, and circuits may be additionally changed as necessary. It is intended that the appended claims cover numerous modifications to the embodiments without departing from the spirit and scope of the present disclosure. Accordingly, the embodiments and examples disclosed herein have been shown by way of illustration and should not be considered as limiting the scope of the present disclosure.

The invention claimed is:

1. A glycated protein sensor comprising:
a hydrogen peroxide detection portion;
a first ketoamine oxidase layer being disposed on the hydrogen peroxide detection portion and comprising an immobilized ketoamine oxidase;
a protease layer being disposed on the first ketoamine oxidase layer and comprising an immobilized protease; and
a second ketoamine oxidase layer being disposed on the protease layer and comprising an immobilized ketoamine oxidase.

2. The glycoprotein sensor of claim 1, further comprising a liquid container portion for storing a liquid to be measured.

3. The glycated protein sensor of claim 2, wherein a volume of the liquid container portion is 100 µL or smaller.

4. The glycated protein sensor of claim 1, further comprising an ion exchange resin disposed between the hydrogen peroxide detection portion and the first ketoamine oxidase layer.

5. The glycated protein sensor of claim 1, further comprising a heater for heating the protease layer, the first ketoamine oxidase layer and the second ketoamine oxidase layer.

6. The glycated protein sensor of claim 5, further comprising a protease temperature sensor for measuring the temperature of the protease layer, the first ketoamine oxidase layer and the second ketoamine oxidase layer.

7. The glycated protein sensor of claim 6, further comprising a temperature control mechanism for controlling the heat value of the heater based on information from the temperature sensor.

8. The glycated protein sensor of claim 1, wherein the hydrogen peroxide detection portion includes a hydrogen peroxide electrode.

9. The glycated protein sensor of claim 1, wherein the glycated protein comprises glycated albumin.

10. The glycated protein sensor of claim 9, further comprising an albumin sensor.

11. A method of measuring a glycated protein, comprising:
providing a glycated protein sensor of claim 1;
providing a measurement solution containing a glycated protein;
directing the measurement solution to the glycated protein sensor; and
detecting the glycated protein in the measurement solution using the glycated protein sensor.

12. The method for measuring a glycated protein, of claim 11, further comprising: determining a concentration of the glycated protein associated with an output signal from the hydrogen peroxide detection portion.

13. The method for measuring a glycated protein, of claim 11,
wherein the glycated protein is glycated albumin or glycated hemoglobin,
the method further comprising:
determining a concentration of albumin or hemoglobin; and
determining a glycated albumin value or glycated hemoglobin value, which is a ratio of the concentration of the glycated albumin or the concentration of the glycated hemoglobin to the concentration of the albumin or the concentration of the hemoglobin.

14. The method for measuring a glycated protein of claim 11, further comprising:
notifying a user that measurements of the concentration of the glycated protein should be taken every week, 2 weeks, 3 weeks, 4 weeks or 1 month.

15. The method for measuring a glycated protein of claim 11, the method comprising repeating the steps of:
determining a concentration of albumin or hemoglobin; and
determining a glycated albumin value or glycated hemoglobin value, which is a ratio of the concentration of the glycated albumin or the concentration of the glycated hemoglobin to the concentration of the albumin or the concentration of the hemoglobin.

16. The method for measuring a glycated protein of claim 15, further comprising calculating an average blood glucose level from ratios of the albumin concentration or the hemoglobin concentration of a plurality of times.

17. A non-transitory storage medium having a program for causing a computer to execute each step included in the measurement method of claim 11.

18. The method for measuring a glycated protein, of claim 14,
wherein the glycated protein comprises glycated albumin.

19. A method for manufacturing a glycated protein sensor, comprising:
providing a substrate;
disposing a hydrogen peroxide detection portion on the substrate;
forming a first ketoamine oxidase layer having a ketoamine oxidase immobilized to a first base material;
forming on the first ketoamine oxidase layer a protease layer having a protease immobilized to a second base material; and
forming on the protease layer a second ketoamine oxidase layer having a ketoamine oxidase immobilized to a third base material.

* * * * *